(12) United States Patent
Kim et al.

(10) Patent No.: US 11,667,934 B2
(45) Date of Patent: Jun. 6, 2023

(54) PLATFORM FOR EXPRESSING PROTEIN OF INTEREST IN LIVER

(71) Applicant: TOOLGEN INCORPORATED, Seoul (KR)

(72) Inventors: Seokjoong Kim, Seoul (KR); Dong Woo Song, Seoul (KR); Kyu Jun Lee, Seoul (KR); Jung-Min Lee, Gyeongsangbuk-do (KR); Un-Gi Kim, Seoul (KR)

(73) Assignee: TOOLGEN INCORPORATED, Seoul (KR)

( * ) Notice: Subject to any disclaimer, the term of this patent is extended or adjusted under 35 U.S.C. 154(b) by 688 days.

(21) Appl. No.: 16/623,017

(22) PCT Filed: Jun. 15, 2018

(86) PCT No.: PCT/KR2018/006803
§ 371 (c)(1),
(2) Date: Dec. 16, 2019

(87) PCT Pub. No.: WO2018/231018
PCT Pub. Date: Dec. 20, 2018

(65) Prior Publication Data
US 2021/0095316 A1 Apr. 1, 2021

Related U.S. Application Data

(60) Provisional application No. 62/520,103, filed on Jun. 15, 2017, provisional application No. 62/662,907, filed on Apr. 26, 2018.

(51) Int. Cl.
| | |
|---|---|
| *C12N 15/90* | (2006.01) |
| *C12N 9/22* | (2006.01) |
| *C12N 9/64* | (2006.01) |
| *C12N 15/11* | (2006.01) |
| *C12N 15/86* | (2006.01) |
| *A61K 38/17* | (2006.01) |
| *A61P 7/04* | (2006.01) |
| *A61K 48/00* | (2006.01) |
| *C07K 14/775* | (2006.01) |
| *C12N 15/113* | (2010.01) |

(52) U.S. Cl.
CPC ............ *C12N 15/907* (2013.01); *C12N 9/22* (2013.01); *C12N 9/644* (2013.01); *C12N 15/11* (2013.01); *C12N 15/86* (2013.01); *C12N 2310/20* (2017.05); *C12N 2750/14143* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 2015/0056705 A1† | 2/2015 | Conway | |
| 2015/0166618 A1† | 6/2015 | Miller | |
| 2016/0340661 A1 | 11/2016 | Cong et al. | |

FOREIGN PATENT DOCUMENTS

| | | |
|---|---|---|
| CN | 105462968 A | 4/2016 |
| JP | 2014-526279 A | 10/2014 |
| KR | 10-2016-0089527 A | 7/2016 |
| WO | WO-2016/049230 A1 | 3/2016 |
| WO | WO-2017-077386 A1 | 5/2017 |
| WO | WO-2017/093804 A2 | 6/2017 |

OTHER PUBLICATIONS

Written Opinion of the International Searching Authority from corresponding PCT Application No. PCT/KR2018/006803, dated Nov. 15, 2018.
Ahn Sejun: "Establishment of F9 knock-out and Apoc3 Human sequence knock-in mouse for gene therapy study", Poster PS-D-14, Jan. 1, 2020.
Seki, S., et al.; "Efficient generation of knock out mice by the CRISPR/Cas9 system with two guide RNAs", Akita J Med, 2017, 44, pp. 37-43.
Extended European Search Report from corresponding European Patent Application No. 18817613.5, dated Feb. 26, 2021.
Office Action from corresponding Japanese Patent Application No. 2019-569246, dated Jul. 27, 2021.
Office Action from corresponding Japanese Patent Application No. 2019-569246, dated Jan. 1, 2022.
Nat Biotechnol., 2016, 34(2), p. 184-191.
Nagiec, M. M., et al.; "Modulators of Hepatic Lipoprotein Metabolism Identified in a Search for Small-Molecule Inducers of *Tribbles Pseudokinase 1* Expression", PLOS ONE, Mar. 26, 2015, pp. 1-26.
Jarrett, K. E., et al.; "Somatic genome editing with CRISPR/Cas9 generates and corrects a metabolic disease", Scientific Reports, Mar. 16, 2017, pp. 1-13.
International Search Report from corresponding PCT Application No. PCT/KR2018/006803, dated Nov. 15, 2018.
Office Action from corresponding Chinese Patent Application No. 201880052875.2, dated Jan. 10, 2023.
Yuting Guan, The Application of CRISPR-Cas9 System in Animal Model Building and Treatment of Hemophilia B, , Chinese Doctoral Dissertations Full-text Database, 2016, Issue 8, pp. 1-106, Aug. 15, 2016.

† cited by third party

*Primary Examiner* — Suzanne M Noakes
*Assistant Examiner* — Jae W Lee
(74) *Attorney, Agent, or Firm* — Harness, Dickey & Pierce, P.L.C.

(57) ABSTRACT

Provided is a platform for expressing a protein of interest by artificially manipulating the liver, and more particularly, to a platform for alleviating or treating a genetic disorder or improving a body function by inducing expression by inserting a transgene (e.g., a therapeutic gene) which can function or be expressed normally, into a high-expression secretory gene, instead of a disease gene which functions or is expressed abnormally. The high-expression secretory gene includes the HP or APOC3 gene. The transgene includes one that is highly expressed using a promoter in a hepatocyte genome and is secretory out of the cell.

15 Claims, 10 Drawing Sheets
Specification includes a Sequence Listing.

PLATFORM FOR EXPRESSING PROTEIN OF INTEREST IN LIVER

CROSS-REFERENCE TO RELATED APPLICATIONS

This application is a national phase application of PCT Application No. PCT/KR2018/006803, filed on Jun. 15, 2018, which claims priority to U.S. Patent Application Nos. 62/520,103, filed on Jun. 15, 2017 and 62/662,907, filed on Apr. 26, 2018. The entire disclosures of the applications identified in this paragraph are incorporated herein by references.

FIELD

The present invention relates to platform for expressing a protein of interest by artificially manipulating or modifying the liver. More particularly, the present invention relates to a platform for alleviating or treating a genetic disorder or improving a body function by inducing the expression of a transgene (e.g., therapeutic gene), which can function or be expressed normally, instead of a disease gene, which can function or be expressed abnormally, using a guide nucleic acid and/or an editor protein.

BACKGROUND

Gene therapy has enormous potential in the new era of human engineering. Gene therapy includes genome editing techniques, such as gene disruption, gene modification, and the insertion of a transgene that can be regulated by a specific exogenous promoter fused thereto or an endogenous promoter found at a genomic insertion site.

Today, intractable hemophilia or lysosomal storage diseases do not have suitable therapeutic agents, and alternative therapy using an enzyme or protein alternative is mainly used for treatment, but is not radical therapy. In addition, methods for expressing a therapeutic gene using AAV are being conducted in clinical trials, but these methods can also be expected to be effective only while AAV is expressed, so that they cannot be radical and long-term treatment methods.

Therefore, there is a need for a therapeutic platform that allows permanent expression by inserting an actual therapeutic gene into a patient's genome for longer and more effective treatment. Such a therapeutic platform is different from existing therapeutic methods through the temporary and repetitive administration of a therapeutic agent, and an efficient therapeutic platform can be developed using a target-specific programmable nuclease effective for gene correction to insert a therapeutic gene into a patient's genome.

For this reason, the inventors aimed to develop a therapeutic platform capable of continuously expressing a gene of interest using a target-specific programmable nuclease. Particularly, for high efficiency, an effective platform was completed by determining a site of a gene which is highly expressed in an organ or tissue (e.g., liver) as a site of the insertion of a gene of interest.

SUMMARY

Technical Problem

The present invention is directed to providing a platform expressing a protein of interest in hepatocytes using a CRISPR-Cas system.

The present invention is also directed to providing a composition for expressing a protein of interest, which includes a protein of interest or sequence encoding the same and using the CRISPR-Cas system, and various uses thereof.

The present invention is also directed to providing a cell expressing a protein of interest using the CRISPR-Cas system and a method of preparing the same.

The present invention is also directed to providing a method of expressing a protein of interest in hepatocytes using the CRISPR-Cas system.

The present invention is also directed to providing a method of treating a genetic disorder, which includes administering a composition for expressing a protein of interest in hepatocytes to a subject to be treated.

The present invention is also directed to providing a guide nucleic acid and an editor protein, which are able to be used in the manipulation of a corresponding target gene to express a protein of interest in hepatocytes.

Technical Solution

To solve the above-described problems, the present invention provides a platform expressing a protein of interest in hepatocytes. More specifically, the present invention provides a platform for improving body functions and treating a genetic disorder by inserting a gene encoding a protein of interest into a target gene using a CRISPR-Cas system to continuously express the protein at a high level and provide artificially modified cells, organ or tissue.

The "liver biofactory platform" used herein is a system capable of continuously expressing a protein of interest by inserting a specific transgene into a hepatocyte, which includes all compositions, methods and uses directly or indirectly involved therein.

In an example, the transgene artificially inserted may be integrated within a highly expressed and secretory gene in hepatocyte.

The highly expressed and secretory gene is at least one selected from the group consisting of ALB gene, FTL gene, FTH1 gene, ACT gene, HP gene, APOC3 gene, SOD2 gene, ORM1 gene, and F9 gene present in the genome of hepatocytes The transgene is expressed higher compared to before insertion, or the transgene is newly expressed in the hepatocyte.

In addition, the disclosure disclosed herein relates to a composition including a target-specific programmable nuclease for expressing a protein of interest in hepatocytes, and particularly, to a composition for manipulating a gene, which includes a programmable nuclease for inserting a transgene into a high-expression secretory gene, and is one or more genes selected from the group of the high-expression secretory genes.

In one example, the present invention provides a composition for expressing a protein of interest, which includes: a guide nucleic acid corresponding to a target sequence of one or more genes selected from the group of high-expression secretory genes expressed in the liver;

an editor protein or a nucleic acid encoding an editor protein; and a donor including a nucleotide sequence encoding a protein of interest.

The "high-expression secretory gene" refers to a gene expressed in hepatocytes at a predetermined level or more, which is highly expressed in hepatocytes, such that the expression product is secreted out of the hepatocytes. The high-expression secretory gene is present at a site in which it can be continuously expressed at a high level in the genome of a hepatocyte, and may have the function of a safe harbor site.

The highly expressed and secretory gene may be at least one selected from the group consisting of ALB gene, FTL gene, FTH1 gene, ACTB gene, HP gene, APOC3 gene, SOD2 gene, ORM1 gene, AAVS1 gene, Rosa gene, HPRT gene, and CCR5 gene.

The highly expressed and secretory gene may preferably be HP gene or APOC3 gene.

The programmable nuclease means artificially engineered nuclease, in an example The programmable nuclease is at least one selected from the group consisting of Clustered regularly interspaced short palindromic repeats (CRISPR)-CRISPR associated protein (Cas) system, Zinc finger nuclease (ZFN), Transcription activator-like effector nucleases (TALEN).

Modification in the nucleotide sequence may be unlimitedly and artificially manipulated by using a CRISPR-Cas system.

The "CRISPR-Cas system" refers to a system formed by the interaction between a guide nucleic acid recognizing and binding to the sequence of a gene of interest and an editor protein cleaving a target gene, and the CRISPR-Cas system includes a guide nucleic acid and an editor protein.

The CRISPR-Cas system may modify a target. The target may be a target nucleic acid, gene, chromosome or protein.

The editor protein which is one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein, or a nucleic acid encoding the same. In an example, The editor may be *Streptococcus pyogenes*-derived Cas9 protein or a *Campylobacter jejuni*-derived Cas9 protein.

The target sequence may be a continuous 10 bp to 25 bp nucleotide sequence located in an exon region of highly expressed and secretory gene sequence.

The target sequence may be a continuous 10 bp to 25 bp nucleotide sequence located in an intron region of highly expressed and secretory gene sequence.

The target sequence may be at least on selected from the group consisting of SEQ ID NO.: 1-348.

The guide nucleic acid may form a complementary bond with a part of the nucleotide sequence of at least one gene selected from the group of high-expression secretory genes. The guide nucleic acid may include 0 to 5, 0 to 4, 0 to 3, or 0 to 2 nucleotide(s) mismatched to the target sequence.

In one embodiment, the disclosure disclosed herein, A guide nucleic acid for the highly expressed and secretory gene at least one selected from the group consisting of ALB gene, FTL gene, FTH1 gene, ACTB gene, HP gene, APOC3 gene, SOD2 gene, ORM1 gene, AAVS1 gene, Rosa gene, HPRT gene, and CCR5 gene.

In an example, one or more guide nucleic acids selected from the following groups may be provided:

a guide nucleic acid for a target sequence selected from the group consisting of SEQ ID NO.: 1-153 of HP gene sequence;

a guide nucleic acid for a target sequence selected from the group consisting of SEQ ID NO.: 168-348 of APOC3 gene sequence;

in an embodiment, the composition for modifying a gene provides the guide nucleic acid is corresponding to target sequence selected from the group consisting of SEQ ID NO.: 1-40 and 154-167; and the composition further comprises a *Campylobacter jejuni*-derived Cas9 protein, or a nucleic acid encoding the Cas9 protein.

In another embodiment, the composition for modifying a gene provides the guide nucleic acid is corresponding to target sequence selected from the group consisting of SEQ ID NO.: 41-134 and 168-332; and The composition further comprises a *Streptococcus pyogenes*-derived Cas9 protein, or a nucleic acid encoding the Cas9 protein.

The guide nucleic acid may be, without limitation, any one of 18 to 25-bp, 18 to 24-bp, 18 to 23-bp, 19 to 23-bp, and 20 to 23-bp nucleotide sequences.

The guide RNA (gRNA) may be present in the form of dual RNA including crRNA and tracrRNA, or single-guide RNA (sgRNA).

The disclosure disclosed herein includes a transgene, which is a gene encoding a protein of interest.

The expression of a protein of interest may function to replace an existing protein or provide a new protein. Alternatively, a protein that is deficient or absent in the body is expressed, thereby treating a disease caused by deficiency or the absence of the protein or enhancing the function of the corresponding protein.

For example, a protein of interest may be a protein having a different characteristic (e.g., an increase in serum half-life) from the existing protein.

For example, a protein of interest may be a therapeutic gene of a certain disease. The therapeutic gene may be a gene that affects the expression and function of a disease-causing gene involved in a genetic disorder. The therapeutic gene may be a part (e.g., a functional domain) of a normal-type gene of a disease-causing gene (a mutated form of a normal gene) involved in a genetic disorder.

The disease may be a disease that can be treated by an antibody.

The disease may be caused by mutations in various genes. For example, the disease may be a disease related to "inherited metabolic disorders." For example, the disease may be hemophilia.

The therapeutic gene, that is, the normal form of a disease-causing gene, may be selected from the group consisting of FVII, FVIII, FIX and different coagulation factors.

The therapeutic gene, that is, the normal form of a disease-causing gene, may be selected from the group consisting of IDUA, I2S, SGSH, NAGLU, HGSNAT, GNS, GALNS, GLB1, ARSB, GUSB, HYAL, NEU, GNPTAB and MCOLN1.

The therapeutic gene, that is, the normal form of a disease-causing gene, may be selected from the group consisting of SAH1, GALC, CTSA, GLA, NAGA, beta-galactosidase, hexosaminidase, GBA, SMPD1, ARSA and SUMF.

The therapeutic gene, that is, the normal form of a disease-causing gene, may be selected from the group consisting of NPC, PPT, TPP1, CLN3, CLN6, PPT1, DNAJC5, CTSF, CLN7, CLN8 and CTSD.

The therapeutic gene, that is, the normal form of a disease-causing gene, may be GAA or LAMP2.

The therapeutic gene, that is, the normal form of a disease-causing gene, may be CTNS, CTSK or SLC17A5.

The therapeutic gene, that is, the normal form of a disease-causing gene, may be selected from the group consisting of MAN2B, MAN2C, MANBA, AGA, FUCA1 and LAL.

The therapeutic gene, that is, the normal form of a disease-causing gene, may be a gene encoding a protein selected from the group consisting of methylmalonic aciduria CbIA Type (MMAA) protein, methylmalonic aciduria CbIB Type (MMAB) protein, methylmalonic aciduria CbIC Type (MMADHC) protein, 5-Methyltetrahydrofolate-Homocysteine Methyltransferase Reductase (MTRR) protein, lysosomal membrane protein domain (LMBRD 1) protein, 5-Methyltetrahydrofolate-Homocysteine Methyltransferase (MTR) protein, propionyl-CoA protein, glucose-6-phosphate transporter (G6PT) protein, glucose-6-phosphatase (G6Pase) protein, low density lipoprotein receptor (LDLR) protein, low density lipoprotein receptor adaptor protein 1 (LDLRAP-1 protein), N-acetylglutamate synthetase (NAGS) protein, carbamoyl phosphate synthetase 1 (CPS1) protein, ornthine transcarbamylase (OTC) protein, argininosuccinic acid synthetase (ASS) protein, argininosuccinase acid lyase (ASL) protein, arginase (ARG1) protein, solute carrier family 25 protein, UDP glucuronosyltransferase 1 family, polypeptide A1 (UGT1A1) protein, fumarylacetoacetate hydrolyase (FAH), alanine-glyoxylate aminotransferase (AGXT) protein, glyoxylate reductase/hydroxypyruvate reductase (GRHPR) protein, APTase $Cu^{2+}$ transporting beta (ATP7B) protein, phenylalanine hydroxylase (PAH) protein, and lipoprotein lyase (LPL) protein.

The therapeutic gene may be a gene encoding an antibody. That is, the therapeutic gene may be a gene encoding a protein or polypeptide, which blocks a specific factor or signal pathway involved in the cause of a disease, by an antibody.

The therapeutic gene may be fused with a specific peptide that can be penetrated into specific tissue, such as the blood-brain barrier (BBB), or a functional peptide capable of increasing a therapeutic effect of the therapeutic gene.

In addition, the specification provides a transgene-inserted, artificially modified cell, tissue or organ using the guide nucleic acid and/or editor protein.

The modified cell, tissue or organ is an organ or tissue in which the protein of interest is expressed by inserting a transgene into a target sequence in a genomic gene of interest using a CRISPR-Cas system. In the artificially modified cell, tissue or organ, the protein of interest is continuously highly expressed at a certain level or more by being inserted in a highly expressed and secretory gene position in liver cells.

In one exemplary embodiment of the disclosure disclosed herein, the highly expressed and secretory gene may be at least one selected from the group consisting of FTL gene, FTH1 gene, ACTB gene, HP gene, APOC3 gene, SOD2 gene, ORM1 gene, and F9 gene.

the transgene artificially inserted in the highly expressed and secretory gene, and a hepatocyte including a protein of interest expressed from the transgene.

In one example, the highly expressed and secretory gene may be HP gene or APOC3 gene.

The transgene may be included in the exon or the intron of the highly expressed and secretory gene.

The transgene is expressed by a promoter originally present in the hepatocyte genome.

The hepatocyte may be a hepatic stem cell including an unlimitedly manipulated locus (e.g., high-expression secretory gene locus). Specific stem cell types that can be used with the methods and composition of the present specification include an adult stem cell, an embryonic stem cell (ESC), and induced pluripotent stem cell (iPSC).

In another exemplary embodiment of the disclosure disclosed herein, as a method of artificially manipulating a hepatocyte to express a protein of interest by artificially inserting a transgene into the hepatocyte genome, the method includes introducing, into a hepatocyte, a programmable nuclease for manipulating a high-expression secretory gene present in the hepatocyte genome; and a donor sequence including a transgene, wherein the transgene is inserted into the high-expression secretory gene present in the hepatocyte genome, and the high-expression secretory gene is one or more genes selected from FTL, FTH1, ACTB, HP, APOC3, SOD2, ORM1 and F9.

The introduction of a guide nucleic acid, an editor protein and a donor into the hepatocyte may be performed by one or more means selected from liposomes, plasmids, virus vectors, nanoparticles or a protein translocation domain (PTD)-fused protein.

The guide nucleic acid, editor protein and donor may be respectively encoded in at least one vector in the form of a nucleic acid sequence.

The vector may be a viral vector system. the viral vector may be at least one selected from the group consisting of adenovirus, adeno-associated virus (AAV), vaccinia virus, poxvirus, herpes simplex virus and lentivirus.

Also, introducing the programmable nuclease and donor into the hepatocyte is performed in vivo.

Intra-subject delivery methods may be systemic or topical application. the systemic administration may be a intravenous administration.

Also, introducing the programmable nuclease and donor into the hepatocyte is performed ex vivo. Intra-subject delivery methods may be electroporation.

a method of treating a specific disease, which includes administering a composition for continuously expressing a protein of interest in a hepatocyte at a certain level or more to treat the specific disease, is provided.

The specific disease may be a disease caused by deficiency or the absence of a specific protein.

The treatment method includes administering a composition including a composition for manipulating a gene for expressing a transgene artificially inserted into the hepatocyte genome as an active ingredient to a subject to be treated.

The composition for modifying a gene may include at least one selected from Clustered regularly interspaced short palindromic repeats (CRISPR)-CRISPR associated protein (Cas) system, Zinc finger nuclease (ZFN), or Transcription activator-like effector nuclease (TALEN).

For example, as a method of treating hemophilia, a method of treating hemophilia, which includes administering a composition for manipulating a gene for inserting transgene F9 into a HP or APOC3 gene sequence in a hepatocyte is disclosed.

The subject to be treated may be any one of mammals including primates such as human and monkeys, and rodents such as mice and rats.

In yet another exemplary embodiment of the disclosure disclosed herein, all aspects of the therapeutic uses for a specific disease are provided.

Advantageous Effects

As disclosed herein, a platform for expressing a protein of interest in a hepatocyte, the protein of interest can be continuously expressed at a high level, and a fundamental therapeutic agent for improving a body function and treating a genetic disorder can be provided.

For example, a genetic disorder caused by deficiency or the absence of a specific protein can be prevented or treated by producing a therapeutic protein to express a deficient or deleted protein by a composition described in the present specification or providing a new protein having a different characteristic (e.g., an increase in half-life).

DETAILED DESCRIPTION

Figure 1:
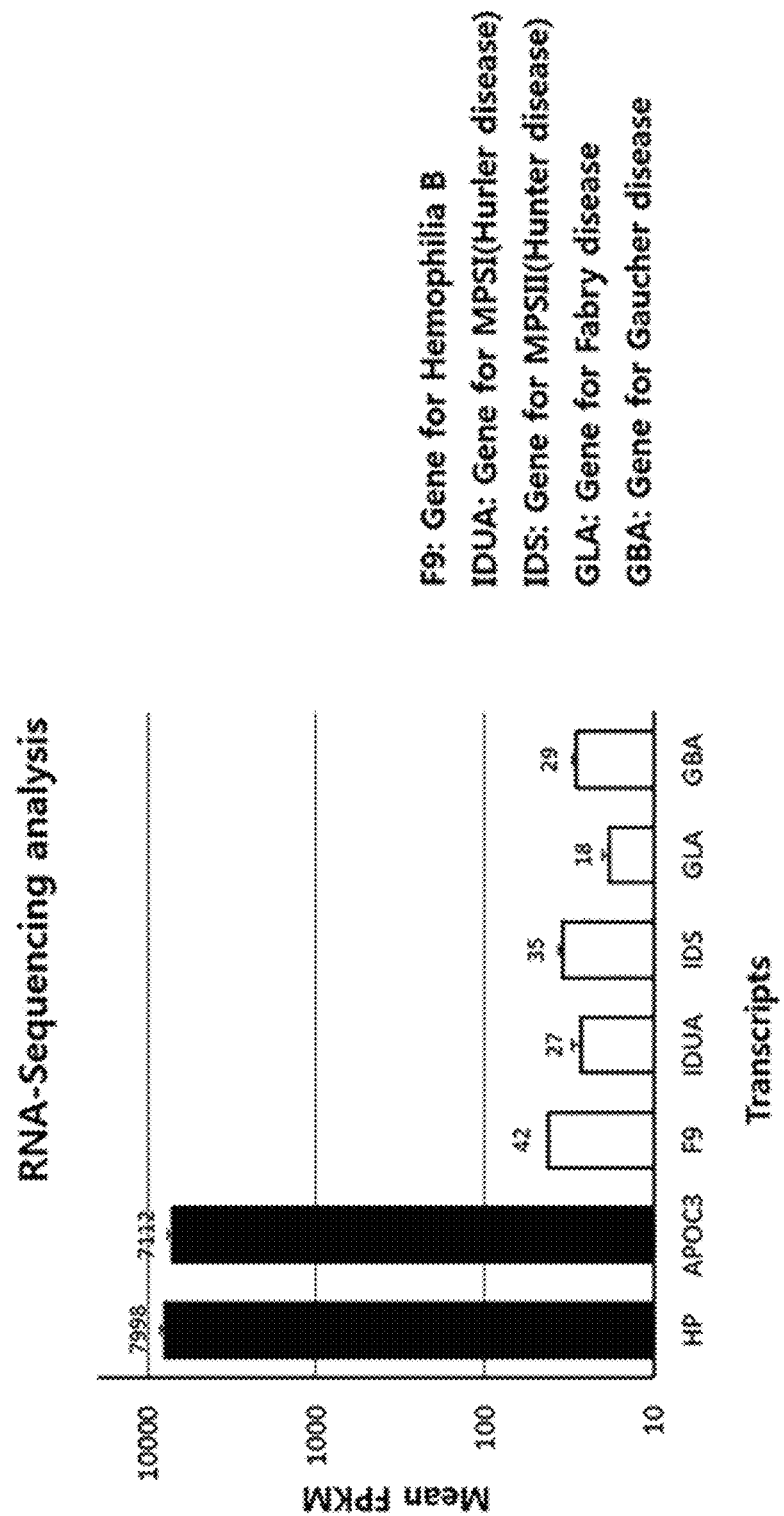
FIG. 1 is a graph showing the result of RNA-sequencing for selecting a high-expression secretory gene.
Figure 2:
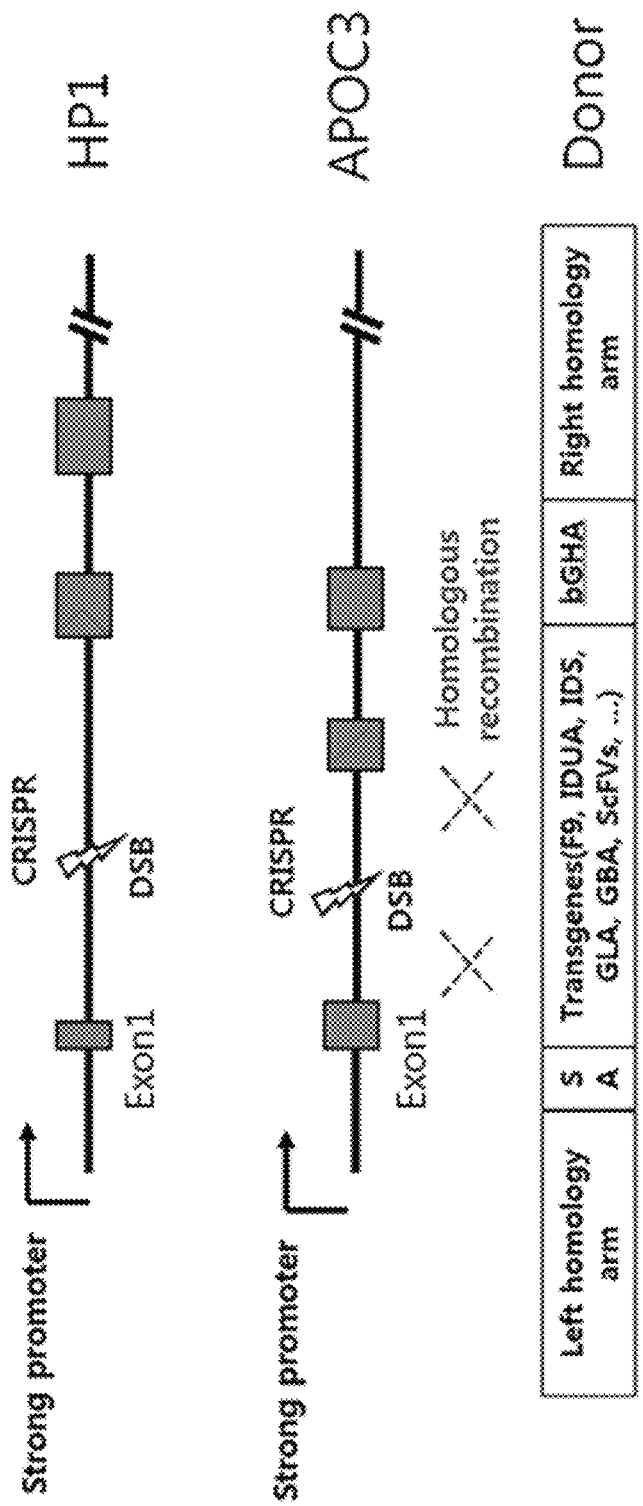
FIG. 2 is a diagram of a liver biofactory platform formed by artificial manipulation of a high-expression secretory gene.

Unless defined otherwise, all technical and scientific terms used herein have the same meaning as commonly understood by those of ordinary skill in the art to which the present invention belongs. Although methods and materials similar or identical to those described herein can be used in practice or testing of the present invention, suitable methods and materials are described below. All publications, patent applications, patents and other references mentioned herein are incorporated by reference in their entirety. In addition, materials, methods and examples are merely illustrative, and not intended to be limited.

The disclosure disclosed herein relates to a platform for expressing a protein of interest in the liver.

More specifically, the disclosure disclosed herein includes a composition for expressing a protein of interest by artificially manipulating a high-expression secretory gene using a CRISPR-Cas system, a cell, organ or tissue artificially manipulated to express a protein of interest, and a use of the composition, the cell, organ or tissue to treat, prevent or alleviate a specific genetic disorder or improve a body function.

[Liver Biofactory Platform (LBP)]

One exemplary embodiment disclosed herein relates to a "platform for expressing a protein of interest."

A platform for expressing a protein of interest is the generic term for systems that can continuously produce (express) a large amount of protein of interest in a specific organ or tissue by artificially inserting a transgene in a wild-type genome, and includes aspects of a composition, a use and a method.

In addition, the platform includes a system for secreting a protein of interest, which is produced (expressed), out of a cell. Therefore, the produced protein of interest may function not only in an organ or tissue into which a transgene is inserted, but also in an organ or tissue to which the protein is secreted.

In one exemplary embodiment, the platform may sufficiently produce a protein of interest at a certain level or more.

In another exemplary embodiment, the platform may sufficiently secrete the produced protein of interest out of a cell to be operable even in a different organ or tissue.

In the present specification, a specific organ or tissue realizing a platform for expressing a protein of interest is the liver or liver tissue.

The liver is an organ called a chemical factory of the human body, that is involved in all events happening in the body, and is responsible for metabolism of nutrients, detoxification and immune function through natural kinds of enzymes. Particularly, the human body can produce and store various substances necessary for suitable functions, and then deliver the substances to the entire body through the hepatic vein.

For example, a large amount of specific protein may be produced by highly expressing a specific gene in the liver, and a corresponding protein may be provided to a required organ by secreting the produced protein to the entire body.

Hereinafter, a liver biofactory platform (hereinafter, called "LBP") will be described.

In one aspect disclosed herein, an LBP is a system for continuously producing a protein of interest in liver tissue, and the system includes all substances, compositions, methods and uses directly or indirectly involved in the secretion of a produced protein out of cells.

The LBP includes a system producing a protein of interest in a hepatocyte by artificially manipulating a hepatocyte, for example, a genome in the hepatocyte.

For example, the LBP includes the artificial modification of a hepatocyte genome sequence.

In one exemplary embodiment, the LBP includes the cleavage of a partial sequence of a specific gene of the hepatocyte genome.

In another exemplary embodiment, the LBP includes the insertion of a transgene encoding a protein of interest into the cleaved sequence of the hepatocyte genome.

In the disclosure disclosed herein, the LBP may use various types of liver-derived cells.

For example, the LBP may include a hepatocyte, an induced pluripotent cell (iPSC) or a different type of stem cell (embryonic, hematopoietic, or mesenchymal cells), but the present invention is not limited thereto.

The LBP may utilize a specific region in a hepatocyte genome to highly express a protein of interest in the liver.

In one example, a transgene may be inserted into a safe harbor site in the genome of a hepatocyte.

The "safe harbor site" is a specific region in a genome in which there is no serious side effect, for example, cancer, even though a foreign gene is inserted, and a foreign gene inserted into the specific region can be permanently and safely expressed at a high level.

In another example, a transgene may be inserted into a region capable of using a gene expression regulatory region in the genome of a hepatocyte.

The "gene regulatory region" is a region playing a critical role for the regulation of gene expression present in a hepatocyte genome, and for example, is the generic term for regions including a promoter and/or regulatory factors (an enhancer, a transcription promoting factor, etc.) adjacent to a sequence including genetic information. A foreign gene inserted using the promoter and/or regulatory factor can be highly expressed with high efficiency.

The LBP may produce a large amount of protein of interest by continuously expressing a transgene at a high level using a specific site of the genome in a hepatocyte.

Highly Expressed and Secretory Gene

In the disclosure disclosed herein, the specific site into which a transgene is inserted in the hepatocyte genome may be included in a part of the sequence of a "high-expression secretory gene." In the specification, the high-expression secretory gene is also referred to as a target gene that achieves artificial manipulation in a hepatocyte genome.

The "high-expression secretory gene" refers to a gene which can be highly expressed continuously in a hepatocyte, and secrete the expression product out of the cell.

For example, the high-expression secretory gene may be included in any one of safe harbor sites in the genome of a hepatocyte.

For example, the high-expression secretory gene may include a promoter and a regulatory factor, which can highly express a gene continuously in the genome of a hepatocyte.

The high-expression secretory gene may be a wild-type gene present in the genome of a hepatocyte.

The term "wild type" means a gene which is most commonly shown in nature, or an allele designated as normal. For example, the wild type may be a normal-state gene type which does not exhibit a specific disease.

In addition, the highly expressed and secretory gene may be a gene that does not function normally in genome of hepatocyte.

Here, the high-expression secretory gene may be a gene in which one or more specific nucleotides are modified compared to a wild type. For example, the modification includes deletion, substitution, and/or insertion of one or more nucleotides. The modified high-expression secretory gene may be entirely or partially expressed, or may not be expressed at all.

In the disclosure disclosed herein, a transgene capable of expressing a desired protein is integrated into the highly expressed and secretory gene sequence.

Here, the corresponding high-expression secretory gene may be entirely or partially expressed. That is, the transgene and the high-expression secretory gene may be expressed together.

Alternatively, the corresponding high-expression secretory gene may be expressed in a hepatocyte and secreted into blood.

Alternatively, the corresponding high-expression secretory gene may not be expressed at all.

The highly expressed and secretory gene, for example, may be, ALB gene, FTL gene, FTH1 gene, ACTB gene, HP gene, APOC3 gene, SOD2 gene, ORM1 gene, AAVS1 gene, Rosa gene, or HPRT gene. In another example, the highly expressed and secretory gene may be IDUA gene, IDS gene, GLA gene, or GBA gene.

In an example, the highly expressed and secretory gene may be HP gene.

The HP gene means a gene encoding haptoglobin. In one example, the HP gene may be one or more genes selected from the group consisting of genes as follows, but the present invention is not limited thereto: a gene encoding human HP (e.g., NCBI Accession No. NP_001119574, NP_001305067, NP_005134) or mouse HP (NP_001316894, NP_059066), for example, an HP gene expressed by NCBI Accession No. NM_001126102, NM_005143, or NM_001318138.

In another embodiment, the highly expressed and secretory gene may be APOC3 gene.

The apolipoprotein C3 (APOC3) gene means a gene encoding apolipoprotein C-III, which is a component of a very low density lipoprotein (VLDL). The APOC3 gene may be one or more genes selected from the group consisting of genes as follows, but the present invention is not limited thereto: a gene encoding human APOC3 (e.g., NCBI Accession No. NP_000031), for example, the APOC3 gene expressed by NCBI Accession No. NM_000040.

In one example of the disclosure disclosed herein, an LBP system expressing a transgene artificially inserted into a hepatocyte genome is provided, The transgene is integrated within the highly expressed and secretory gene.

The highly expressed and secretory gene may be at least one selected from the group consisting of ALB gene, FTL gene, FTH1 gene, ACTB gene, HP gene, APOC3 gene, SOD2 gene, ORM1 gene, and F9 gene.

The LBP system is that the transgene is expressed higher compared to before insertion, or the transgene is newly expressed in the hepatocyte.

[Composition for Expressing Protein of Interest]

One exemplary embodiment of the disclosure disclosed herein relates to a composition which can realize a "platform for expressing a protein of interest."

The composition includes a composition capable of realizing an LBP system expressing a transgene artificially inserted into a hepatocyte genome.

In one exemplary embodiment, a composition for artificially manipulating a high-expression secretory gene is provided.

The composition for artificially manipulating a high-expression secretory gene may modify an arbitrary region in the high-expression secretory gene.

The term "artificially manipulated" means a state in which an artificial modification is applied, not a state of being as it is that occurs in a natural state. For example, some nucleotides of a gene may be deleted or substituted, and a gene may be modified by inserting a foreign nucleotide or polynucleotide.

The composition for artificially manipulating a high-expression secretory gene includes a programmable nuclease.

The "programmable nuclease" includes all types of nucleases which recognize a specific site on a chromosome of interest to cleave the genome. Particularly, the programmable nuclease may be a clustered regularly interspaced short palindromic repeats (CRISPR)-CRISPR associated protein (Cas) system, which is a domain recognizing a specific target sequence on a chromosome, a transcription activator-like effector nuclease (TALEN) in which a transcription activator-like (TAL) effector domain and a cleavage domain, which are derived from a plant pathogen, are fused, zinc-finger nuclease, meganuclease, RNA-guided engineered nuclease (RGEN), Cpf1, FokI-endonuclease or a combination thereof, but the present invention is not limited thereto.

The programmable nuclease is preferably the CRISPR-Cas system, but the present invention is not limited thereto.

[CRISPR-Cas System]

Another exemplary embodiment disclosed herein relates to a composition including using a CRISPR-Cas system for artificially manipulating a high-expression secretory gene.

The CRISPR-Cas system may consist of a guide nucleic acid and/or an editor protein.

In one exemplary embodiment disclosed herein, the composition for manipulating a high-expression secretory gene may include a guide nucleic acid for manipulating a high-expression secretory gene.

The term "guide nucleic acid" means a nucleotide sequence which can recognize a target nucleic acid, gene or chromosome, and interact with an editor protein. Here, the guide nucleic acid may form a complementary bond with some nucleotides in a target nucleic acid, gene or chromosome.

The guide nucleic acid may form a guide nucleic acid-editor protein complex, and serve to allow the guide nucleic acid-editor complex to be located in a target region of a target nucleic acid, gene or chromosome.

The guide nucleic acid may be target DNA-specific gRNA, DNA encoding the gRNA, or a DNA/RNA mixture.

The guide nucleic acid may be gRNA.

The "guide RNA (gRNA)" may be transcribed in vitro, and particularly, transcribed from an oligonucleotide double strand or plasmid template, but the present invention is not limited thereto.

The guide nucleic acid may be one continuous nucleic acid sequence.

For example, the one continuous nucleic acid sequence may be $(N)_m$, where N is A, T, C or G, or A, U, C or G, and m is an integer of 1 to 150.

The guide nucleic acid may be two or more continuous nucleic acid sequences.

For example, the two or more continuous nucleic acid sequences may be $(N)_m$ and $(N)_o$, where N represents A, T, C or G, or A, U, C or G, m and o are an integer of 1 to 150, and may be the same as or different from each other.

The guide nucleic acid may include one or more domains.

The domain may be a functional domain such as a guide domain, a first complementary domain, a linker domain, a second complementary domain, a proximal domain, or a tail domain, but the present invention is not limited thereto.

Here, one guide nucleic acid may have two or more functional domains. Here, the two or more functional domains may be different from each other. Alternatively, two or more functional domains included in one guide nucleic acid may be the same. For example, one guide nucleic acid may have two or more proximal domains, and as another example, one guide nucleic acid may have two or more tail domains. However, the expression "functional domains included in one guide nucleic acid are the same" does not mean that the sequences of two functional domains are the same, and when these domains functionally perform the same function even with different sequences, they can be considered to be the same domains.

The domains will be described below.

i) Guide Domain

The term "guide domain" is a domain having a complementary guide sequence which is able to form a complementary bond with a target sequence on a target gene or nucleic acid, and serves to specifically interact with the target gene or nucleic acid. For example, a guide domain may perform a function of inducing a guide nucleic acid-editor protein complex to a location having a specific nucleotide sequence of a target gene or nucleic acid.

The guide domain may be a sequence of 10 to 35 bases

In an example, the guide domain may be a sequence of 10 to 35, 15 to 35, 20 to 35, 25 to 35, 30 to 35 bases.

In another example, the guide domain may be a sequence of 15 to 20, 20 to 25, 25 to 30, 30 to 35 bases.

The guide domain may have a guide sequence.

The guide sequence may be a nucleic acid sequence complementary to the target sequence on the target gene or nucleic acid, which has, for example, at least 50%, 55%, 60%, 65%, 70%, 75%, 80%, 85%, 90% or 95% or more complementarity or complete complementarity.

The guide sequence may be a 10 to 25-base sequence.

In an example, the guide sequence may be a 10 to 25, 15 to 25, 20 to 25, 20 to 50, 25 to 50, 30 to 50, 35 to 50, 40 to 50, or 45 to 50-base sequence.

In another example, the guide sequence may be a 10 to 15, 15 to 20, 20 to 25-base sequence.

In addition, the guide domain may include an additional base sequence.

The additional base sequence may be utilized to improve or degrade the function of the guide domain.

The additional base sequence may be utilized to improve or degrade the function of the guide sequence.

The additional base sequence may be a 1 to 10-base sequence.

In one example, the additional base sequence may be a 2 to 10, 4 to 10, 6 to 10, 8 to 10-base sequence.

In another example, the additional base sequence may be a 1 to 3, 3 to 6, 7 to 10-base sequence.

As a specific example, the additional base sequence may be a 1, 2, 3, 4, 5, 6, 7, 8, 9, 10-base sequence.

In one example, the additional nucleotide sequence may be 1-base sequence G (guanine) or 2-base sequence GG.

The additional base sequence may be located at the 5'end of the guide sequence.

The additional base sequence may be located at the 3'end of the guide sequence.

ii) First Complementary Domain

The term "first complementary domain" is a nucleic acid sequence including a nucleic acid sequence complementary to a second complementary domain, and has enough complementarity so as to form a double strand with the second complementary domain. In one example, the first complementary domain may be a nucleic acid sequence complementary to the second complementary domain, which has, for example, at least 50%, 55%, 60%, 65%, 70%, 75%, 80%, 85%, 90% or 95% or more complementarity or complete complementarity/

The first complementary domain may form a double strand by a complementary bond with a second complementary domain. Here, the formed double strand may serve to form a guide nucleic acid-editor protein complex by an interaction with some amino acids of the editor protein.

The first complementary domain may be a 5 to 35-base sequence.

In an example, the first complementary domain may be a 5 to 35, 10 to 35, 15 to 35, 20 to 35, 25 to 35, or 30 to 35-base sequence.

In another example, the first complementary domain may be a 1 to 5, 5 to 10, 10 to 15, 15 to 20, 20 to 25, 25 to 30 or 30 to 35-base sequence.

iii) Linker Domain

The term "linker domain" is a nucleic acid sequence connecting two or more domains, which are two or more identical or different domains. The linker domain may be connected with two or more domains by covalent bonding or non-covalent bonding, or may connect two or more domains by covalent bonding or non-covalent bonding.

The linker domain may be a 1 to 30-base sequence.

In one example, the linker domain may be a 1 to 5, 5 to 10, 10 to 15, 15 to 20, 20 to 25, or 25 to 30-base sequence.

In another example, the linker domain may be a 1 to 30, 5 to 30, 10 to 30, 15 to 30, 20 to 30, or 25 to 30-base sequence.

iv) Second Complementary Domain

The term "Second complementary domain" is a nucleic acid sequence including a nucleic acid sequence complementary to a First complementary domain, and has enough complementarity so as to form a double strand with the first complementary domain.

In one example, the second complementary domain may be a nucleic acid sequence complementary to the first complementary domain, which has, for example, at least 50%, 55%, 60%, 65%, 70%, 75%, 80%, 85%, 90% or 95% or more complementarity or complete complementarity.

The second complementary domain may form a double strand by a complementary bond with the first complementary domain. Here, the formed double strand may serve to form a guide nucleic acid-editor protein complex by an interaction with some amino acids of the editor protein.

The second complementary domain may have a base sequence complementary to the first complementary domain, and a base sequence having no complementarity to the first complementary domain, for example, a base sequence not forming a double strand with the first complementary domain, and may have a longer base sequence than the first complementary domain.

The second complementary domain may have a 5 to 35-base sequence.

In an example, the second complementary domain may be a 1 to 35, 5 to 35, 10 to 35, 15 to 35, 20 to 35, 25 to 35, or 30 to 35-base sequence.

In another example, the second complementary domain may be a 1 to 5, 5 to 10, 10 to 15, 15 to 20, 20 to 25, 25 to 30, or 30 to 35-base sequence.

v) Proximal Domain

The term "proximal domain" is a nucleic acid sequence located adjacent to the second complementary domain.

The proximal domain may have a complementary base sequence therein, and may be formed in a double strand due to a complementary base sequence.

The proximal domain may be a 1 to 20-base sequence.

In one example, the proximal domain may be a 1 to 20, 5 to 20, 10 to 20 or 15 to 20-base sequence.

In another example, the proximal domain may be a 1 to 5, 5 to 10, 10 to 15 or 15 to 20-base sequence.

vi) Tail Domain

The term "tail domain" is a nucleic acid sequence located at one or more ends of the both ends of the guide nucleic acid.

The tail domain may have a complementary base sequence therein, and may be formed in a double strand due to a complementary base sequence.

The tail domain may be a 1 to 50-base sequence.

In an example, the tail domain may be a 5 to 50, 10 to 50, 15 to 50, 20 to 50, 25 to 50, 30 to 50, 35 to 50, 40 to 50, or 45 to 50-base sequence.

In another example, the tail domain may be a 1 to 5, 5 to 10, 10 to 15, 15 to 20, 20 to 25, 25 to 30, 30 to 35, 35 to 40, 40 to 45, or 45 to 50-base sequence.

Meanwhile, a part or all of the nucleic acid sequences included in the domains, that is, the guide domain, the first complementary domain, the linker domain, the second complementary domain, the proximal domain and the tail domain may selectively or additionally include a chemical modification.

The chemical modification may be, but is not limited to, methylation, acetylation, phosphorylation, phosphorothioate linkage, a locked nucleic acid (LNA), 2'-O-methyl 3'phosphorothioate (MS) or 2'-O-methyl 3'thioPACE (MSP). [285]

The guide nucleic acid includes one or more domains.

The guide nucleic acid may include a guide domain.

The guide nucleic acid may include a first complementary domain.

The guide nucleic acid may include a linker domain.

The guide nucleic acid may include a second complementary domain.

The guide nucleic acid may include a proximal domain.

The guide nucleic acid may include a tail domain.

Here, there may be 1, 2, 3, 4, 5, 6 or more domains.

The guide nucleic acid may include 1, 2, 3, 4, 5, 6 or more guide domains.

The guide nucleic acid may include 1, 2, 3, 4, 5, 6 or more first complementary domains.

The guide nucleic acid may include 1, 2, 3, 4, 5, 6 or more linker domains.

The guide nucleic acid may include 1, 2, 3, 4, 5, 6 or more second complementary domains.

The guide nucleic acid may include 1, 2, 3, 4, 5, 6 or more proximal domains.

The guide nucleic acid may include 1, 2, 3, 4, 5, 6 or more tail domains.

Here, in the guide nucleic acid, one type of domain may be duplicated.

The guide nucleic acid may include several domains with or without duplication.

The guide nucleic acid may include the same type of domain. Here, the same type of domain may have the same nucleic acid sequence or different nucleic acid sequences.

The guide nucleic acid may include two types of domains. Here, the two different types of domains may have different nucleic acid sequences or the same nucleic acid sequence.

The guide nucleic acid may include three types of domains. Here, the three different types of domains may have different nucleic acid sequences or the same nucleic acid sequence.

The guide nucleic acid may include four types of domains. Here, the four different types of domains may have different nucleic acid sequences, or the same nucleic acid sequence.

The guide nucleic acid may include five types of domains. Here, the five different types of domains may have different nucleic acid sequences, or the same nucleic acid sequence.

The guide nucleic acid may include six types of domains. Here, the six different types of domains may have different nucleic acid sequences, or the same nucleic acid sequence.

For example, the guide nucleic acid may consist of [guide domain]-[first complementary domain]-[linker domain]-[second complementary domain]-[linker domain]-[guide domain]-[first complementary domain]-[linker domain]-[second complementary domain]. Here, the two guide domains may include guide sequences for different or the same targets, the two first complementary domains and the two second complementary domains may have the same or different nucleotide sequences. When the guide domains include guide sequences for different targets, the guide nucleic acids may specifically bind to two different targets, and here, the specific bindings may be performed simultaneously or sequentially. In addition, the linker domains may be cleaved by specific enzymes, and the guide nucleic acids may be divided into two or three parts in the presence of specific enzymes.

In one exemplary embodiment disclosed herein, a guide nucleic acid for manipulating a high-expression secretory gene may be gRNA for manipulating a high-expression secretory gene.

The gRNA may be transcribed in vitro, and particularly, transcribed from an oligonucleotide double strand or a plasmid template, but the present invention is not limited thereto.

The term "gRNA" used herein refers to target DNA-specific RNA, which can form a complex with a Cas protein and guide the Cas protein to target DNA.

The gRNA may include multiple domains. Each domain may have an intra-strand or inter-strand interaction of a three-dimensional form or active form of gRNA.

In one exemplary embodiment, single-stranded gRNA may include a guide domain in a 5' to 3' direction, for example, a domain having a guide sequence which can form a complementary bond with a target gene or nucleic acid; a first complementary domain; a linker domain; a second complementary domain, which is a domain capable of forming a double-stranded nucleic acid with the first complementary domain since it has a sequence complementary to the sequence of the first complementary domain; a proximal domain; and selectively, a tail domain.

In another exemplary embodiment, dual gRNA may include a guide domain in a 5' to 3' direction, for example, a first strand including a domain having a guide sequence which can form a complementary bond with a target gene or nucleic acid and a first complementary domain; and a second strand including a second complementary domain, which is a domain capable of forming a double-stranded nucleic acid with the first complementary domain since it has a sequence complementary to the sequence of the first complementary domain, a proximal domain, and selectively a tail domain.

Here, the first strand may be referred to as crRNA, and the second strand may be referred to as tracrRNA. The crRNA may include a guide domain and a first complementary domain, and the tracrRNA may include a second complementary domain, a proximal domain, and selectively a tail domain.

In still another exemplary embodiment, single-stranded gRNA may include a guide domain in a 5' to 3' direction, for example, a domain having a guide sequence which can form a complementary bond with a target gene or nucleic acid; a first complementary domain; and a second complementary domain, which is a second complementary domain, which is a domain capable of forming a double-stranded nucleic acid with the first complementary domain since it has a sequence complementary to the sequence of the first complementary domain.

Here, the first complementary domain may have homology with a naturally-occurring first complementary domain, or may be derived from a naturally-occurring first complementary domain. In addition, the first complementary domain may have a difference in nucleotide sequence of the first complementary domain according to a species existing in nature, may be derived from the first complementary domain including a species existing in nature, or partial or complete homology with the first complementary domain including a species existing in nature.

In one exemplary embodiment, the first complementary domain may have partial, that is, at least 50% or more, or complete homology with a first complementary domain of *Streptococcus pyogenes, Campylobacter jejuni, Streptococcus thermophilus, Streptococcus aureus* or *Neisseria meningitides*, or a first complementary domain derived therefrom.

For example, when the first complementary domain is the first complementary domain of *Streptococcus pyogenes* or a first complementary domain derived therefrom, the first complementary domain may be 5'-GUUUUAGAGCUA-3' (SEQ ID NO: 367) or a base sequence having partial, that is, at least 50% or more, or complete homology with 5'-GUUUUAGAGCUA-3' (SEQ ID NO: 367). Here, the first complementary domain may further include $(X)_n$, resulting in 5'-GUUUUAGAGCUA(X)n-3' (SEQ ID NO: 368). The X may be selected from the group consisting of bases A, T, U and G, and the n may represent the number of bases, which is an integer of 5 to 15. Here, the (X)n may be n repeats of the same base, or a mixture of n bases of A, T, U and G.

In another embodiment, when the first complementary domain is the first complementary domain of *Campylobacter jejuni* or a first complementary domain derived therefrom, the first complementary domain may be 5'-GUUUUAGUCCCUUUUUAAAUUUCUU-3' (SEQ ID NO: 369), or a base sequence having partial, that is, at least 50% or more, or complete homology with 5'-GUUUUAGUCCCUUUUUAAAUUUCUU-3' (SEQ ID NO: 369). Here, the first complementary domain may further include (X)n, resulting in 5'-GUUUUAGUCCCUUUUUAAAUUUCUU(X)n-3' (SEQ ID NO: 370). The X may be selected from the group consisting of bases A, T, U and G, and the n may represent the number of bases, which is an integer of 5 to 15. Here, the (X)n may represent n repeats of the same base, or a mixture of n bases of A, T, U and G.

In another embodiment, the first complementary domain may have partial, that is, at least 50% or more, or complete homology with a first complementary domain of Parcubacteria bacterium (GWC2011 GWC2_44_17), Lachnospiraceae bacterium (MC2017), *Butyrivibrio proteoclasiicus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella bovoculi* (237), *Smiihella* sp. (SC_KO8D17), *Leptospira inadai*, Lachnospiraceae bacterium (MA2020), *Francisella novicida* (U112), *Candidatus Methanoplasma termitum* or *Eubacterium eligens*, or a first complementary domain derived therefrom.

For example, when the first complementary domain is the first complementary domain of Parcubacteria bacterium or a first complementary domain derived therefrom, the first complementary domain may be 5'-UUUGUAGAU-3' (SEQ ID NO: 371), or a base sequence having partial, that is, at least 50% or more homology with 5'-UUUGUAGAU-3' (SEQ ID NO: 371). Here, the first complementary domain may further include $(X)_n$, resulting in 5'-(X)nUUUGUAGAU-3' (SEQ ID NO: 372). The X may be selected from the group consisting of bases A, T, U and G, and the n may represent the number of bases, which is an integer of 1 to 5. Here, the $(X)_n$ may represent n repeats of the same base, or a mixture of n bases of A, T, U and G.

Here, the linker domain may be a nucleotide sequence serving to link the first complementary domain with the second complementary domain.

The linker domain may be covalent bonded or non-covalent bonded to each of the first complementary domain and the second complementary domain.

The linker domain may covalently or non-covalently link the first complementary domain with the second complementary domain.

The linker domain is suitable for the use in a single-stranded gRNA molecule, and may form a covalent or non-covalent bond with the first strand and the second strand of dual gRNA, or used to produce single-stranded gRNA by a covalent or non-covalent linkage between first and second strands.

The linker domain may form a covalent or non-covalent bond with crRNA and tracrRNA of dual gRNA, or may be used to produce single-stranded gRNA by a covalent or non-covalent linkage between crRNA and tracrRNA.

Here, the second complementary domain may have homology with a naturally-occurring second complementary domain, or may be derived from a naturally-occurring second complementary domain. In addition, the second complementary domain may have a difference in nucleotide sequence of a second complementary domain according to a species existing in nature, may be derived from a second complementary domain included in a species existing in nature, or may have partial or complete homology with a second complementary domain included in a species existing in nature.

In an exemplary embodiment, the second complementary domain may have partial, that is, at least 50% or more, or complete homology with a second complementary domain of *Streptococcus pyogenes, Campylobacter jejuni, Streptococcus thermophilus, Streptococcus aureus* or *Neisseria meningitides*, or a second complementary domain derived therefrom.

For example, when the second complementary domain is a second complementary domain of *Streptococcus pyogenes* or a second complementary domain derived therefrom, the second complementary domain may be 5'-UAGCAAGUUAAAAU-3' (SEQ ID NO: 373), or a base sequence having partial, that is, at least 50% or more homology with 5'-UAGCAAGUUAAAAU-3' (SEQ ID NO: 373) (a base sequence forming a double strand with the first complementary domain is underlined). Here, the second complementary domain may further include $(X)_n$ and/or $(X)_m$, resulting in 5'-$(X)_n$ UAGCAAGUUAAAAU$(X)_m$-3' (SEQ ID NO: 374). The X may be selected from the group consisting of bases A, T, U and G, and each of the n and m may represent the number of bases, in which the n may be an integer of 1 to 15, and the m may be an integer of 1 to 6. Here, the $(X)_n$ may represent n repeats of the same base, or a mixture of n bases of A, T, U and G. In addition, $(X)_m$ may represent m repeats of the same base, or a mixture of m bases of A, T, U and G.

In another example, when the second complementary domain is the second complementary domain of *Campylobacter jejuni* or a second complementary domain derived therefrom, the second complementary domain may be 5'-AAGAAAUUUAAAAAGGGACUAAAAU-3' (SEQ ID NO: 375), or a base sequence having partial, that is, at least 50% or more homology with 5'-AAGAAAUUUAAAAAGGGACUAAAAU-3' (SEQ ID NO: 375) (a base sequence forming a double strand with the first complementary domain is underlined). Here, the second complementary domain may further include $(X)_n$ and/or $(X)_m$, resulting in 5'-$(X)$nAAGAAAUUUAAAAAGGGACUAAAAU$(X)$m-3' (SEQ ID NO: 376). The X may be selected from the group consisting of bases A, T, U and G, and each of the n and m may represent the number of bases, in which the n may be an integer of 1 to 15, and the m may be an integer of 1 to 6. Here, $(X)_n$ may represent n repeats of the same base, or a mixture of n bases of A, T, U and G. In addition, $(X)_m$ may represent m repeats of the same base, or a mixture of m bases of A, T, U and G.

In another embodiment, the second complementary domain may have partial, that is, at least 50% or more, or complete homology with a first complementary domain of Parcubacteria bacterium (GWC2011_GWC2_44_17), Lachnospiraceae bacterium (MC2017), *Butyrivibrio* proteoclasticus, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella bovoculi* (237), *Smiihella* sp. (SC_KO8D17), *Leptospira inadai*, Lachnospiraceae bacterium (MA2020), *Francisella novicida* (U112), *Candidatus Methanoplasma termitum* or *Eubacterium eligens*, or a second complementary domain derived therefrom.

For example, when the second complementary domain is a second complementary domain of Parcubacteria bacterium or a second complementary domain derived therefrom, the second complementary domain may be 5'-AAAUUUC-UACU-3' (SEQ ID NO: 377), or a base sequence having partial, that is, at least 50% or more homology with 5'-AAAUUUCUACU-3' (SEQ ID NO: 377) (a base sequence forming a double strand with the first complementary domain is underlined). Here, the second complementary domain may further include $(X)_n$ and/or $(X)_m$, resulting in 5'-$(X)_n$ AAAUUUCUACU$(X)_m$-3' (SEQ ID NO: 378). The X may be selected from the group consisting of bases A, T, U and G, and each of the n and m may represent the number of bases, in which the n may be an integer of 1 to 10, and the m may be an integer of 1 to 6. Here, the $(X)_n$ may represent n repeats of the same base, or a mixture of n bases of A, T, U and G. In addition, the $(X)_m$ may represent m repeats of the same base, or a mixture of m bases of A, T, U and G.

Here, the first complementary domain and the second complementary domain may be complementarily bonded.

The first complementary domain and the second complementary domain may form a double strand by the complementary bonding.

The formed double strand may interact with a CRISPR enzyme.

Selectively, the first complementary domain may include an additional nucleotide sequence which does not form a complementary bond with a second complementary domain of a second strand.

Here, the additional nucleotide sequence may be a sequence of 1 to 15 nucleotides. For example, the additional nucleotide sequence may be a sequence of 1 to 5 nucleotides, 5 to 10 nucleotides, or 10 to 15 nucleotides.

Here, the proximal domain may be located at the 3'end direction of the second complementary domain.

In addition, the proximal domain may have homology with a natural proximal domain, or may be derived from the natural proximal domain. In addition, the proximal domain may have a difference in base sequence according to a species existing in nature, may be derived from a proximal domain contained in the species existing in nature, or may have partial or complete homology with the proximal domain contained in the species existing in nature.

In an exemplary embodiment, the proximal domain may have partial, that is, at least 50% or more, or complete homology with a proximal domain of *Streptococcus pyogenes*, *Campylobacter jejuni*, *Streptococcus thermophilus*, *Streptococcus aureus* or *Neisseria meningitides*, or a proximal domain derived therefrom.

For example, when the proximal domain is a proximal domain of *Streptococcus pyogenes* or a proximal domain derived therefrom, the proximal domain may be 5'-AAGGC-UAGUCCG-3' (SEQ ID NO: 379), or a base sequence having partial, that is, at least 50% or more homology with 5'-AAGGCUAGUCCG-3' (SEQ ID NO: 379). Here, the proximal domain may further include $(X)_n$, resulting in 5'-AAGGCUAGUCCG$(X)_n$-3' (SEQ ID NO: 380). The X may be selected from the group consisting of bases A, T, U and G, and the n may represent the number of bases, which is an integer of 1 to 15. Here, the $(X)_n$ may represent n repeats of the same base, or a mixture of n bases of A, T, U and G.

In yet another example, when the proximal domain is a proximal domain of *Campylobacter jejuni* or a proximal domain derived therefrom, the proximal domain may be 5'-AAAGAGUUUGC-3' (SEQ ID NO: 381), or a base sequence having at least 50% or more homology with 5'-AAAGAGUUUGC-3' (SEQ ID NO: 381). Here, the proximal domain may further include $(X)_n$, resulting in 5'-AAAGAGUUUGC$(X)_n$-3' (SEQ ID NO: 382). The X may be selected from the group consisting of bases A, T, U and G, and the n may represent the number of bases, which is an integer of 1 to 40. Here, the $(X)_n$ may represent n repeats of the same base, or a mixture of n bases of A, T, U and G.

Here, the tail domain may be selectively added to the 3' end of single-stranded gRNA or the first or second strand of dual gRNA.

In addition, the tail domain may have homology with a natural tail domain, or may be derived from the natural tail domain. In addition, the tail domain may have a difference in base sequence according to a species existing in nature, may be derived from a tail domain contained in a species existing in nature, or may have partial or complete homology with a tail domain contained in a species existing in nature.

In one exemplary embodiment, the tail domain may have partial, that is, at least 50% or more, or complete homology with a tail domain of *Streptococcus pyogenes*, *Campylobacter jejuni*, *Streptococcus thermophilus*, *Streptococcus aureus* or *Neisseria meningitides* or a tail domain derived therefrom.

For example, when the tail domain is a tail domain of *Streptococcus pyogenes* or a tail domain derived therefrom, the tail domain may be 5'-UUAUCAAC-UUGAAAAAGUGGCACCGAGUCGGUGC-3' (SEQ ID NO: 383), or a base sequence having partial, that is, at least 50% or more homology with 5'-UUAUCAAC-UUGAAAAAGUGGCACCGAGUCGGUGC-3' (SEQ ID NO: 383). Here, the tail domain may further include $(X)_n$, resulting in 5'-UUAUCAAC-UUGAAAAAGUGGCACCGAGUCGGUGC$(X)_n$-3' (SEQ ID NO: 384). The X may be selected from the group consisting of bases A, T, U and G, and the n may represent the number of bases, which is an integer of 1 to 15. Here, the $(X)_n$ may represent n repeats of the same base, or a mixture of n bases such as A, T, U and G.

In another example, when the tail domain is a tail domain of *Campylobacter jejuni* or a tail domain derived therefrom, the tail domain may be 5'-GGGACUCUGCGGGGUUA-CAAUCCCCUAAAACCGCUUUU-3' (SEQ ID NO: 385), or a base sequence having partial, that is, at least 50% or more homology with 5'-GGGACUCUGCGGGGUUA-CAAUCCCCUAAAACCGCUUUU-3' (SEQ ID NO: 385). Here, the tail domain may further include $(X)_n$, resulting in 5'-GGGACUCUGCGGGGUUACAAUCCCC-UAAAACCGCUUUU$(X)_n$-3' (SEQ ID NO: 386). The X may be selected from the group consisting of bases A, T, U and G, and the n may represent the number of bases, which is an integer of 1 to 15. Here, the $(X)_n$ may represent n repeats of the same base, or a mixture of n bases of A, T, U and G. [355] In another embodiment, the tail domain may include a 1 to 10-base sequence at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

The gRNA may include a plurality of domains as described above, and therefore, the length of the nucleotide sequence may be regulated according to a domain contained in the gRNA, and interactions may occur in strands in a three-dimensional structure or active form of gRNA or between theses strands due to each domain.

The gRNA may be referred to as single-stranded gRNA (single RNA molecule); or dual gRNA (including more than one, generally two discrete RNA molecules).

Dual gRNA

The dual gRNA consists of a first strand and a second strand.

Here, the first strand may consist of
5'-[guide domain]-[first complementary domain]-3', and
the second strand may consist of
5'-[second complementary domain]-[proximal domain]-3' or
5'-[second complementary domain]-[proximal domain]-[tail domain]-3'.

Here, the first strand may be referred to as crRNA, and the second strand may be referred to as tracrRNA.

In addition, the first strand and the second strand may optionally include an additional base sequence.

In one exemplary embodiment, the first strand may be
5-$(N_{target})$-$(Q)_m$-3'; or
5-$(X)_a$-$(N_{target})$-$(X)_b$-$(Q)_m$-$(X)_c$-3'.

Here, the $N_{target}$ is a base sequence capable of forming a complementary bond with a target sequence on a target gene or nucleic acid, and a base sequence region which may be changed according to a target sequence on a target gene or nucleic acid.

Here, the $(Q)_m$ is a base sequence including the first complementary domain, which is able to form a complementary bond with the second complementary domain of the second strand. The $(Q)_m$ may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Streptococcus pyogenes* or a *Streptococcus pyogenes*-derived first complementary domain, the $(Q)_m$ may be 5'-GUUUUAGAGCUA-3' (SEQ ID NO: 367), or a base sequence having at least 50% or more homology with 5'-GUUUUAGAGCUA-3' (SEQ ID NO: 367).

In another example, when the first complementary domain has partial or complete homology with a first complementary domain of *Campylobacter jejuni* or a *Campylobacter jejuni*-derived first complementary domain, the $(Q)_m$ may be 5'-GUUUUAGUCCC-UUUUUAAAUUUCUU-3' (SEQ ID NO: 369), or a base sequence having at least 50% or more homology with 5'-GUUUUAGUCCCUUUUUAAAUUUCUU-3' (SEQ ID NO: 369).

In still another example, when the first complementary domain has partial or complete homology with a first complementary domain of *Streptococcus thermophilus* or a *Streptococcus thermophilus*-derived first complementary domain, the $(Q)_m$ may be 5'-GUUUUAGAGCUGUGUU-GUUUCG-3' (SEQ ID NO: 387), or a base sequence having at least 50% or more homology with 5'-GUUUUAGAGCU-GUGUUGUUUCG-3' (SEQ ID NO: 387).

In addition, each of the $(X)_a$, $(X)_b$ and $(X)_c$ is selectively an additional base sequence, where the X may be each independently selected from the group consisting of A, U, C and G, and each of the a, b and c may be the number of bases, which is 0 or an integer of 1 to 20.

In one exemplary embodiment, the second strand may be 5'-$(Z)_h$-(P)k-3'; or 5'-(X)d-$(Z)_h$-(X)e-(P)k-(X)f-3'.

In another embodiment, the second strand may be 5'-$(Z)_h$-(P)k-(F)i-3'; or 5'-(X)d-$(Z)_h$-(X)e-(P)k-(X)f-(F)i-3'.

Here, the $(Z)_h$ is a base sequence including a second complementary domain, which is able to form a complementary bond with the first complementary domain of the first strand. The $(Z)_h$ may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of *Streptococcus pyogenes* or a second complementary domain derived therefrom, the $(Z)_h$ may be 5'-UAGCAAGUUAAAAU-3' (SEQ ID NO: 373), or a base sequence having at least 50% or more homology with 5'-UAGCAAGUUAAAAU-3' (SEQ ID NO: 373).

In another example, when the second complementary domain has partial or complete homology with a second complementary domain of *Campylobacter jejuni* or a second complementary domain derived therefrom, the $(Z)_h$ may be 5'-AAGAAAUUUAAAAAGGGACUAAAAU-3' (SEQ ID NO: 375), or a base sequence having at least 50% or more homology with 5'-AAGAAAUUUAAAAAGGGAC-UAAAAU-3' (SEQ ID NO: 375).

In still another example, when the second complementary domain has partial or complete homology with a second complementary domain of *Streptococcus thermophilus* or a second complementary domain derived therefrom, the $(Z)_h$ may be 5'-CGAAACAACACAGCGAGUUAAAAU-3' (SEQ ID NO: 388), or a base sequence having at least 50% or more homology with 5'-CGAAACAACACAGCGAGUUAAAAU-3' (SEQ ID NO: 388).

The (P)k is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of *Streptococcus pyogenes* or a proximal domain derived therefrom, the (P)k may be 5'-AAGGCUAGUCCG-3' (SEQ ID NO: 379), or a base sequence having at least 50% or more homology with 5'-AAGGCUAGUCCG-3' (SEQ ID NO: 379).

In another example, when the proximal domain has partial or complete homology with a proximal domain of *Campylobacter jejuni* or a proximal domain derived therefrom, the (P)k may be 5'-AAAGAGUUUGC-3' (SEQ ID NO: 381), or a base sequence having at least 50% or more homology with 5'-AAAGAGUUUGC-3' (SEQ ID NO: 381).

In still another example, when the proximal domain has partial or complete homology with a proximal domain of *Streptococcus thermophilus* or a proximal domain derived therefrom, the (P)k may be 5'-AAGGCUUAGUCCG-3' (SEQ ID NO: 389), or a base sequence having at least 50% or more homology with 5'-AAGGCUUAGUCCG-3' (SEQ ID NO: 389).

The (F)i may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of *Streptococcus pyogenes* or a tail domain derived therefrom, the (F)i may be 5'-UUAU-CAACUUGAAAAAGUGGCACCGAGUCGGUGC-3' (SEQ ID NO: 383), or a base sequence having at least 50% or more homology with 5'-UUAUCAAC-UUGAAAAAGUGGCACCGAGUCGGUGC-3' (SEQ ID NO: 383).

In another example, when the tail domain has partial or complete homology with a tail domain of *Campylobacter jejuni* or a tail domain derived therefrom, the (F)i may be 5'-GGGACUCUGCGGGGUUACAAUCCCC-UAAAACCGCUUUU-3' (SEQ ID NO: 385), or a base sequence having at least 50% or more homology with 5'-GGGACUCUGCGGGGUUACAAUCCCC-UAAAACCGCUUUU-3' (SEQ ID NO: 385).

In still another example, when the tail domain has partial or complete homology with a tail domain of *Streptococcus thermophilus* or a tail domain derived therefrom, the (F)i may be 5'-UACUCAACUUGAAAAG-GUGGCACCGAUUCGGUGUUUUU-3' (SEQ ID NO: 390), or a base sequence having at least 50% or more homology with 5'-UACUCAACUUGAAAAG-GUGGCACCGAUUCGGUGUUUUU-3' (SEQ ID NO: 390).

In addition, the (F)i may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

In addition, the (X)d, (X)e and (X)f may be base sequences selectively added, where the X may be each independently selected from the group consisting of A, U, C and G, and each of the d, e and f may be the number of bases, which is 0 or an integer of 1 to 20.

Single-Stranded gRNA

Single-stranded gRNA may be classified into two types, a first single-stranded gRNA and a second single-stranded gRNA First Single-Stranded gRNA First, there is the first single-stranded gRNA in which a first strand or a second strand of the dual gRNA is linked by a linker domain.

Specifically, the single-stranded gRNA may consist of

5'-[guide domain]-[first complementary domain]-[linker domain]-[second complementary domain]-3', 5'-[guide domain]-[first complementary domain]-[linker domain]-[second complementary domain]-[proximal domain]-3' or 5'-[guide domain]-[first complementary domain]-[linker domain]-[second complementary domain]-[proximal domain]-[tail domain]-3'.

The first single-stranded gRNA may selectively include an additional nucleotide sequence.

In one exemplary embodiment, the first single-stranded gRNA may be

5'-$(N_{target})$-$(Q)_m$-$(L)_j$-$(Z)_h$-3';

5'-$(N_{target})$-$(Q)_m$-$(L)_j$-$(Z)_h$-$(P)k$-3'; or

5'-$(N_{target})$-$(Q)_m$-$(L)_j$-$(Z)_h$-$(P)k$-$(F)i$-3'.

In another exemplary embodiment, the single-stranded gRNA may be

5-$(X)_a$-$(N_{target})$-$(X)_b$-$(Q)_m$-$(X)_c$-$(L)_j$-$(X)_d$-$(Z)_h$-$(X)_e$-3';

5-$(X)_a$-$(N_{target})$-$(X)_b$-$(Q)_m$-$(X)_c$-$(L)_j$-$(X)_d$-$(Z)_h$-$(X)_e$-$(P)_k$-$(X)_f$-3'; or 5-$(X)_a$-$(N_{target})$-$(X)_b$-$(Q)_m$-$(X)_c$-$(L)_j$-$(X)_d$-$(Z)_h$-$(X)_e$-$(P)_k$-$(X)_f$-$(F)_i$-3'.

Here, the $N_{target}$ is a nucleotide sequence complementary to a partial sequence of any one strand of the double strand of a target gene or nucleic acid, and the $N_{target}$ is a nucleotide sequence site which can be changed according to a target sequence of a target gene or nucleic acid.

The $(Q)_m$ is a nucleotide sequence including a first complementary domain, and includes a nucleotide sequence which can form a complementary bond with a second complementary domain. The $(Q)_m$ may be a sequence having partial or complete homology with a first complementary domain of a species existing in nature, and the nucleotide sequence of the first complementary domain may be changed according to a species from which it is derived. The Q may be each independently selected from the group consisting of A, U, C and G, and the m may be the number of nucleotides, which is an integer of 5 to 35.

For example, when the first complementary domain is the first complementary domain of *Streptococcus pyogenes* or has partial or complete homology with the *Streptococcus pyogenes*-derived first complementary domain, the $(Q)_m$ may be 5'-GUUUUAGAGCUA-3' (SEQ ID NO: 367), or a nucleotide sequence having at least 50% homology with 5'-GUUUUAGAGCUA-3' (SEQ ID NO: 367).

In another example, when the first complementary domain is the first complementary domain of *Campylobacter jejuni* or has partial or complete homology with the *Campylobacter jejuni*-derived first complementary domain, the $(Q)_m$ may be 5'-GUUUUAGUCCC-UUUUUAAAUUUCUU-3' (SEQ ID NO: 369), 5'-GUUUUAGUCCCUU-3', or a nucleotide sequence having at least 50% homology with 5'-GUUUUAGUCCC-UUUUUAAAUUUCUU-3' (SEQ ID NO: 369) or 5'-GUUUUAGUCCCUU-3' (SEQ ID NO: 413).

In still another example, when the first complementary domain is the first complementary domain of *Streptococcus thermophiles* or has partial or complete homology with the *Streptococcus thermophiles*-derived first complementary domain, the $(Q)_m$ may be 5'-GUUUUAGAGCUGUGUU-GUUUCG-3' (SEQ ID NO: 387), or a nucleotide sequence having at least 50% homology with 5'-GUUUUAGAGCU-GUGUUGUUUCG-3' (SEQ ID NO: 387).

In addition, the $(L)_j$ is a nucleotide sequence including a linker domain, and a nucleotide sequence which can produce single-stranded gRNA through linkage of a first complementary domain and a second complementary domain. Here, the L may be each independently selected from the group consisting of A, U, C and G, and the j may be the number of nucleotides, which is an integer of 1 to 30.

The $(Z)_h$ is a nucleotide sequence including the second complementary domain, and includes a nucleotide sequence can form a complementary bond with a first complementary domain. The $(Z)_h$ may be a sequence having partial or complete homology with the second complementary domain of a species existing in nature, and the nucleotide sequence of the second complementary domain may be changed according to a species from which it is derived. The Z may be each independently selected from the group consisting of A, U, C and G, and the h may be the number of nucleotides, which is an integer of 5 to 50.

For example, when the second complementary domain is the second complementary domain of *Streptococcus pyogenes* or has partial or complete homology with the *Streptococcus pyogenes*-derived second complementary domain, the $(Z)_h$ may be 5'-UAGCAAGUUAAAAU-3' (SEQ ID NO: 373), or a nucleotide sequence having at least 50% homology with 5'-UAGCAAGUUAAAAU-3' (SEQ ID NO: 373).

In another example, when the second complementary domain is the second complementary domain of *Campylobacter jejuni* or has partial or complete homology with the *Campylobacter jejuni*-derived second complementary domain, the $(Z)_h$ may be 5'-AAGAAAUUUAAAAAGGGACUAAAAU-3' (SEQ ID NO: 375), 5'-AAGGGACUAAAAU-3', or a nucleotide sequence having at least 50% homology with 5'-AAGAAAUUUAAAAAGGGACUAAAAU-3' (SEQ ID NO: 375) or 5'-AAGGGACUAAAAU-3'.

In still another example, when the second complementary domain is the second complementary domain of *Streptococcus thermophiles* or has partial or complete homology with the *Streptococcus thermophiles*-derived second complementary domain, the $(Z)_h$ may be 5'-CGAAACAACACAGCGAGUUAAAAU-3' (SEQ ID NO: 388), or a nucleotide sequence having at least 50% with 5'-CGAAACAACACAGCGAGUUAAAAU-3' (SEQ ID NO: 388).

The (P)k may be a nucleotide sequence including a proximal domain, and a sequence having partial or complete homology with the proximal domain of a species existing in nature, and the nucleotide sequence of the proximal domain may be changed according to a species from which it is derived. The P may be each independently selected from the group consisting of A, U, C and G, and the k may be the number of nucleotides, which is an integer of 1 to 20.

For example, when the proximal domain is the proximal domain of *Streptococcus pyogenes* or has partial or complete homology with the *Streptococcus pyogenes*-derived proximal domain, the (P)k may be 5'-AAGGCUAGUCCG-3'

(SEQ ID NO: 379), or a nucleotide sequence having at least 50% homology with 5'-AAGGCUAGUCCG-3' (SEQ ID NO: 379).

In another example, when the proximal domain is the proximal domain of *Campylobacter jejuni* or has partial or complete homology with the *Campylobacter jejuni*-derived proximal domain, the (P)k may be 5'-AAAGAGUUUGC-3' (SEQ ID NO: 381), or a nucleotide sequence having at least 50% homology with 5'-AAAGAGUUUGC-3' (SEQ ID NO: 381).

In still another example, when the proximal domain is the proximal domain of *Streptococcus* thermophiles or has partial or complete homology with the *Streptococcus* thermophiles-derived proximal domain, the (P)k may be 5'-AAGGCUUAGUCCG-3' (SEQ ID NO: 389), or a nucleotide sequence having at least 50% homology with 5'-AAGGCUUAGUCCG-3' (SEQ ID NO: 389).

The (F)i may be a nucleotide sequence including a tail domain, and a sequence having partial or complete homology with the tail domain of a species existing in nature, and the nucleotide sequence of the tail domain may be changed according to a species from which it is derived. The F may be each independently selected from the group consisting of A, U, C and G, and the i may be the number of nucleotides, which is an integer of 1 to 50.

For example, when the tail domain is the tail domain of *Streptococcus pyogenes* or has partial or complete homology with the *Streptococcus pyogenes*-derived tail domain, the (F)i may be 5'-UUAUCAAC-UUGAAAAAGUGGCACCGAGUCGGUGC-3' (SEQ ID NO: 383) or a nucleotide sequence having at least 50% homology with 5'-UUAUCAAC-UUGAAAAAGUGGCACCGAGUCGGUGC-3' (SEQ ID NO: 383).

In another example, when the tail domain is the tail domain of *Campylobacter jejuni* or has partial or complete homology with the *Campylobacter jejuni*-derived tail domain, the (F)i may be 5'-GGGACUCUGCGGGGUUA-CAAUCCCCUAAAACCGCUUUU-3' (SEQ ID NO: 385) or a nucleotide sequence having at least 50% homology with 5'-GGGACUCUGCGGGGUUACAAUCCCC-UAAAACCGCUUUU-3' (SEQ ID NO: 385).

In still another example, the tail domain is the tail domain of *Streptococcus* thermophiles or has partial or complete homology with the *Streptococcus* thermophiles-derived tail domain, the (F)i may be 5'-UACUCAACUUGAAAAG-GUGGCACCGAUUCGGUGUUUU-3' (SEQ ID NO: 390) or a nucleotide sequence having at least 50% homology with 5'-UACUCAACUUGAAAAG-GUGGCACCGAUUCGGUGUUUU-3' (SEQ ID NO: 390).

In addition, the (F)i may include a 1 to 10-nucleotide sequence at the 3' end involved in an in vitro or in vivo transcription method.

For example, when a T7 promoter is used for in vitro transcription of gRNA, the tail domain may be an arbitrary nucleotide sequence present at the 3' end of a DNA template. In addition, when a U6 promoter is used for in vivo transcription, the tail domain may be UUUUUU, and when a H1 promoter is used for transcription, the tail domain may be UUUU, and when a pol-III promoter is used, the tail domain may consist of several uracil nucleotides or include nucleotides that can be an alternative.

In addition, the $(X)_a$, $(X)_b$, $(X)_e$, $(X)_d$, $(X)_e$ and $(X)_f$ are nucleotide sequences that can be selectively added, and the X may be each independently selected from the group consisting of A, U, C and G, and the a, b, c, d, e and f are the numbers of nucleotides, which may be 0 or an integer of 1 to 20.

Second Single-Stranded gRNA

Second single-stranded gRNA may be single-stranded gRNA consisting of a guide domain, a first complementary domain and a second complementary domain.

Here, the second single-stranded gRNA may consist of
5'-[second complementary domain]-[first complementary domain]-[guide domain]-3'; or
5'-[second complementary domain]-[linker domain]-[first complementary domain]-[guide domain]-3'.

The second single-stranded gRNA may selectively include an additional nucleotide sequence.

In one exemplary embodiment, the second single-stranded gRNA may be
5'-$(Z)_h$-$(Q)_m$-$(N_{target})$-3'; or
5'-$(X)_a$-$(Z)_h$-$(X)_b$-$(Q)_m$-$(X)_c$-$(N_{target})$-3'.

In another exemplary embodiment, the single-stranded gRNA may be
5'-$(Z)_h$-$(L)_j$-$(Q)_m$-$(N_{target})$-3'; or
5'-$(X)_a$-$(Z)_h$-$(L)_j$-$(Q)_m$-$(X)_c$-$(N_{target})$-3'.

Here, the $N_{target}$ is a nucleotide sequence complementary to a partial sequence of any one strand of the double strand of a target gene or nucleic acid, and the $N_{target}$ is a nucleotide sequence site which can be changed according to a target sequence of a target gene or nucleic acid.

The $(Q)_m$ is a nucleotide sequence including a first complementary domain, and includes a nucleotide sequence that can form a complementary bond with a second complementary domain. The $(Q)_m$ may be a sequence having partial or complete homology with a first complementary domain of a species existing in nature, and the nucleotide sequence of the first complementary domain may be changed according to a species from which it is derived. The Q may be each independently selected from the group consisting of A, U, C and G, and the m may be the number of nucleotides, which is an integer of 5 to 35.

For example, when the first complementary domain is a first complementary domain of Parcubacteria bacterium or has partial or complete homology with the Parcubacteria bacterium-derived first complementary domain, the $(Q)_m$ may be 5'-UUUGUAGAU-3' (SEQ ID NO: 371), or a nucleotide sequence having at least 50% homology with 5'-UUUGUAGAU-3' (SEQ ID NO: 371).

The $(Z)_h$ is a nucleotide sequence including a second complementary domain, and includes a nucleotide sequence that can form a complementary bond with a first complementary domain. The $(Z)_h$ may be a sequence having partial or complete homology with a second complementary domain of a species existing in nature, and the nucleotide sequence of the second complementary domain may be changed according to a species from which it is derived. The Z may be each independently selected from the group consisting of A, U, C and G, and the h may be the number of nucleotides, which is an integer of 5 to 50.

For example, when the second complementary domain is a second complementary domain of Parcubacteria bacterium or has partial or complete homology with the Parcubacteria bacterium-derived second complementary domain, the $(Z)_h$ may be 5'-AAAUUUCUACU-3' (SEQ ID NO: 377), or a nucleotide sequence having at least 50% homology with 5'-AAAUUUCUACU-3' (SEQ ID NO: 377).

In addition, the $(L)_j$ is a nucleotide sequence having a linker domain, and a nucleotide sequence which links the first complementary domain and the second complementary domain. Here, the L may be each independently selected from the group consisting of A, U, C and G, and the j may be the number of nucleotides, which is an integer of 1 to 30.

In addition, the $(X)_a$, $(X)_b$ and $(X)_c$ represent nucleotide sequences, which can be selectively added, and the X may be each independently selected from the group consisting of A, U, C and G, and the a, b and c may be the numbers of nucleotides, each of which is 0 or an integer of 1 to 20.

As an aspect of the disclosure disclosed herein, a guide nucleic acid is gRNA which can be complementarily bound to a target sequence of a high-expression secretory gene.

The high-expression secretory gene is the same as described above.

The gRNA is gRNA which can be bound to an arbitrary sequence selected from high-expression secretory gene in a secretory cell.

The high-expression secretory gene is recognized by a guide nucleic acid, and a target gene or target sequence, which is cleaved by an editor protein.

The "target sequence" refers to a nucleotide sequence present in a target gene or nucleic acid, and specifically, a partial nucleotide sequence of a target region in the target gene or nucleic acid. Here, the "target region" is a site that can be modified by a guide nucleic acid-editor protein in the target gene or nucleic acid.

Hereinafter, the target sequence may be used as a term for information on both nucleotide sequences. For example, in the case of a target gene, the target sequence may mean the sequence information of a transcribed strand of target gene DNA, or the nucleotide sequence information of a non-transcribed strand. In the present specification, a guide nucleic acid to use a target sequence including two aspects is referred to as a "guide nucleic acid for the target sequence."

For example, the target sequence may mean 5'-ATCAT-TGGCAGACTAGTTCG-3' (SEQ ID NO: 391), which is a partial nucleotide sequence (transcribed strand) in a target region of target gene A, or 5'-CGAACTAGTCTGCCAAT-GAT-3' (SEQ ID NO: 392), which is a nucleotide sequence complementary to 5'-ATCATTGGCAGACTAGTTCG-3' (SEQ ID NO: 391) (non-transcribed strand).

The target sequence may be a sequence of 5 to 50 nucleotides.

In an embodiment, the target sequence may be 16 nucleotide sequence, 17 nucleotide sequence, 18 nucleotide sequence, 19 nucleotide sequence, 20 nucleotide sequence, 21 nucleotide sequence, 22 nucleotide sequence, 23 nucleotide sequence, 24 nucleotide sequence, or 25 nucleotide sequence.

The target sequence includes a binding sequence or a non-binding sequence for the guide nucleic acid.

The "binding sequence" for the guide nucleic acid is a nucleotide sequence having partial or complete complementarity with a guide sequence included in a guide domain of the guide nucleic acid, and may complementarily bind to the guide sequence included in a guide domain of the guide nucleic acid. A target sequence and guide nucleic acid-binding sequence is a nucleotide sequence which can be changed according to a target gene or nucleic acid, that is, a subject for gene manipulation or correction, and may be designed in various types according to a target gene or nucleic acid.

The "non-binding sequence" for the guide nucleic acid is a nucleotide sequence having partial or complete homology with a guide sequence included in a guide domain of the guide nucleic acid, and may not complementarily bind to the guide sequence included in the guide domain of the guide nucleic acid. In addition, a non-guide nucleic acid-binding sequence may be a nucleotide sequence having complementarity with a guide nucleic acid-binding sequence, and complementarily bind to the guide nucleic acid-binding sequence.

The guide nucleic acid-binding sequence may be a partial nucleotide sequence of a target sequence, and one nucleotide sequence of nucleotide sequences having two different sequence orders of a target sequence, that is, two nucleotide sequences which can complementarily bind to each other. Here, the non-guide nucleic acid-binding sequence may be a nucleotide sequence, other than the guide nucleic acid-binding sequence of the target sequence.

For example, when 5'-CGAACTAGTCTGCCAATGAT-3' (SEQ ID NO: 392), which is a nucleotide sequence complementary to 5'-ATCATTGGCAGACTAGTTCG-3' (SEQ ID NO: 391), which is a partial nucleotide sequence in a target region of target gene A, is used as a target sequence, a guide nucleic acid-binding sequence may be one of two target sequences, that is, 5'-ATCATTGGCA-GACTAGTTCG-3' (SEQ ID NO: 391) or 5'-CGAACTAGTCTGCCAATGAT-3' (SEQ ID NO: 392). Here, the non-guide nucleic acid-binding sequence may be 5'-CGAACTAGTCTGCCAATGAT-3' (SEQ ID NO: 392) when the guide nucleic acid-binding sequence is 5'-ATCAT-TGGCAGACTAGTTCG-3', (SEQ ID NO: 391) or may be 5'-ATCATTGGCAGACTAGTTCG-3' (SEQ ID NO: 391) when the guide nucleic acid-binding sequence is 5'-CGAACTAGTCTGCCAATGAT-3' (SEQ ID NO: 392).

The guide nucleic acid-binding sequence may be one nucleotide sequence selected from a nucleotide sequence which is the same as a target sequence, that is, a transcribed strand, and a nucleotide sequence which is the same as a non-transcribed strand. Here, the non-guide nucleic acid-binding sequence may be a nucleotide sequence, other than one nucleotide sequence selected from a nucleotide sequence which is the same as the guide nucleic acid-binding sequence of the target sequence, that is, a transcribed strand and a nucleotide sequence which is the same as a non-transcribed strand.

The binding sequence may be the same length as the target sequence.

The non-binding sequence may be the same length as the target sequence or the binding sequence.

The binding sequence may be 5 to 50 nucleotide sequence.

In an embodiment, the binding sequence may be 16 nucleotide sequence, 17 nucleotide sequence, 18 nucleotide sequence, 19 nucleotide sequence, 20 nucleotide sequence, 21 nucleotide sequence, 22 nucleotide sequence, 23 nucleotide sequence, 24 nucleotide sequence, or 25 nucleotide sequence.

The non-binding sequence may be 5 to 50 nucleotide sequence.

In an embodiment, the non-binding sequence may be 16 nucleotide sequence, 17 nucleotide sequence, 18 nucleotide sequence, 19 nucleotide sequence, 20 nucleotide sequence, 21 nucleotide sequence, 22 nucleotide sequence, 23 nucleotide sequence, 24 nucleotide sequence, or 25 nucleotide sequence.

The guide nucleic acid-binding sequence may, partially or completely, complementarily bind to a guide sequence included in a guide domain of the guide nucleic acid, and the length of the guide nucleic acid-binding sequence may be the same as that of the guide sequence.

The guide nucleic acid-binding sequence may be a nucleotide sequence complementary to the guide sequence included in the guide domain of the guide nucleic acid, and for example, an at least 70%, 75%, 80%, 85%, 90% or 95% complementary or fully complementary nucleotide sequence.

In one example, the guide nucleic acid-binding sequence may have or include a sequence of 1 to 8 nucleotides, which is not complementary to the guide sequence included in the guide domain of the guide nucleic acid.

The non-guide nucleic acid-binding sequence may have partial or complete homology with the guide sequence included in the guide domain of the guide nucleic acid, and the length of the non-guide nucleic acid-binding sequence may be the same as that of the guide sequence.

The non-guide nucleic acid-binding sequence may be a nucleotide sequence having homology with the guide sequence included in the guide domain of the guide nucleic acid, and for example, a nucleotide sequence having at least 70%, 75%, 80%, 85%, 90% or 95% or more homology or complete homology.

In one example, the non-guide nucleic acid-binding sequence may have or include a sequence of 1 to 8 nucleotides, which does not have homology with the guide sequence included in the guide domain of the guide nucleic acid.

The non-guide nucleic acid-binding sequence may complementarily bind to the guide nucleic acid-binding sequence, and the non-guide nucleic acid-binding sequence may have the same length as the guide nucleic acid-binding sequence.

The non-guide nucleic acid-binding sequence may be a nucleotide sequence complementary to the guide nucleic acid-binding sequence, and for example, an at least 90% or 95% complementary or fully complementary nucleotide sequence.

In one example, the non-guide nucleic acid-binding sequence may have or include one or two nucleotide sequences, which is not complementary to the guide nucleic acid-binding sequence.

In addition, the guide nucleic acid-binding sequence may be a nucleotide sequence located at a location adjacent to a nucleotide sequence which can be recognized by an editor protein.

In one example, the guide nucleic acid-binding sequence may be a sequence of 5 to 50 consecutive nucleotides, which is adjacent to the 5' end and/or the 3' end of a nucleotide sequence which can be recognized by an editor protein.

In addition, the non-guide nucleic acid-binding sequence may be a nucleotide sequence adjacent to a nucleotide sequence which can be recognized by an editor protein.

In one example, the non-guide nucleic acid-binding sequence may be a sequence of 5 to 50 consecutive nucleotides, which is adjacent to the 5' end and/or the 3' end of a nucleotide sequence which can be recognized by an editor protein.

In an embodiment,

The target sequence may be consecutive 10 to 35 nucleotide sequence located in the promoter region of highly expressed and secretory gene.

The target sequence may be 10 to 35 nucleotide sequence, 15 to 35 nucleotide sequence, 20 to 35 nucleotide sequence, 25 to 35 nucleotide sequence or 30 to 35 nucleotide sequence.

The target sequence may be 10 to 15 nucleotide sequence, 15 to 20 nucleotide sequence, 20 to 25 nucleotide sequence, 25 to 30 nucleotide sequence, or 30 to 35 nucleotide sequence.

In an example, the target sequence may be a consecutive 10 to 25 nucleotide sequence located in the promoter region of HP gene.

In another example, the target sequence may be a consecutive 10 to 25 nucleotide sequence located in the promoter region of APOC3 gene.

In another example, the target sequence may be a consecutive 10 to 25 nucleotide sequence located in the promoter region of the intron of highly expressed and secretory gene.

The target sequence may be 10 to 35 nucleotide sequence, 15 to 35 nucleotide sequence, 20 to 35 nucleotide sequence, 25 to 35 nucleotide sequence or 30 to 35 nucleotide sequence.

The target sequence may be 10 to 15 nucleotide sequence, 15 to 20 nucleotide sequence, 20 to 25 nucleotide sequence, 25 to 30 nucleotide sequence, or 30 to 35 nucleotide sequence.

In an example, the target sequence may be a consecutive 10 to 25 nucleotide sequence located in the intron of HP gene.

In another example, the target sequence may be a consecutive 10 to 25 nucleotide sequence located in the intron of APOC3 gene.

In an example, the target sequence may be a consecutive 10 to 25 nucleotide sequence located in the exon of highly expressed and secretory gene.

The target sequence may be 10 to 35 nucleotide sequence, 15 to 35 nucleotide sequence, 20 to 35 nucleotide sequence, 25 to 35 nucleotide sequence or 30 to 35 nucleotide sequence.

The target sequence may be 10 to 15 nucleotide sequence, 15 to 20 nucleotide sequence, 20 to 25 nucleotide sequence, 25 to 30 nucleotide sequence, or 30 to 35 nucleotide sequence.

In an example, the target sequence may be a consecutive 10 to 25 nucleotide sequence located in the exon of HP gene.

In another example, the target sequence may be a consecutive 10 to 25 nucleotide sequence located in the exon of APOC3 gene.

In an example, the target sequence may be a consecutive 10 to 25 nucleotide sequence located in the enhancer of highly expressed and secretory gene.

The target sequence may be 10 to 35 nucleotide sequence, 15 to 35 nucleotide sequence, 20 to 35 nucleotide sequence, 25 to 35 nucleotide sequence or 30 to 35 nucleotide sequence.

The target sequence may be 10 to 15 nucleotide sequence, 15 to 20 nucleotide sequence, 20 to 25 nucleotide sequence, 25 to 30 nucleotide sequence, or 30 to 35 nucleotide sequence.

In an example, the target sequence may be a consecutive 10 to 25 nucleotide sequence located in the enhancer of HP gene.

In an example, the target sequence may be a consecutive 10 to 25 nucleotide sequence located in the enhancer of APOC3 gene.

The target sequence disclosed herein may be a sequence of 10 to 35 consecutive nucleotides, which is located in an encoded, non-encoded or mixed part of the high-expression secretory gene.

The target sequence may be 10 to 35 nucleotide sequence, 15 to 35 nucleotide sequence, 20 to 35 nucleotide sequence, 25 to 35 nucleotide sequence or 30 to 35 nucleotide sequence.

Alternatively, the target sequence may be 10 to 15 nucleotide sequence, 15 to 20 nucleotide sequence, 20 to 25 nucleotide sequence, 25 to 30 nucleotide sequence, or 30 to 35 nucleotide sequence.

In one example, the target sequence may be a sequence of 10 to 25 consecutive nucleotides, which is located in an encoded, non-encoded or mixed part of the HP gene.

In another example, the target sequence may be a sequence of 10 to 25 consecutive nucleotides, which is located in an encoded, non-encoded or mixed part of the APOC3 gene.

The target sequence disclosed herein may be a sequence of 10 to 35 consecutive nucleotides, which is located in a promoter, an enhancer, 3'UTR, a polyA tail of the high-expression secretory gene, or a mixed part thereof.

The target sequence may be 10 to 35 nucleotide sequence, 15 to 35 nucleotide sequence, 20 to 35 nucleotide sequence, 25 to 35 nucleotide sequence or 30 to 35 nucleotide sequence.

The target sequence may be 10 to 15 nucleotide sequence, 15 to 20 nucleotide sequence, 20 to 25 nucleotide sequence, 25 to 30 nucleotide sequence, or 30 to 35 nucleotide sequence.

In one example, the target sequence may be a sequence of 10 to 25 consecutive nucleotides, which is located in a promoter, an enhancer, 3'UTR or a polyA tail of the HP gene, or a mixed part thereof.

In another example, the target sequence may be a sequence of 10 to 25 consecutive nucleotides, which is located in a promoter, an enhancer, 3'UTR or a polyA tail of the APOC3 gene, or a mixed part thereof.

The target sequence disclosed herein may be a sequence of 10 to 35 consecutive nucleotides, which is located in an exon or an intron of the high-expression secretory gene, or a mixed part thereof.

The target sequence may be 10 to 35 nucleotide sequence, 15 to 35 nucleotide sequence, 20 to 35 nucleotide sequence, 25 to 35 nucleotide sequence or 30 to 35 nucleotide sequence.

The target sequence may be 10 to 15 nucleotide sequence, 15 to 20 nucleotide sequence, 20 to 25 nucleotide sequence, 25 to 30 nucleotide sequence, or 30 to 35 nucleotide sequence.

In one example, the target sequence may be a sequence of 10 to 25 consecutive nucleotides, which is located in an exon or an intron of the HP gene, or a mixed part thereof.

In another example, the target sequence may be a sequence of 10 to 25 consecutive nucleotides, which is located in an exon or an intron of the APOC3 gene, or a mixed part thereof.

The target sequence disclosed herein may be a sequence of 10 to 35 consecutive nucleotides, which includes or is adjacent to a mutant part (e.g., a part different from a wild-type gene) of the high-expression secretory gene.

The target sequence may be 10 to 35 nucleotide sequence, 15 to 35 nucleotide sequence, 20 to 35 nucleotide sequence, 25 to 35 nucleotide sequence or 30 to 35 nucleotide sequence.

The target sequence may be 10 to 15 nucleotide sequence, 15 to 20 nucleotide sequence, 20 to 25 nucleotide sequence, 25 to 30 nucleotide sequence, or 30 to 35 nucleotide sequence.

In one example, the target sequence may be a sequence of 10 to 25 consecutive nucleotides, which includes or is adjacent to a mutant part (e.g., a part different from a wild-type gene) of the HP gene.

In another example, the target sequence may be a sequence of 10 to 25 consecutive nucleotides, which includes or is adjacent to a mutant part (e.g., a part different from a wild-type gene) of the APOC3 gene.

The target sequence disclosed herein may be a sequence of 10 to 35 consecutive nucleotides, which is adjacent to the 5' end and/or the 3' end of a protospacer-adjacent motif (PAM) sequence in the nucleotide sequence of the high-expression secretory gene.

The "protospacer-adjacent motif (PAM) sequence" is a nucleotide sequence which is recognized by an editor protein. Here, the PAM sequence may have a difference in nucleotide sequence according to the type of an editor protein and a species from which it is derived.

The PAM sequence may be, for example, one or more of the following sequences (described in the 5' to 3' direction):
NGG (N is A, T, C, or G);
NNNNRYAC (N is each independently A, T, C or G, R is A or G, and Y is C or T);
NNAGAAW (N is each independently A, T, C or G, and W is A or T);
NNNNGATT (N is each independently A, T, C or G);
NNGRR(T) (N is each independently A, T, C or G, R is A or G); and
TTN (N is A, T, C, or G).

In an example, the target sequence may be a 10 to 35, 15 to 35, 20 to 35, 25 to 35, 30 to 35-base sequence.

In an example, the target sequence may be a 10 to 15, 15 to 20, 20 to 25, 25 to 30, 30 to 35-base sequence.

In one example, the target sequence may be a sequence of 10 to 25 consecutive nucleotides, which is adjacent to the 5' end and/or the 3' end of a PAM sequence in the nucleotide sequence of the HP gene.

In one exemplary embodiment, when a PAM sequence recognized by an editor protein is 5'-NGG-3', 5'-NAG-3' and/or 5'-NGA-3' (N=A, T, G or C; or A, U, G or C), the target sequence may be a sequence of 10 to 25 consecutive nucleotides, which is adjacent to the 5' end and/or the 3' end of the 5'-NGG-3', 5'-NAG-3' and/or 5'-NGA-3' (N=A, T, G or C; or A, U, G or C) sequence in the nucleotide sequence of the HP gene.

In another exemplary embodiment, when a PAM sequence recognized by an editor protein is 5'-NGGNG-3' and/or 5'-NNAGAAW-3' (W=A or T, N=A, T, G or C; or A, U, G or C), the target sequence may be the sequence of 10 to 25 consecutive nucleotides, which is adjacent to the 5' end and/or the 3' end of the 5'-NGGNG-3' and/or 5'-NNAGAAW-3' (W=A or T, N=A, T, G or C; or A, U, G or C) sequence in the nucleotide sequence of the HP gene.

In still another exemplary embodiment, when a PAM sequence recognized by an editor protein is 5'-NNNNGATT-3' and/or 5'-NNNGCTT-3' (N=A, T, G or C; or A, U, G or C), the target sequence may be a sequence of 10 to 25 consecutive nucleotides, which is adjacent to the 5' end and/or the 3' end of the 5'-NNNNGATT-3' and/or 5'-NNNGCTT-3' (N=A, T, G or C; or A, U, G or C) sequence in the nucleotide sequence of the HP gene.

In one exemplary embodiment, when a PAM sequence recognized by an editor protein is 5'-NNNVRYAC-3' (V=G, C or A; R=A or G, Y=C or T, and N=A, T, G or C; or A, U, G or C), the target sequence may be a sequence of 10 to 25 consecutive nucleotides, which is adjacent to the 5' end and/or the 3' end of the 5'-NNNVRYAC-3' (V=G, C or A; R=A or G, Y=C or T, and N=A, T, G or C; or A, U, G or C) sequence in the nucleotide sequence of the HP gene.

In another exemplary embodiment, when a PAM sequence recognized by an editor protein is 5'-NAAR-3'

(R=A or G, N=A, T, G or C; or A, U, G or C), the target sequence may be a sequence of 10 to 25 consecutive nucleotides, which is adjacent to the 5' end and/or the 3' end of the 5'-NAAR-3'(R=A or G, N=A, T, G or C; or A, U, G or C) sequence in the nucleotide sequence of the HP gene.

In still another exemplary embodiment, when a PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a sequence of 10 to 25 consecutive nucleotides, which is adjacent to the 5' end and/or the 3' end of the 5'-NNGRR-3', 5'-NNGRRT-3' and/or 5'-NNGRRV-3' (R=A or G, V=G, C or A, N=A, T, G or C; or A, U, G or C) sequence in the nucleotide sequence of the HP gene.

In one exemplary embodiment, when a PAM sequence recognized by an editor protein is 5'-TTN-3' (N=A, T, G or C; or A, U, G or C), the target sequence may be a sequence of 10 to 25 consecutive nucleotides, which is adjacent to the 5' end and/or the 3' end of the 5'-TTN-3' (N=A, T, G or C; or A, U, G or C) sequence in the nucleotide sequence of the HP gene.

In another example, the target sequence may be a sequence of 10 to 25 consecutive nucleotides, which is adjacent to the 5' end and/or the 3' end of a PAM sequence in the nucleotide sequence of the APOC3 gene.

In one exemplary embodiment, when a PAM sequence recognized by an editor protein is 5'-NGG-3', 5'-NAG-3' and/or 5'-NGA-3' (N=A, T, G or C; or A, U, G or C), the target sequence may be a sequence of 10 to 25 consecutive nucleotides, which is adjacent to the 5' end and/or the 3' end of the 5'-NGG-3', 5'-NAG-3' and/or 5'-NGA-3' (N=A, T, G or C; or A, U, G or C) sequence in the nucleotide sequence of the APOC3 gene.

In another exemplary embodiment, when a PAM sequence recognized by an editor protein is 5'-NGGNG-3' and/or 5'-NNAGAAW-3' (W=A or T, N=A, T, G or C; or A, U, G or C), the target sequence may be a sequence of 10 to 25 consecutive nucleotides, which is adjacent to the 5' end and/or the 3' end of the 5'-NGGNG-3' and/or 5'-NNAGAAW-3' (W=A or T, N=A, T, G or C; or A, U, G or C) sequence in the nucleotide sequence of the APOC3 gene.

In still another exemplary embodiment, when a PAM sequence recognized by an editor protein is 5'-NNNNGATT-3' and/or 5'-NNNGCTT-3' (N=A, T, G or C; or A, U, G or C), the target sequence may be a sequence of 10 to 25 consecutive nucleotides, which is adjacent to the 5' end and/or the 3' end of the 5'-NNNNGATT-3' and/or 5'-NNNGCTT-3' (N=A, T, G or C; or A, U, G or C) sequence in the nucleotide sequence of the APOC3 gene.

In one exemplary embodiment, when a PAM sequence recognized by an editor protein is 5'-NNNVRYAC-3' (V=G, C or A; R=A or G, Y=C or T, N=A, T, G or C; or A, U, G or C), the target sequence may be a sequence of 10 to 25 consecutive nucleotides, which is adjacent to the 5' end and/or the 3' end of the 5'-NNNVRYAC-3' (V=G, C or A; R=A or G, Y=C or T, N=A, T, G or C; or A, U, G or C) sequence in the nucleotide sequence of the APOC3 gene.

In another exemplary embodiment, when a PAM sequence recognized by an editor protein is 5'-NAAR-3' (R=A or G, N=A, T, G or C; or A, U, G or C), the target sequence may be a sequence of 10 to 25 consecutive nucleotides, which is adjacent to the 5' end and/or the 3' end of the 5'-NAAR-3'(R=A or G, N=A, T, G or C; or A, U, G or C) sequence in the nucleotide sequence of the APOC3 gene.

In still another exemplary embodiment, when a PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a sequence of 10 to 25 consecutive nucleotides, which is adjacent to the 5' end and/or the 3' end of the 5'-NNGRR-3', 5'-NNGRRT-3' and/or 5'-NNGRRV-3' (R=A or G, V=G, C or A, N=A, T, G or C; or A, U, G or C) sequence in the nucleotide sequence of the APOC3 gene.

In one exemplary embodiment, when a PAM sequence recognized by an editor protein is 5'-TTN-3' (N=A, T, G or C; or A, U, G or C), the target sequence may be a sequence of 10 to 25 consecutive nucleotides, which is adjacent to the 5' end and/or the 3' end of the 5'-TTN-3' (N=A, T, G or C; or A, U, G or C) sequence in the nucleotide sequence of the APOC3 gene.

Hereinafter, examples of the target sequences which can be used in one exemplary embodiment disclosed herein were summarized in the following table, and the target sequences shown in the following table are the non-guide nucleic acid-binding sequences, and from the disclosed sequences, complementary sequences, that is, the guide nucleic acid-binding sequences, can be expected.

TABLE 1

The target sequence of HP gene and APOC3 gene

| Target gene | DNA Target sequence | SEQ ID NO. |
| --- | --- | --- |
| HP gene | AAAGAGGAAAATATCTGCTAAT | 1 |
| | AAGGCACTTAGATCTTATAAAA | 2 |
| | TTCTATTAAAATAGTTTCTAGG | 3 |
| | CTCACTAACAAATGCCAACCAT | 4 |
| | TTAGTGAGATGGTGAACTGGCA | 5 |
| | AGGTGAATTATTATAAAATACT | 6 |
| | GGAAAATATCAAGAAGTAGAGG | 7 |
| | CTCCAGGAAAGAGAAACCTCCC | 8 |
| | GCATTCAGGAAAGTACATTGGC | 9 |
| | GAAATTGCCCCCACACCTGCCC | 10 |
| | AAGAAATTGCCCCCACACCTGC | 11 |
| | TCAAAAATGTAACCTGAAGGAA | 12 |
| | TAGCAGATATTTTCCTCTTTAA | 13 |
| | ATGTGTTACTATTAGTCTTCCT | 14 |
| | ATGTACAATAAGGAAGACTAAT | 15 |
| | ACACAATTAATTGACTAGTACC | 16 |
| | ACAATTAATTGACTAGTACCTG | 17 |
| | AATTAATTGACTAGTACCTGGG | 18 |
| | ATCCCAGGTATTAGTGTGTATC | 19 |
| | TTGACTAGTACCTGGGATACAC | 20 |
| | ACCTGGGATACACACTAATACC | 21 |
| | TAATACCTGGGATACATCTAAT | 22 |
| | ATTTCCTAAAGGTGAATTATTA | 23 |
| | AAGGTTCCTTAAATATATAATT | 24 |

TABLE 1-continued

The target sequence of HP gene and APOC3 gene

| Target gene | DNA Target sequence | SEQ ID NO. |
|---|---|---|
| | TGGAGGGCTCCTGTATTATTGC | 25 |
| | CTCAGTTTCTGGCTGCATTCAG | 26 |
| | CATACACACTTTAGCAGCTTCT | 27 |
| | CCAAGAAATTGCCCCCACACCT | 28 |
| | AGTGCTAGGACCAAGAAATTGC | 29 |
| | GGTGTGGGGGCAATTTCTTGGT | 30 |
| | ATCCACACACACATGCATGTAC | 31 |
| | GCATCCACACACACATGCATGT | 32 |
| | ATGCATCCACACACACATGCAT | 33 |
| | GCATGCATCCACACACACATGC | 34 |
| | ATGCATGCATCCACACACACAT | 35 |
| | TGGAAAGCTAGTCTCCCTGCTT | 36 |
| | AGACCCGAGAGGGTCAGAGTG | 37 |
| | ATCCCACTCTGACCCTCTCGG | 38 |
| | TCTCGGGTCTGCACTCTCTCT | 39 |
| | AGGGCACTGGCTGAATCCACT | 40 |
| | GGTTACATTTTTGACTTTAT | 41 |
| | CTGGGATACACACTAATACC | 42 |
| | GCAAGTAGTGCCCGAATGGT | 43 |
| | TTGTTAGTGAGATGGTGAAC | 44 |
| | GAACTGGCAGACGGCACCTG | 45 |
| | AACTGGCAGACGGCACCTGT | 46 |
| | CTCAGACACCGCAAAGATAG | 47 |
| | CACTATCTTTGCGGTGTCTG | 48 |
| | ACTATCTTTGCGGTGTCTGA | 49 |
| | ATCTTTGCGGTGTCTGAGGG | 50 |
| | AGAAAGGCACATAGGTGGAG | 51 |
| | GCAGAAATAGAACAAAGAAA | 52 |
| | AGAACAAAGAAACGGGCAAA | 53 |
| | GAACAAAGAAACGGGCAAAT | 54 |
| | CAGGAGTGTCTTTTTCCTTC | 55 |
| | AAGTCAAAAATGTAACCTGA | 56 |
| | GTTACATTTTTGACTTTATA | 57 |
| | GATGCCAGGAAGCCTACCAC | 58 |
| | GGATGCCAGGAAGCCTACCA | 59 |
| | ATAAATATACTCAGGATGCC | 60 |
| | ATCTGCTAATAAATATACTC | 61 |
| | CTTATTGTACATTTTTAAAG | 62 |
| | CTCTTTAAAAATGTACAATA | 63 |
| | ACAATTAATTGACTAGTACC | 64 |
| | CAATTAATTGACTAGTACCT | 65 |
| | CAGGTATTAGTGTGTATCCC | 66 |
| | TGGGATACACACTAATACCT | 67 |
| | GCCTTAATTAGATGTATCCC | 68 |
| | ACCTGGGATACATCTAATTA | 69 |
| | AGTTTCTAGGCCAGACACGG | 70 |
| | AATAGTTTCTAGGCCAGACA | 71 |
| | AGAAGCAAGTAGTGCCCGAA | 72 |
| | CTAACAAATGCCAACCATTC | 73 |
| | ACTAACAAATGCCAACCATT | 74 |
| | GTTGGCATTTGTTAGTGAGA | 75 |
| | TGAGATGGTGAACTGGCAGA | 76 |
| | GGCCATGGGCATTGACCCAC | 77 |
| | CACCTGTGGGTCAATGCCCA | 78 |
| | AAAAGCAGGACGGTGGCCAT | 79 |
| | CAAAAGCAGGACGGTGGCCA | 80 |
| | GGTGTCCAAAAGCAGGACGG | 81 |
| | ACTGGTGTCCAAAAGCAGGA | 82 |
| | CATGGCCACCGTCCTGCTTT | 83 |
| | GAGAACTGGTGTCCAAAAGC | 84 |
| | TTGGACACCAGTTCTCTTCC | 85 |
| | TGAAACCCCAAAATGCCAGA | 86 |
| | AATAATTCACCTTTAGGAAA | 87 |
| | TTTCAGATACCATTTCCTAA | 88 |
| | TTTTATAATAATTCACCTTT | 89 |
| | ATATATAATTTTAAACACGT | 90 |
| | AATATATAATTTTAAACACG | 91 |
| | TGTTTAAAATTATATATTTA | 92 |
| | TTGATATTTTCCGTAATAAA | 93 |
| | ATTTAAGGAACCTTTTATTA | 94 |
| | CGGAAAATATCAAGAAGTAG | 95 |
| | AACTCAGAGATGGGAACTTT | 96 |
| | TAACTCAGAGATGGGAACTT | 97 |
| | AATGTAGATAACTCAGAGAT | 98 |
| | AAATGTAGATAACTCAGAGA | 99 |
| | TTTTATTACCACTATCTTTG | 100 |

TABLE 1-continued

The target sequence of HP gene and APOC3 gene

| Target gene | DNA Target sequence | SEQ ID NO. |
|---|---|---|
| | CAATAATACAGGAGCCCTCC | 101 |
| | AAGTACATTGGCAATAATAC | 102 |
| | CTGCATTCAGGAAAGTACAT | 103 |
| | CTCAGTTTCTGGCTGCATTC | 104 |
| | GGAGGGGTGGGCTCAGTTTC | 105 |
| | AGGCACATAGGTGGAGGGGT | 106 |
| | AAGGCACATAGGTGGAGGGG | 107 |
| | TAGAAAGGCACATAGGTGGA | 108 |
| | ATAGAAAGGCACATAGGTGG | 109 |
| | GGGATAGAAAGGCACATAGG | 110 |
| | AGAGGGATAGAAAGGCACAT | 111 |
| | GCTTCTGCAGAATTCCCAGC | 112 |
| | CCAGCAAGCCCTGTCCTGCT | 113 |
| | TCCAGCAAGCCCTGTCCTGC | 114 |
| | TGCAGAATTCCCAGCAGGAC | 115 |
| | GCAGAATTCCCAGCAGGACA | 116 |
| | CCCAGCAGGACAGGGCTTGC | 117 |
| | GACAGGGCTTGCTGGAAGCT | 118 |
| | AGAAGCTGCTAAAGTGTGTA | 119 |
| | GAAGCTGCTAAAGTGTGTAT | 120 |
| | CTGCTAAAGTGTGTATGGGC | 121 |
| | AAAGTGTGTATGGGCAGGTG | 122 |
| | AAGTGTGTATGGGCAGGTGT | 123 |
| | AGTGTGTATGGGCAGGTGTG | 124 |
| | GTGTGTATGGGCAGGTGTGG | 125 |
| | CAGGTGTGGGGGCAATTTCT | 126 |
| | AGTCGATATATGGAAGTGCT | 127 |
| | CAGAAAAGAAAGTCGATATA | 128 |
| | CATATATCGACTTTCTTTTC | 129 |
| | TTTCTTTTCTGGCTGCTAAG | 130 |
| | TTCTTTTCTGGCTGCTAAGT | 131 |
| | TTTTCTGGCTGCTAAGTGGG | 132 |
| | ACTGCAGAGAGAAGACAAGG | 133 |
| | GGCACTGCAGAGAGAAGACA | 134 |
| | TGAAGGAAAAAGACACTCCT | 135 |
| | AGGTTACATTTTGACTTTA | 136 |
| | GTGGTAGGCTTCCTGGCATC | 137 |
| | TATCTGCTAATAAATATACT | 138 |
| | GAAGACTAATAGTAACACAT | 139 |
| | ACAATTAATTGACTAGTACC | 140 |
| | CTGGGATACACACTAATACC | 141 |
| | TTAATAGAAGCAAGTAGTGC | 142 |
| | TGAACTGGCAGACGGCACCT | 143 |
| | TCAGATACCATTTCCTAAAG | 144 |
| | AAATATATAATTTTAAACAC | 145 |
| | CGGAAAATATCAAGAAGTAG | 146 |
| | TAAGCCCAAAGTTCCCATCT | 147 |
| | ATTATTGCCAATGTACTTTC | 148 |
| | ATAGAAAGGCACATAGGTGG | 149 |
| | CCAGCAAGCCCTGTCCTGCT | 150 |
| | TTTTCTGGCTGCTAAGTGGG | 151 |
| | GTGTGTACATGCATGTGTGT | 152 |
| | ACTGCAGAGAGAAGACAAGG | 153 |
| APOC3 gene | CCAGCCCAGCCAGCAAGCCTGG | 154 |
| | CTTCAGGTTATGATGAGGGGTG | 155 |
| | GGGAGGGGTGTCACTTGCCCAA | 156 |
| | ACCCCCTGTGTAGCTTTGGGCA | 157 |
| | AAGCCTGAAGAATGAGGGGGGA | 158 |
| | TGGAGAGGGCCAGAAATCACCC | 159 |
| | GAGAGGGCCAGAAATCACCCAA | 160 |
| | GAAAACCCACCAGACTGAACAT | 161 |
| | AAGGAGTAGGGGCCGGCTCCCT | 162 |
| | TGGGGACCTGGGGTGCCCCTCA | 163 |
| | TCCTGCAAGGAAGTGTCCTGTG | 164 |
| | GGAACAGAGGTGCCATGCAGCC | 165 |
| | CAACAAGGAGTACCCGGGGCTG | 166 |
| | GAGCGCCAGGAGGGCAACAACA | 167 |
| | TCTGCTCAGTTCATCCCTAG | 168 |
| | CTGCTCCAGGTAATGCCCTC | 169 |
| | AGAAGCACTTGCTAGAGCTA | 170 |
| | GGGGCACCCGTCCAGCTCCG | 171 |
| | CTTCAGGTTATGATGAGGGG | 172 |
| | GTTCTTCAGGTTATGATGAG | 173 |
| | CCCGGGCCTCCATGTTCTTC | 174 |
| | AGGTTCCCCCCTCATTCTTC | 175 |
| | CCTAAGCCTGAAGAATGAGG | 176 |

TABLE 1-continued

The target sequence of HP gene and APOC3 gene

| Target gene | DNA Target sequence | SEQ ID NO. |
|---|---|---|
| | AGCCCTAAGCCTGAAGAATG | 177 |
| | GGGTAGGACTGGGCTGTCTA | 178 |
| | AGCCCAGTCCTACCCCAGAC | 179 |
| | GGTGATTTCTGGCCCTCTCC | 180 |
| | CGGAGATCAGTCCAGACCGC | 181 |
| | GCGAGGGATCGAGGCCCAAA | 182 |
| | TCCTCTTTCCCCTCCCCAGA | 183 |
| | CCAGGTAATGCCCTCTGGGG | 184 |
| | CTCCTCTTTCCCCTCCCCAG | 185 |
| | CAGGTAATGCCCTCTGGGGA | 186 |
| | AGGTAATGCCCTCTGGGGAG | 187 |
| | GCCCTCTGGGGAGGGAAAG | 188 |
| | CTCTGGGGAGGGAAAGAGG | 189 |
| | TCTGGGGAGGGAAAGAGGA | 190 |
| | GGGAGGGGAAAGAGGAGGGG | 191 |
| | AGGGGAAAGAGGAGGGGAGG | 192 |
| | AGGAGGGGAGGAGGATGAAG | 193 |
| | GGAGGGGAGGAGGATGAAGA | 194 |
| | GAGGGGAGGAGGATGAAGAG | 195 |
| | GGAGGATGAAGAGGGGCAAG | 196 |
| | CTTGCTGGCTGGGCTGGGCA | 197 |
| | GCTTGCTGGCTGGGCTGGGC | 198 |
| | CCAGGCTTGCTGGCTGGGCT | 199 |
| | TCCAGGCTTGCTGGCTGGGC | 200 |
| | CTTCTCCAGGCTTGCTGGCT | 201 |
| | GCTTCTCCAGGCTTGCTGGC | 202 |
| | AAGTGCTTCTCCAGGCTTGC | 203 |
| | CCCAGCCCAGCCAGCAAGCC | 204 |
| | GCTCTAGCAAGTGCTTCTCC | 205 |
| | CCTCCCCAGAGGGCATTACC | 206 |
| | TGCTAGAGCTAAGGAAGCCT | 207 |
| | AGCTAAGGAAGCCTCGGAGC | 208 |
| | TGCTCCAGGTAATGCCCTCT | 209 |
| | AAGGAAGCCTCGGAGCTGGA | 210 |
| | AGGAAGCCTCGGAGCTGGAC | 211 |
| | AGGTTATGATGAGGGTGGG | 212 |
| | CAGGTTATGATGAGGGGTGG | 213 |
| | TCAGGTTATGATGAGGGGTG | 214 |
| | TTCAGGTTATGATGAGGGGT | 215 |
| | GCTCCAGGTAATGCCCTCTG | 216 |
| | TGTTCTTCAGGTTATGATGA | 217 |
| | ATGTTCTTCAGGTTATGATG | 218 |
| | TCATCATAACCTGAAGAACA | 219 |
| | TCATAACCTGAAGAACATGG | 220 |
| | ACCTGAAGAACATGGAGGCC | 221 |
| | CCTGAAGAACATGGAGGCCC | 222 |
| | GAAGAACATGGAGGCCCGGG | 223 |
| | AAGAACATGGAGGCCCGGGA | 224 |
| | AGAACATGGAGGCCCGGGAG | 225 |
| | GGGCAAGTGACACCCCTCCC | 226 |
| | TGGGCAAGTGACACCCCTCC | 227 |
| | CCCACCCCCTGTGTAGCTTT | 228 |
| | CCCCACCCCCTGTGTAGCTT | 229 |
| | TCACTTGCCCAAAGCTACAC | 230 |
| | CACTTGCCCAAAGCTACACA | 231 |
| | ACTTGCCCAAAGCTACACAG | 232 |
| | CTTGCCCAAAGCTACACAGG | 233 |
| | GCCCAAAGCTACACAGGGGG | 234 |
| | CCCAAAGCTACACAGGGGGT | 235 |
| | CCAAAGCTACACAGGGGGTG | 236 |
| | AGCTACACAGGGGGTGGGGC | 237 |
| | ACAGGGGGTGGGGCTGGAAG | 238 |
| | CTGGAAGTGGCTCCAAGTGC | 239 |
| | ATGAGGGGGGAACCTGCACT | 240 |
| | CTAAGCCTGAAGAATGAGGG | 241 |
| | CCCTAAGCCTGAAGAATGAG | 242 |
| | GCCCTAAGCCTGAAGAATGA | 243 |
| | CCCCCTCATTCTTCAGGCTT | 244 |
| | CCCCTCATTCTTCAGGCTTA | 245 |
| | TCATTCTTCAGGCTTAGGGC | 246 |
| | TTCTTCAGGCTTAGGGCTGG | 247 |
| | TCCCTGTCTGGGGTAGGACT | 248 |
| | TTCCCTGTCTGGGGTAGGAC | 249 |
| | TCAGTTTCCCTGTCTGGGGT | 250 |
| | GCCCAGTCCTACCCCAGACA | 251 |
| | AGGCCTCAGTTTCCCTGTCT | 252 |

TABLE 1-continued

The target sequence of HP gene and APOC3 gene

| Target gene | DNA Target sequence | SEQ ID NO. |
|---|---|---|
| | CAGGCCTCAGTTTCCCTGTC | 253 |
| | TACCCCAGACAGGGAAACTG | 254 |
| | GTGTGTCTTTGGGTGATTTC | 255 |
| | CCAACATGCTGTGTGTCTTT | 256 |
| | GCCAACATGCTGTGTGTCTT | 257 |
| | CCCAAAGACACACAGCATGT | 258 |
| | AAGACACACAGCATGTTGGC | 259 |
| | ACACAGCATGTTGGCTGGAC | 260 |
| | AGCATGTTGGCTGGACTGGA | 261 |
| | ACATCAAGGCACCTGCGGTC | 262 |
| | ACTGAACATCAAGGCACCTG | 263 |
| | ACCCACCAGACTGAACATCA | 264 |
| | AGGTGCCTTGATGTTCAGTC | 265 |
| | TGCCTTGATGTTCAGTCTGG | 266 |
| | GCCTTGATGTTCAGTCTGGT | 267 |
| | CCAAAGGGAGGTGGGTGGGA | 268 |
| | AGGCCCAAAGGGAGGTGGGT | 269 |
| | GAGGCCCAAAGGGAGGTGGG | 270 |
| | ATCGAGGCCCAAAGGGAGGT | 271 |
| | GATCGAGGCCCAAAGGGAGG | 272 |
| | CCATCCCACCCACCTCCCTT | 273 |
| | CATCCCACCCACCTCCCTTT | 274 |
| | AGGGATCGAGGCCCAAAGGG | 275 |
| | GGCGAGGGATCGAGGCCCAA | 276 |
| | TGGTGAGGGCGAGGGATCG | 277 |
| | GGGGGACTGGTGAGGGCGA | 278 |
| | AGGGGGACTGGTGAGGGCG | 279 |
| | TCAGAAGGGGACTGGTGAG | 280 |
| | CTCAGAAGGGGACTGGTGA | 281 |
| | TCTCAGAAGGGGACTGGTG | 282 |
| | CGGGCTCTCAGAAGGGGAC | 283 |
| | TAATACGGGCTCTCAGAAGG | 284 |
| | CTAATACGGGCTCTCAGAAG | 285 |
| | GCTAATACGGGCTCTCAGAA | 286 |
| | TGCTAATACGGGCTCTCAGA | 287 |
| | GGCCGGCTCCCTGCTAATAC | 288 |
| | GGGCCGGCTCCCTGCTAATA | 289 |
| | TTCTGAGAGCCCGTATTAGC | 290 |

TABLE 1-continued

The target sequence of HP gene and APOC3 gene

| Target gene | DNA Target sequence | SEQ ID NO. |
|---|---|---|
| | TCTGAGAGCCCGTATTAGCA | 291 |
| | AGCCCGTATTAGCAGGGAGC | 292 |
| | CTGCCAGAAGGAGTAGGGGC | 293 |
| | GGGTCTGCCAGAAGGAGTAG | 294 |
| | TGGGTCTGCCAGAAGGAGTA | 295 |
| | CTGGGTCTGCCAGAAGGAGT | 296 |
| | GAGCCGGCCCCTACTCCTTC | 297 |
| | CCTTAGCTGGGTCTGCCAGA | 298 |
| | CCTTCTGGCAGACCCAGCTA | 299 |
| | CCTAAGGTAGAACCTTAGCT | 300 |
| | CCCTAAGGTAGAACCTTAGC | 301 |
| | CCCAGCTAAGGTTCTACCTT | 302 |
| | CCAGCTAAGGTTCTACCTTA | 303 |
| | CAGCTAAGGTTCTACCTTAG | 304 |
| | GGGAGGTGGCGTGGCCCCTA | 305 |
| | CCCTCCCTGGGGAGGTGGCG | 306 |
| | TGGACCCCTCCCTGGGGAGG | 307 |
| | AGGGGCCACGCCACCTCCCC | 308 |
| | GGGGCCACGCCACCTCCCCA | 309 |
| | CTCTGGACCCCTCCCTGGGG | 310 |
| | GCCACGCCACCTCCCCAGGG | 311 |
| | CCACGCCACCTCCCCAGGGA | 312 |
| | TGCCTCTGGACCCCTCCCTG | 313 |
| | CACGCCACCTCCCCAGGGAG | 314 |
| | ATGCCTCTGGACCCCTCCCT | 315 |
| | CATGCCTCTGGACCCCTCCC | 316 |
| | CTCCCCAGGGAGGGTCCAG | 317 |
| | CAGGGAGGGTCCAGAGGCA | 318 |
| | ACCCCAGGTCCCCATGCCTC | 319 |
| | AGGGAGGGGTCCAGAGGCAT | 320 |
| | GGGAGGGGTCCAGAGGCATG | 321 |
| | GGTCCAGAGGCATGGGACC | 322 |
| | GTCCAGAGGCATGGGACCT | 323 |
| | TCCAGAGGCATGGGACCTG | 324 |
| | TGTCCTGTGAGGGGCACCCC | 325 |
| | GGACCTGGGGTGCCCCTCAC | 326 |
| | GCAAGGAAGTGTCCTGTGAG | 327 |
| | TGCAAGGAAGTGTCCTGTGA | 328 |

TABLE 1-continued

The target sequence of HP gene and APOC3 gene

| Target gene | DNA Target sequence | SEQ ID NO. |
|---|---|---|
| | CTGCAAGGAAGTGTCCTGTG | 329 |
| | CTCACAGGACACTTCCTTGC | 330 |
| | ATGGCACCTCTGTTCCTGCA | 331 |
| | ACACTTCCTTGCAGGAACAG | 332 |
| | GAGGGAAAGAGGAGGGGAG | 333 |
| | TAAGGAAGCCTCGGAGCTGG | 334 |
| | ATGTTCTTCAGGTTATGATG | 335 |
| | GAAGAACATGGAGGCCCGGG | 336 |
| | CACTTGCCCAAAGCTACACA | 337 |
| | TTCCTCCAGCCCTAAGCCTG | 338 |
| | CAGGCCTCAGTTTCCCTGTC | 339 |
| | AGCCAACATGCTGTGTGTCT | 340 |
| | GTGCCTTGATGTTCAGTCTG | 341 |
| | GAGGCCCAAAGGGAGGTGGG | 342 |
| | GGATCGAGGCCCAAAGGGAG | 343 |
| | AGGGGACTGGTGAGGGGCG | 344 |
| | CCTTAGCTGGGTCTGCCAGA | 345 |
| | CCCCTAAGGTAGAACCTTAG | 346 |
| | GCCACGCCACCTCCCCAGGG | 347 |
| | GGTCCAGAGGCATGGGGACC | 348 |

In another example, a composition for engineering the highly expressed and secretory gene may include the guide nucleic acid and the editor protein.

For example, the composition may include a guide nucleic acid for the target sequence of one or more genes selected from the group of high-expression secretory genes expressed in the liver; and an editor protein or a nucleic acid encoding an editor protein.

The description related to the high-expression secretory gene is the same as described above.

(1) Editor Protein

The term "editor protein" refers to a peptide, polypeptide or protein which is able to directly bind to or interact with, without direct binding to, a nucleic acid. The editor protein is also conceptually referred to as "artificially engineered nuclease" or GEN (RNA-Guided Endonuclease).

The editor protein may be an enzyme.

The term "enzyme" refers to a protein that contains a domain capable of cleaving a nucleic acid, gene, chromosome or protein.

The enzyme may be a nuclease or restriction enzyme.

The editor protein may include a complete active enzyme.

Here, the "complete active enzyme" refers to an enzyme having the same function as a function of a wild-type enzyme, and for example, the wild-type enzyme cleaving the double strand of DNA has complete enzyme activity of entirely cleaving the double strand of DNA. In still another example, when a partial sequence of an amino acid sequence is deleted or substituted by artificial manipulation of a wild-type enzyme cleaving the double strand of DNA, if the artificially manipulated enzyme variant cleaves the double strand of DNA like a wild-type enzyme, the artificially manipulated enzyme variant may be a fully active enzyme.

In addition, the complete active enzyme includes an enzyme having an improved function compared to the function of the wild-type enzyme, and for example, a specific modification or manipulation type of the wild-type enzyme cleaving the double strand of DNA has full enzyme activity which is improved compared to the wild-type enzyme, that is, activity of cleaving the double strand of DNA.

The editor protein may include an incomplete or partially active enzyme.

Here, the "incomplete or partially active enzyme" means an enzyme having a part of the original wild-type enzyme function of cleaving a nucleic acid, gene or chromosome. For example, a specifically modified or manipulated type of the wild-type enzyme cleaving the double strand of DNA may be a type with a first function or a type with a second function. Here, the first function may be a function of cleaving the first strand of the double strand of DNA, and the second function may be a function of cleaving the second strand of the double strand of DNA. Here, the enzyme with the first function or the enzyme with the second function may be an incomplete or partially active enzyme.

The editor protein may include an inactive enzyme.

Here, the "inactive enzyme" refers to an enzyme in which the function of a wild-type enzyme is completely inactivated. For example, the specifically modified or manipulated type of the wild-type enzyme may be a type in which both of the first and second functions are lost, that is, a type in which both of the first function of cleaving the first strand of the double strand of DNA and the second function of cleaving the second strand of the double strand of DNA are lost. Here, the enzyme losing both of the first and second functions may be an inactive enzyme.

The editor protein may be a fusion protein.

Here, the fusion protein refers to a protein produced by fusing an enzyme with an additional domain, peptide, polypeptide or protein.

The additional domain, peptide, polypeptide or protein may be a functional domain, peptide, polypeptide or protein, which has a function the same as or different from the enzyme.

The fusion protein may include an additional domain, peptide, polypeptide or protein at one or more of an N-terminus of an enzyme or the proximity thereof; a C-terminus of the enzyme or the proximity thereof; the middle region of an enzyme; and a combination thereof.

Here, the functional domain, peptide, polypeptide or protein may be a domain, peptide, polypeptide or protein having methylase activity, demethylase activity, transcription activation activity, transcription repression activity, transcription release factor activity, histone modification activity, RNA cleavage activity or nucleic acid binding activity, or a tag or reporter gene for isolation and purification of a protein (including a peptide), but the present invention is not limited thereto.

The functional domain, peptide, polypeptide or protein may be a deaminase.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) 3-galactosidase, 3-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain, peptide, polypeptide or protein may be a nuclear localization sequence or signal (NLS) or a nuclear export sequence or signal (NES).

The NLS may be NLS of SV40 virus large T-antigen with an amino acid sequence PKKKRKV (SEQ ID NO: 393); NLS derived from nucleoplasmin (e.g., nucleoplasmin bipartite NLS with a sequence KRPAATKKAGQAKKKK (SEQ ID NO: 394)); c-myc NLS with an amino acid sequence PAAKRVKLD (SEQ ID NO: 395) or RQRR-NELKRSP (SEQ ID NO: 396); hRNPA1 M9 NLS with a sequence NQSSNFGPMKGGNFG-GRSSGPYGGGGQYFAKPRNQGGY (SEQ ID NO: 397); an importin-α-derived IBB domain sequence RMRIZFKNKGKDTAELRRRRVEVSVELRKAKKD-EQILKRRNV (SEQ ID NO: 398); myoma T protein sequences VSRKRPRP (SEQ ID NO: 399) and PPK-KARED (SEQ ID NO: 400); human p53 sequence PQPKKKPL (SEQ ID NO: 401); a mouse c-abl IV sequence SALIKKKKKMAP (SEQ ID NO: 402); influenza virus NS1 sequences DRLRR (SEQ ID NO: 403) and PKQKKRK (SEQ ID NO: 404); a hepatitis virus-δ antigen sequence RKLKKKIKKL (SEQ ID NO: 405); a mouse Mx1 protein sequence REKKKFLKRR (SEQ ID NO: 406); a human poly(ADP-ribose) polymerase sequence KRKGDEVDGVDEVAKKKSKK (SEQ ID NO: 407); or steroid hormone receptor (human) glucocorticoid sequence RKCLQAGMNLEARKTKK (SEQ ID NO: 408), but the present invention is not limited thereto.

The additional domain, peptide, polypeptide or protein may be a non-functional domain, peptide, polypeptide or protein, which does not exhibit a specific function. Here, the non-functional domain, peptide, polypeptide or protein may be a domain, peptide, polypeptide or protein, which does not affect the enzyme function.

The fusion protein may be a type in which the non-functional domain, peptide, polypeptide or protein is added to one or more amino termini of an enzyme or the vicinity thereof; a carboxyl terminus of an enzyme or the vicinity thereof; the middle part of the enzyme; or a combination thereof.

The editor protein may be a natural enzyme or fusion protein.

The editor protein may be present in the form of a partially modified natural enzyme or fusion protein.

The editor protein may be an artificially produced enzyme or fusion protein, which does not exist in nature.

The editor protein may be present in the form of a partially modified artificial enzyme or fusion protein, which does not exist in nature.

Here, the modification may be substitution, removal, addition of amino acids contained in the editor protein, or a combination thereof.

In addition, the modification may be substitution, removal, addition of some bases in the base sequence encoding the editor protein, or a combination thereof.

The guide nucleic acid and the editor protein may form a guide nucleic acid-editor protein complex.

The guide nucleic acid-editor protein complex may be formed in vitro.

The guide nucleic acid-editor protein complex may be formed in the cytoplasm in a cell.

The guide nucleic acid-editor protein complex may be formed in the nucleus in a cell.

In the guide nucleic acid-editor protein complex, the editor protein may recognize PAM present in a target gene or nucleotide sequence.

On the guide nucleic acid-editor protein complex, the guide nucleic acid may complementarily bind to the target gene or nucleotide sequence.

When the guide nucleic acid-editor protein complex is bound to the target gene or nucleotide sequence, the target gene or nucleotide sequence may be cleaved or modified by an editor protein of the guide nucleic acid-editor protein complex.

In one aspect of the disclosure disclosed herein, the editor protein may be a CRISPR enzyme.

For example, the composition may include gRNA for the target sequence of one or more genes selected from the group of high-expression secretory genes expressed in the liver; and a CRISPR enzyme or a nucleic acid encoding the CRISPR enzyme.

The description of the gRNA is the same as described above.

The CRISPR enzyme may be a nuclease or restrictive enzyme having a function of cleaving the double strand of a target gene or nucleic acid.

The "CRISPR enzyme" is a major protein component of the CRISPR-Cas system, and refers to a nuclease which is mixed with gRNA or forms a complex to recognize a target sequence and cleave DNA.

The "CRISPR-Cas system" is derived from the acquired immune system that stores the genetic information of bacterial pathogens that have invaded from the outside, and then cleaves the genetic information, and refers to a gene correction system which consists of gRNA artificially manipulating the genetic information to recognize a desired target sequence and a Cas protein recognizing DNA, and thus removes and regulates a gene function.

The Cas protein may form a complex with CRISPR RNA (crRNA) and trans-activating crRNA (tracrRNA), thereby exhibiting an activity thereof.

The Cas protein is used herein as the concept of including all variants serving as an endonuclease or nickase which is activated by cooperation with gRNA, as well as natural proteins. The activated endonuclease or nickase may bring about target DNA cleavage, and gene correction using the same. In addition, the inactivated variants may bring about transcriptional regulation or isolation of desired DNA using the same.

The Cas protein may be a CRISPR enzyme with full activity.

The "fully active CRISPR enzyme" refers to an enzyme having the same function as the original wild-type enzyme function of cleaving a nucleic acid, gene or chromosome. That is, the fully active CRISPR enzyme refers to a state of having both of a function of cleaving a first strand of the double strand of DNA and a second function of cleaving a second strand of the double strand of DNA.

When the artificially manipulated CRISPR enzyme variant is an enzyme that cleaves the double strand of DNA like a wild-type enzyme, the artificially manipulated CRISPR enzyme may also be included in a fully active enzyme.

The artificially manipulated CRISPR enzyme may be an enzyme in which a part of a nucleotide sequence is deleted, substituted or added.

The artificially manipulated CRISPR enzyme may be an enzyme in which one or more amino acids of an amino acid sequence are deleted, substituted or added.

The added modification of the amino acid may be the N-terminus and/or the C terminus of a wild-type enzyme, or an adjacent region thereto. In addition, the modification may be a combination thereof.

The CRISPR enzyme variant may be a fully active enzyme with a function, which is improved compared to the wild-type CRISPR enzyme.

For example, a specifically modified or manipulated type of the wild-type CRISPR enzyme, that is, a CRISPR enzyme variant may cleave a DNA double strand in the vicinity of a certain distance of the DNA double strand to be cleaved or while forming a specific bond with the DNA double strand. Here, the specific bond may be a bond with a DNA nucleotide sequence at a cleavage position of an amino acid at a specific position of the enzyme. In this case, the modified or manipulated type may be a fully-active CRISPR enzyme which has a reduced functional activity compared to the wild-type CRISPR enzyme.

The CRISPR enzyme may be an incomplete or partially active CRISPR enzyme.

The "incomplete or partially active" means a state of having a function of the wild-type CRISPR enzyme, that is, one selected from a first function of cleaving the first strand of the DNA double strand and a second function of cleaving the second strand of the DNA double strand. The CRISPR enzyme in this state may be referred to as an incomplete or partially active CRISPR enzyme. In addition, the incomplete or partially active CRISPR enzyme may be referred to as nickase.

The "nickase" refers to a CRISPR enzyme which is manipulated or modified to cleave only one strand of the double strand of a target gene or nucleic acid, the nickase has nuclease activity of cleaving a single strand, for example, a non-complementary strand or complementary strand with gRNA of a target gene or nucleic acid. Therefore, to cleave the double strand, the nuclease activity of two nickases is needed.

For example, the nickase may have nuclease activity caused by an RuvC domain. That is, the nickase may not include nuclease activity caused by an HNH domain, and therefore, the HNH domain may be manipulated or modified.

The CRISPR enzyme may have helicase activity, that is, a function of unwinding the helical structure of a double-stranded nucleic acid, other than the above-described nuclease activity.

In addition, the CRISPR enzyme may be modified such that the helicase activity of the CRISPR enzyme will be fully active, incomplete or partially active or inactive.

The CRISPR enzyme may be a nucleic acid or polypeptide (or protein) having a sequence encoding the CRISPR enzyme, and is representatively a Type II CRISPR enzyme.

The crystal structure of the type II CRISPR enzyme was determined according to studies on two or more types of natural microbial type II CRISPR enzyme molecules (Jinek et al., Science, 343(6176):1247997, 2014) and studies on *Streptococcus pyogenes* Cas9 (SpCas9) complexed with gRNA (Nishimasu et al., Cell, 156:935-949, 2014; and Anders et al., Nature, 2014, doi: 10.1038/nature13579).

The type II CRISPR enzyme may be Cas9.

The "Cas9" is an enzyme that binds to gRNA to cleave or modify a target sequence or position on a target gene or nucleic acid, and may consist of an HNH domain capable of cleaving a nucleic acid strand complementarily binding to gRNA, the RuvC domain capable of cleaving a nucleic acid strand having a non-complementarily binding to gRNA, an REC domain capable of recognizing a target, and a PI domain capable of recognizing PAM. For specific structural characteristics of Cas9, Hiroshi Nishimasu et al. (2014) Cell 156:935-949 may be referenced.

Here, the RuvC domain shares structural similarity with members of the microorganism family existing in nature having the type II CRISPR enzyme, and cleaves a single strand, for example, a non-complementary strand of a target gene or nucleic acid, that is, a strand not forming a complementary bond with gRNA. The RuvC domain is sometimes referred to as an RuvCI domain, RuvCII domain or RuvCIII domain in the art, and generally called an RuvC I, RuvCII or RuvCIII.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II and III motifs.

The Cas9 may be fully active Cas9 or inactive Cas9.

The inactive Cas9 may include fully inactivated Cas9 and partially inactivated Cas9 (e.g., nickase).

The Cas9 may be Cas9 derived from various microorganisms such as *Streptococcus pyogenes, Streptococcus thermophiles, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor bescii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus* or *Acaryochloris marina.*

The Cas9 may be isolated from a microorganism existing in a natural state or produced unnaturally by a recombinant or synthetic method.

In addition, the CRISPR enzyme may be a Type V CRISPR enzyme.

The type V CRISPR enzyme includes a similar RuvC domain corresponding to the RuvC domain of the type II CRISPR enzyme, and may consist of an Nuc domain, instead of the HNH domain of the type II CRISPR enzyme, REC and WED domains, which recognize a target, and a PI domain recognizing PAM. For specific structural characteristics of the type V CRISPR enzyme, Takashi Yamano et al. (2016) Cell 165:949-962 may be referenced.

The type V CRISPR enzyme may interact with gRNA, thereby forming a gRNA-CRISPR enzyme complex, that is, a CRISPR complex, and may allow a guide sequence to approach a target sequence including a PAM sequence in cooperation with gRNA. Here, the ability of the type V CRISPR enzyme for interaction with a target gene or nucleic acid is dependent on the PAM sequence. [680] The PAM sequence is a sequence present in a target gene or nucleic acid, and may be recognized by the PI domain of the type V CRISPR enzyme. The PAM sequence may vary according to the origin of the type V CRISPR enzyme. That is, there are different PAM sequences which are able to be specifically recognized depending on a species. In one example, the PAM sequence recognized by Cpf1 may be 5'-TTN-3' (N is A, T, C or G).

However, although it has been generally understood that PAM is determined depending on the above-described origin of the enzyme, according to results of studies on mutants of enzymes derived from corresponding origins that are progressing, the PAM may vary.

The Type V CRISPR enzyme may be Cpf1,

The Cpf1 may be derived from *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opituaceae, Tuberibacillus, Bacillus, Brevibacillus, Methylobacterium* or *Acidaminococcus*.

The Cpf1 may consist of an RuvC domain similar and corresponding to the RuvC domain of Cas9, an Nuc domain without the HNH domain of Cas9, an REC domain recognizing a target, a WED domain and a PI domain recognizing PAM. For specific structural characteristics of Cpf1, Takashi Yamano et al. (2016) Cell 165:949-962 may be referenced.

The Cpf1 may be fully active Cpf1 or inactive Cpf1.

The inactive Cpf1 may include fully inactivated Cpf1 and partially inactivated Cpf1 (e.g., nickase).

In the Cpf1 enzyme, one, two or more amino acids of the amino acids present in RuvC, Nuc, WED, REC and/or PI domain(s) may be mutated.

The Cpf1 enzyme may include D917, E1006 or D1255 of the amino acids of FnCpf1; D908, E993 or D1263 of the amino acids of AsCpf1; D832, E925, D947 or D1180 of the amino acids of LbCpf1; or the mutations of one or two or more amino acids in the amino acid group corresponding to each different Cpf1 ortholog.

The CRISPR enzyme of the Cas9 or Cpf1 protein may be isolated from a microorganism existing in nature or non-naturally produced by a recombinant or synthetic method.

The Cas protein or a nucleic acid encoding the same may function in the nucleus.

In addition, the isolated Cas protein may be easily introduced into cells. As an example, the Cas protein may be linked with a cell penetrating peptide or a protein transduction domain. The protein transduction domain may be polyarginine or a HIV-derived TAT protein, but the present invention is not limited thereto. Since various types of cell penetrating peptides or protein transduction domains, other than the above-mentioned types, are known in the art, various examples may be applied to the specification by one of ordinary skill in the art without limitation.

The CRISPR enzyme may be a CRISPR enzyme variant prepared by artificially manipulating or modifying the wild-type CRISPR enzyme.

In one example, the CRISPR enzyme variant may be prepared by substituting, deleting and/or adding at least one amino acid of the amino acid sequence of the wild-type CRISPR enzyme.

The CRISPR enzyme variant may be a CRISPR enzyme variant which is artificially manipulated or modified to modify a function of the wild-type CRISPR enzyme, that is, a first function of cleaving the first strand of the double strand of DNA and the second function of cleaving the second strand of the double strand of DNA.

In addition, the CRISPR enzyme mutant may further include an optionally functional domain, in addition to the innate characteristics of the CRISPR enzyme, and such a CRISPR enzyme mutant may have an additional characteristic in addition to the innate characteristics.

Here, the functional domain may be a domain having methylase activity, demethylase activity, transcription activation activity, transcription repression activity, transcription release factor activity, histone modification activity, RNA cleavage activity or nucleic acid binding activity, or a tag or reporter gene for isolating and purifying a protein (including a peptide), but the present invention is not limited thereto.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

The functional domain, peptide, polypeptide or protein may be a deaminase.

For example, an incomplete or partial CRISPR enzyme may additionally include a cytidine deaminase as a functional domain. In one exemplary embodiment, a cytidine deaminase, for example, apolipoprotein B editing complex 1 (APOBEC1) may be added to SpCas9 nickase, thereby producing a fusion protein. The [SpCas9 nickase]-[APOBEC1] formed thereby may be used in base repair or editing of C into T or U, or G into A.

In another example, an adenine deaminase may be further included in an incomplete or partial CRISPR enzyme as a functional domain. As an exemplary embodiment, fusion proteins may be produced by adding adenine deaminases, for example, TadA variants, ADAR2 variants, ADAT2 variants, etc. to SpCas9 nickase. Since, in the [SpCas9 nickase]-[TadA variant], [SpCas9 nickase]-[ADAR2 variant] or [SpCas9 nickase]-[ADAT2 variant], which is prepared as described above, nucleotide A is modified into inosine, the modified inosine is recognized as nucleotide G by a polymerase such that an effect of substantially performing the nucleotide correction or editing of nucleotide A to G is exhibited, the modified inosine may be used in nucleotide correction or editing of nucleotide A to G, or in nucleotide correction or editing of nucleotide T to C.

In addition, the functional domain may be a nuclear localization sequence or signal (NLS) or a nuclear export sequence or signal (NES).

In one example, the CRISPR enzyme may include one or more NLSs. Here, one or more NLSs may be included at an N-terminus of an CRISPR enzyme or the proximity thereof; a C-terminus of the enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV (SEQ ID NO: 393); NLS from nucleoplasmin (e.g., nucleoplasmin bipartite NLS having the sequence KRPAATKKAGQAKKKK (SEQ ID NO: 394)); c-myc NLS having the amino acid sequence PAAKRVKLD (SEQ ID NO: 395) or RQRR-NELKRSP (SEQ ID NO: 396); hRNPA1 M9 NLS having the sequence NQSSNFGPMKGGNFG-GRSSGPYGGGGQYFAKPRNQGGY (SEQ ID NO: 397); the sequence RMRIZFKNKGKDTAELRRRRVEVS-VELRKAKKDEQILKRRNV (SEQ ID NO: 398) of the IBB domain from importin-α; the sequences VSRKRPRP (SEQ ID NO: 399) and PPKKARED (SEQ ID NO: 400) of a myoma T protein; the sequence PQPKKKPL (SEQ ID NO: 401) of human p53; the sequence SALIKKKKKMAP (SEQ ID NO: 402) of mouse c-abl IV; the sequences DRLRR (SEQ ID NO: 403) and PKQKKRK (SEQ ID NO: 404) of influenza virus NS1; the sequence RKLKKKIKKL (SEQ ID NO: 405) of a hepatitis delta virus antigen; the sequence REKKKFLKRR (SEQ ID NO: 406) of a mouse Mx1 protein; the sequence KRKGDEVDGVDEVAKKKSKK (SEQ ID NO: 407) of a human poly (ADP-ribose) polymerase; or the NLS sequence RKCLQAGMNLEARKTKK (SEQ ID NO: 408), derived from a sequence of a steroid hormone receptor (human) glucocorticoid.

The CRISPR enzyme or CRISPR enzyme mutant described in the present invention may be a polypeptide, protein or nucleic acid having a sequence encoding the same, and may be codon-optimized for a subject to introduce the CRISPR enzyme or CRISPR enzyme mutant.

The term "codon optimization" refers to a process of modifying a nucleotide sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized by optimal gene expression in a given organism based on codon optimization.

The gRNA and the CRISPR enzyme may form a gRNA-CIRSPR enzyme complex.

The "gRNA-CRISPR enzyme complex" refers to a complex formed by the interaction between the gRNA and the CIRSPR enzyme.

The gRNA-CRISPR enzyme complex may be formed in vitro.

The gRNA-CRISPR enzyme complex may be formed in the cytoplasm in a cell.

The gRNA-CRISPR enzyme complex may be formed in the nucleus in a cell.

In the gRNA-CRISPR enzyme complex, the CRISPR enzyme may recognize PAM present in a target gene or nucleotide sequence.

In the gRNA-CRISPR enzyme complex, the gRNA may complementarily bind to a target gene or nucleotide sequence.

When the gRNA-CRISPR enzyme complex binds to a target gene or nucleotide sequence, the gene or nucleotide sequence targeted by the CRISPR enzyme of the gRNA-CRISPR enzyme complex may be cleaved or modified.

In another exemplary embodiment, the CRISPR-Cas system may be present in the form of a ribonucleoprotein (RNP) forming a complex of the gRNA and the CRISPR enzyme.

In one exemplary embodiment of the disclosure disclosed herein, a protein of interest may be expressed by manipulating a high-expression secretory gene.

To express the protein of interest, the composition for manipulating the high-expression secretory gene may further include a donor, in addition to the gRNA and the CRISPR enzyme.

For example, the composition may include a guide nucleic acid for a target sequence of one or more genes selected from the groups of high-expression secretory genes expressed in the liver;

an editor protein or a nucleic acid encoding an editor protein; and a donor including a nucleotide sequence encoding a protein of interest.

The "donor" refers to an exogenous nucleotide containing a sequence required to insert a transgene into a subject. The donor is a molecule containing not only a transgene but also sequences required for recombination and sequences affecting gene transcription and expression.

The donor molecule may be a type of nucleic acid, that is, DNA or RNA.

The donor molecule may be single stranded or double stranded. In some cases, the donor molecule may be a single-stranded oligo nucleotide DNA template (ssODT).

The donor molecule may be in the form of a polynucleotide or protein.

The donor molecule may be linear, branched or cyclic, and have any length.

Here, when a linear donor molecule is introduced, the ends of a donor sequence may be protected by a method known to one of ordinary skill in the art. For example, one or more dideoxynucleotide residues may be added to the 3' end of the formed molecule, and a self-complementary oligonucleotide may bind to one or both ends.

In a specific exemplary embodiment, to protect the donor molecule from degradation, additionally, the addition of terminal amino group(s) and the use of, for example, phosphorothioate, phosphoramidate, O-methyl ribose or deoxyribose internucleotide linkages may be included, but the present invention is not limited thereto.

The donor molecule may form a duplex, and also include a triplex-forming nucleic acid.

The donor sequence may have any length, for example, 10 bp to 20 kb (or an arbitrary integer between 10 bp and 20 kb or more than 20 kb), preferably, approximately 100 bp to 10 kb (or an arbitrary integer between 100 bp and 10 kb), and more preferably, approximately 200 bp to 5 kb.

The donor may be codon-optimized according to a subject to be introduced thereinto. For example, when a subject is a human, it may be a donor with a sequence optimized by a human codon.

In one exemplary embodiment of the disclosure disclosed herein, to express the protein of interest, a transgene may be included in a donor included in the composition for manipulating a high-expression secretory gene.

The term "transgene" refers to an exogenous nucleotide inserted into a high-expression secretory gene. For example, the transgene may be inserted into a genome cleavage site in a cleaved hepatocyte using an editor protein and a guide nucleic acid.

The transgene may be DNA or RNA.

The transgene may be an exogenous nucleotide encoding a protein produced in a wild-type hepatocyte.

The transgene may be an exogenous nucleotide encoding a protein produced in a cell except a wild-type hepatocyte.

The transgene may be derived from a species different from a subject.

The transgene may be a wild-type gene. For example, when there is a deficiency or lack of a protein in the subject, a transgene having a sequence which is the same as a normal gene encoding a corresponding protein, that is, a wild-type gene, may be included in a donor.

The transgene may be a mutant gene. Here, the mutation may be deletion, substitution or addition of one or more nucleotides of the wild-type gene.

The transgene may be a fusion protein.

In one example, the protein fused with the transgene may be derived from an exogenous gene.

In another example, the protein fused with the transgene may be derived from an endogenous gene.

For example, the protein fused with the transgene may be derived from a high-expression secretory gene.

The protein fused with the transgene may be present at the amino (N)-terminus of the exogenous protein or the vicinity thereof.

The protein fused with the transgene may be present at the carboxyl (C)-terminus of the exogenous protein or the vicinity thereof.

The protein fused with the transgene may be present at both of the amino (N)-terminus and the carboxyl (C)-terminus of the exogenous protein, or the vicinity thereof, or in a mixed form thereof.

The transgene may be a functional gene for enhancing or improving a desired specific function.

In one example, the transgene may enhance the function of an endogenous gene in a hepatocyte.

In another example, the transgene may function to increase the expression of the wild-type gene. For example, when the transgene is a gene encoding a protein deficient in a hepatocyte, the deficient protein may be produced in hepatocytes, and the function of the corresponding protein may normally operate, or a corresponding disease may be treated.

In one example, the transgene may function to correct a mutated gene.

In another example, the transgene may function to regulate the expression of a genomic sequence in a target gene.

In one example, the transgene may function to replace an existing protein or express a novel protein.

In addition, the transgene may be inserted into a high-expression secretory gene to partially or completely inactivate one or more target sequences.

The transgene may be a gene encoding a protein of interest.

The protein of interest may be a protein for enhancing the function in a body. For example, the protein of interest may enhance the function of a metabolic action.

The protein of interest may be a protein for preventing a disease.

The protein of interest may be a protein for alleviating a disease.

The protein of interest may be a protein for treating a disease.

An exemplary embodiment of the disclosure disclosed herein is for treating a disease by expressing a protein of interest by artificially manipulating a hepatocyte.

In the specification, compared to existing alternative therapies such as a transfusion, administration of a protein at regular intervals, and an antibody-based therapy for suppressing a factor involved in a corresponding disease, a disease may be permanently and radically treated by continuously expressing a corresponding gene at a high level by inserting a therapeutic gene into a high-expression secretory gene to treat the disease.

The types of diseases are as follows.

The disease may be a disease that can be prevented or treated by an antibody. For example, a disease such as HIV, Alzheimer's disease or amyotrophic lateral sclerosis may be treated by inserting a gene encoding an antibody into a high-expression secretory gene and expressing the gene.

The disease may be a disease occurring due to a decrease in the expression of a specific gene. For example, a disease caused by the lack of a secretory gene product may be treated by inserting a deficient gene into a high-expression secretory gene and expressing the gene.

The disease may be a genetic disorder occurring by the inhibition of a normal function due to the mutation of a specific gene. In one example, the disease caused by various mutations in single genes may be treated by inserting a wild-type gene into a high-expression secretory gene and expressing the gene. For example, such a genetic disorder may be hemophilia.

The disease may be a disease related to an inherited metabolic disorder.

The "inherited metabolic disorder" is a disease occurring due to the deficiency of an enzyme or co-enzyme responsible for a biochemical metabolic pathway of the body. The inherited metabolic disorder refers to a condition in which deficiency occurs since a final product may not be normally produced, and unnecessary precursors are accumulated in various main organs (brain, heart, liver, kidney, etc.), resulting in an excessive symptom such as intellectual disability.

Examples of the inherited metabolic disorder may include immunodeficiency, hypercholesterolemia, hemophilia, emphysema, cystic fibrosis, phenylketonuria, citrullinemia, methylmalonic acidemia, carnitine palmitoryl transferase deficiency, Hurler syndrome, Ornithine transcarbamylase deficiency, and Tay-Sachs disease.

Other examples of the inherited metabolic disorder include hemophilia A, hemophilia B, and hemophilia C.

For example, hemophilia A is caused by the mutation of the F8 gene located on the X chromosome, hemophilia B is caused by the mutation of the F9 gene located near the F8 gene, and hemophilia C is caused by the mutation of the F11 gene.

The disease may be a lysosomal storage disorder.

The Lysosomal storage disorders may be Mucopolysaccharidosis, Lysosomal acid lipase deficiency, Glycogen storage diseases, Galactosemia, Sickle cell anaemia, Cystic fibrosis, Tay-Sachs disease, Phenylketonuria, Albinism, Medium-chain acyl-CoA dehydrogenase deficiency, Farber disease, Krabbe disease, Galactosialidosis, Gangliosidosis, Alpha-galactosidase, Fabry disease, Schindler disease, Sandhoff disease, Gaucher Disease, Niemann-Pick disease, Sulfatidosis, Metachromatic Leukodystrophy, Multiple sulfatase deficiency, Hurler Syndrome, Scheie Syndrome, Hurler-Scheie Syndrome, Hunter syndrome, Sanfilippo syndrome, Morquio syndrome, Maroteaux-Lamy syndrome, Sly Syndrome, Hyaluronidase deficiency, Mucolipidosis, Sialidosis, I-cell disease, Pseudo-Hurler Polydystrophy, Mucolipidin 1 deficiency, Lipidosis, Santavuori-Haltia disease, Jansky-Bielschowsky disease, Batten-Spielmeyer-Vogt disease, Kufs disease, Wolman disease, Alpha-mannosidosis, Beta-mannosidosis, Aspartylglucosaminuria, Fucosidosis, Cystinosis, Pycnodysostosis, Salla disease, Infantile Free Sialic Acid Storage Disease, Pompe Disease, Danon disease, or Cholesteryl ester storage disease.

As an exemplary embodiment of the disclosure disclosed herein, the transgene included in the donor may be a therapeutic gene for treating a genetic disorder.

The therapeutic gene may encode a protein capable of being used as a therapeutic agent for a specific genetic disorder.

The therapeutic gene may include a wild-type gene (normal gene form) of a disease gene involved in a specific genetic disorder (mutated form of a normal gene), or a part of the wild-type gene (e.g., functional domain).

In an exemplary embodiment, the therapeutic gene may be selected from the group consisting of IDUA, I2S, SGSH, NAGLU, HGSNAT, GNS, GALNS, GLB1, ARSB, GUSB, HYAL, NEU, GNPTAB and MCOLN1.

In another exemplary embodiment, the therapeutic gene may be selected from the group consisting of SAH1, GALC, CTSA, GLA, NAGA, beta-galactosidase, hexosaminidase, GBA, SMPD1, ARSA and SUMF.

In still another example, the therapeutic gene, that is, the normal form of a disease-causing gene, may be selected from the group consisting of NPC, PPT, TPP1, CLN3, CLN6, PPT1, DNAJC5, CTSF, CLN7, CLN8 and CTSD.

In yet another example, the therapeutic gene, that is, the normal form of a disease-causing gene, may be GAA or LAMP2.

In yet another example, the therapeutic gene, that is, the normal form of a disease-causing gene, may be CTNS, CTSK or SLC17A5.

In yet another example, the therapeutic gene, that is, the normal form of a disease-causing gene, may be selected from the group consisting of MAN2B, MAN2C, MANBA, AGA, FUCA1 and LAL.

In yet another example, the therapeutic gene, that is, the normal form of a disease-causing gene, may be a gene encoding a protein selected from the group consisting of methylmalonic aciduria CbIA Type (MMAA) protein, methylmalonic aciduria CbIB Type (MMAB) protein, methylmalonic aciduria CbIC Type (MMADHC) protein, 5-Methyltetrahydrofolate-Homocysteine Methyltransferase Reductase (MTRR) protein, lysosomal membrane protein domain (LMBRD 1) protein, 5-Methyltetrahydrofolate-Homocysteine Methyltransferase (MTR) protein, propionyl-CoA protein, glucose-6-phosphate transporter (G6PT) protein, glucose-6-phosphatase (G6Pase) protein, low density lipoprotein receptor (LDLR) protein, low density lipoprotein receptor adaptor protein 1 (LDLRAP-1 protein), N-acetylglutamate synthetase (NAGS) protein, carbamoyl phosphate synthetase 1 (CPS1) protein, ornthine transcarbamylase (OTC) protein, argininosuccinic acid synthetase (ASS) protein, argininosuccinase acid lyase (ASL) protein, arginase (ARG1) protein, solute carrier family 25 protein, UDP glucuronosyltransferase 1 family, polypeptide A1 (UGT1A1) protein, fumarylacetoacetate hydrolyase (FAH), alanine-glyoxylate aminotransferase (AGXT) protein, glyoxylate reductase/hydroxypyruvate reductase (GRHPR) protein, APTase Cu(2+) transporting beta (ATP7B) protein, phenylalanine hydroxylase (PAH) protein and lipoprotein lyase (LPL) protein.

In yet another example, the therapeutic gene, that is, the normal form of a disease-causing gene, may be selected from the group consisting of FVII, FVIII, FIX, FX, FXI, FXII and other coagulation factors.

For example, in the case of hemophilia, the gene encoding a transgene may be inserted into an endogenous APOC3 gene locus to have high protein expression by the expression regulatory factor of the APOC3 gene. Here, arbitrary peptides or proteins expressing FVII, FVIII, FIX, FX, FXI, and FXII at a high level or helping to express the coagulation factors may be highly expressed.

In one exemplary embodiment, the therapeutic gene may be a gene encoding an antibody.

The therapeutic gene is a gene encoding a protein or polypeptide that blocks a specific factor or signal pathway involved in the occurrence of a disease by an antibody.

For example, the therapeutic gene may be a gene encoding an antibody that is bonded with beta-amyloid to treat Alzheimer's disease.

For example, to treat HIV, the therapeutic gene may be a gene encoding zidovudine (AZT), didanosine (ddI), zalcitabine (ddC), lamivudine (3TC), stavudine (d4T), abacavir (TDF) or emtricitabine (FTC) among nucleoside analogue reverse transcriptase inhibitors (NRTIs), or a gene encoding nevirapine (NVP) or efavirenz (EFV) among non-nucleoside analogue reverse transcriptase inhibitors (NNRTIs), or a gene encoding sanquinavir (SQV), ritonavir (RTV), indinavir (IDV), nelfinavir (NFV), Lopinavir (LPV), atazanavir (ATV) or amprenavir (APV) among protease inhibitors.

In another exemplary embodiment, the therapeutic gene may treat a genetic disorder by increasing or decreasing the expression of a wild-type gene by inserting a factor that regulates the expression of a wild-type gene.

In still another exemplary embodiment, the therapeutic gene may treat a genetic disorder by producing a protein with an improved or new function by deleting, adding or substituting a partial sequence of the wild-type gene.

For example, the therapeutic gene may be fused with a specific peptide that can be penetrated into a specific tissue such as the blood-brain barrier (BBB) or a functional peptide capable of improving the therapeutic effect of the therapeutic gene.

In one exemplary embodiment of the disclosure disclosed herein, the donor may further include a gene for inserting and/or synthesizing a transgene in a target genome.

The insertion and/or synthesis of a transgene in a target genome may be caused by homologous recombination (HDR) or non-homologous recombination (non-homologous endjoining; NHEJ).

The term "recombination" refers to the process of exchanging genetic information between two polynucleotides, including transgene insertion by the non-homologous recombination (NHEJ) and the homologous recombination (HDR).

The "non-homologous recombination (NHEJ)" disclosed herein refers to a specialized form of the exchange occurring between DNA sequences which do not share sequence homology or are not shown in a site-specific recombinant sequence.

Here, a transgene may be inserted into a high-expression secretory gene by non-homologous recombination.

For example, when a partial sequence of the transgene and a partial sequence of a target gene are the same, the same partial sequence may be cleaved by the same site-specific nucleases, and the transgene may be inserted into a target gene-deleted sequence or an adjacent site thereto due to non-homologous recombination.

The "homologous recombination (HDR)" disclosed herein refers to, for example, a specialized form of exchange occurring during double strand cleavage repair in cells through a homology-directed repair mechanism.

The donor sequence may include a homology arm for the homologous recombination of a transgene.

The homology arm may contain a sequence that is the same as or complementary to a target sequence or a sequence adjacent thereto.

The homology arm may contain a sequence which is homologous with but not the same as a target sequence or a sequence adjacent thereto, or a sequence which is homologous but not completely homologous with a target sequence.

homology arm having a sequence homologous with or the same as the highly expressed and secretory gene may include at least one nucleotide(s) mismatched to a sequence of the high expressed and secretory gene.

In a certain exemplary embodiment, most donor sequences which are homologous to a target sequence exhibit approximately 80 to 99% (or an arbitrary value between 80 to 90%) sequence identity with respect to a genome sequence to be replaced.

The homology arm may allow homologous recombination such that a sequence which is not the same as a target sequence, that is, a transgene, is inserted into the target sequence.

For example, when there is a sequence homologous to the donor sequence in a region in which a double strand is destroyed by the guide nucleic acid and the editor protein, a transgene may be inserted into a transgene sequence next to the homology sequence by homologous recombination.

The donor molecule may contain several non-continuous regions, which are homologous to a high-expression secretory gene.

The homology arm included in the donor sequence may include a nucleotide sequence having homology with a nucleotide sequence in one direction (e.g., upstream) of a cleavage site of a high-expression secretory gene.

The homology arm included in the donor sequence may include a nucleotide sequence having homology with a nucleotide sequence in a different direction (e.g., downstream) of a cleavage site of a high-expression secretory gene.

The homology arm included in the donor sequence may include a nucleotide sequence having homology with each of the nucleotide sequences upstream and downstream of the cleavage site of a high-expression secretory gene.

For example, when a transgene is inserted into a site spaced 30 bp or more from both sides of the cleavage site in the target sequence, both termini of the transgene in the donor sequence include a homology arm having a sequence having homology with or the same as the gene sequence present at a position spaced 30 bp from the cleavage site.

Each of the homology arms has a length of at least 15 bp to approximately 3 kb (e.g., approximately 800, 850, 900, 950, 1000, 1100, 1200b or bp long).

In one example, the homology arms may be 500 to 1500 bp long, respectively. Preferably, the homology arms may be 800 to 1200 bp long, respectively.

Generally, the homology arms may be provided as a single or double-stranded oligonucleotide. An exemplary single or double-stranded oligo nucleotide as a template may have a length of 800, 850, 900, 950, 1000, 150, 1100, 1150, 1200b or bp, or at least approximately 800, 850, 900, 950, 1000, 1050, 1100, 1150, 1200, 1250 bp or 1300 bp.

In addition, in one exemplary embodiment of the disclosure disclosed herein, the donor may further include a gene regulating transcription and expression, in addition to the transgene.

The donor may include one or more genes or cDNA molecules, and include an encoded or non-encoded region.

The donor may include a regulatory sequence which controls gene transcription and expression, that is, a sequence encoding an enhancer, an insulator, an internal ribosome entry point, a 2A peptide and/or a polyadenylation signal, or a promoter.

In addition, the donor may further include a reporter gene (e.g., GFP) or a selection marker.

The insertion of a transgene into a high-expression secretory gene by a donor sequence is determined by the presence of the homology region between a sequence in a donor and a target sequence in the target sequence, and the use thereof.

[Delivery and Delivery Method]

In one exemplary embodiment of the disclosure disclosed herein, a guide nucleic acid, an editor protein and/or a donor molecule may be delivered or introduced into a subject by a vector containing a sequence encoding the same, a non-vector or a combination thereof.

The guide nucleic acid may be delivered or introduced into a subject in the form of DNA, RNA, or a mixture thereof.

The editor protein may be delivered or introduced into a subject in the form of DNA, RNA, a DNA/RNA mixture, a peptide, a polypeptide or protein, which encodes the editor protein.

The donor may be delivered or introduced into a subject in the form of DNA, RNA or a single-stranded oligonucleotide DNA template (ssODT).

For example, when the donor is delivered or introduced into a subject, all or a part of the transgene may be inserted into a target gene through recombination.

The guide nucleic acid, editor protein and/or donor may be delivered into a subject by various methods.

The guide nucleic acid, editor protein and/or donor may be delivered by using a vector.

Here, the vector may be a viral vector or a non-viral vector.

The guide nucleic acid, editor protein and/or donor may be delivered by using a non-vector.

(1) Vector

The vector may be a viral or non-viral vector (e.g., a plasmid).

The term "vector" may deliver a gene sequence into a cell. Typically, the "vector construct," "expression vector," and "gene transfer vector" may direct the expression of a gene of interest, and means an arbitrary nucleic acid construct capable of delivering a gene sequence into a target cell. Therefore, this term includes all cloning and expression vehicles and vectors.

The vector may include nucleotide sequence(s) encoding a guide nucleic acid, editor protein and/or donor.

Here, the guide nucleic acid, editor protein and/or donor may be DNA, RNA or a mixture thereof.

The guide nucleic acid, editor protein and/or donor may be delivered by using the same or different vectors. For example, the donor may be delivered by a plasmid, but the guide nucleic acid and/or editor protein may be delivered by one or more viral vectors.

The guide nucleic acid, editor protein and/or donor may be delivered or introduced by using one or more vectors.

In one example, the guide nucleic acid, editor protein and/or donor may be delivered or introduced by using the same vector.

In another example, both of the guide nucleic acid and the editor protein may be included in one vector in the form of a nucleotide sequence, and the donor may be delivered or introduced by using a different vector.

In one example, both of the guide nucleic acid and the donor polynucleotide may be included in one vector, and the editor protein may be delivered or introduced by using a different vector in the form of a nucleotide sequence.

In another example, both of the editor protein and the donor may be included in one vector in the form of a nucleotide sequence, and the guide nucleic acid may be delivered or introduced by using a different vector.

For example, the guide nucleic acid, editor protein and/or donor may be contained in different vectors, respectively.

All domains included in the guide nucleic acid may be contained in one vector, or each domain may be contained in a different vector.

In the case of the editor protein, a nucleotide sequence encoding the editor protein may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splicing acceptor and/or a 2A sequence.

In addition, a vector may further contain a selection marker for selecting a host cell containing a reporter gene (e.g., GFP) or vector, and a replicable vector may further contain a replication origin.

The vector may be contain a splicing acceptor (SA) sequence on the left and right sides of or adjacent to the transgene.

The promoter may be an endogenous promoter or exogenous promoter in a target region.

The promoter may be a promoter recognized by RNA polymerase II or III.

The promoter may be a constitutive promoter.

The promoter may be an inducible promoter.

The promoter may be a target-specific promoter.

The promoter may be a viral or non-viral promoter.

As the promoter, a suitable promoter may be used depending on a control region (i.e., a guide nucleic acid, an editor protein or a transgene). For example, a promoter useful for a guide nucleic acid may be an H1, EF-1a, tRNA or U6 promoter.

For example, a promoter useful for an editor protein may be a CMV, EF-1a, EFS, MSCV, PGK or CAG promoter. For example, a promoter useful for a transgene may be an APOC3 or HP promoter.

The vector may be a viral or recombinant viral vector.

The virus may be DNA virus or RNA virus.

Here, the DNA virus may be a double-stranded DNA (dsDNA) virus or a single-stranded DNA (ssDNA) virus.

Here, the RNA virus may be a single-stranded RNA (ssRNA) virus.

The viral vector may be a retroviral vector, a lentiviral vector, an adenoviral vector, a fox viral vector, a herpes viral vector, a herpes simplex virus, a vaccinia virus or an adeno-associated viral (AAV) vector, but the present invention is not limited thereto.

When a guide nucleic acid, editor protein and/or donor molecule is introduced into a target organism using a virus, the guide nucleic acid, editor protein and/or donor molecule may be temporarily expressed in a subject. Alternatively, the guide nucleic acid, editor protein and/or donor molecule may be continuously expressed for a long time. For example, the guide nucleic acid, editor protein and/or donor molecule may be expressed for 1, 2 or 3 weeks, 1, 2, 3, 4, 5 or 6 months, 1 or 2 years, or permanently.

A viral packaging capacity may vary at least from 2 kb to 50 kb according to the type of a virus. According to such packaging capacity, it is possible to design a viral vector containing a guide nucleic acid or an editor protein alone or to design a viral vector containing both of a guide nucleic acid and an editor protein. Alternatively, a viral vector containing a guide nucleic acid, an editor protein and an additional component may be designed.

For example, a retroviral vector has a packaging capacity for up to 6 to 10 kb of foreign sequence(s), and consists of cis-long terminal repeats (LTRs). Such a retroviral vector is used to insert a therapeutic gene into a cell, and provide the permanent transgene expression.

In another example, an AAV vector can be repeatedly administered because of its very high transduction efficiency in various cells (muscle, brain, liver, lung, retina, ear, heart, blood vessel, etc.) regardless of cell division, has no pathogenicity, and no induction of an immune response since most of a viral genome can be substituted with a therapeutic gene. In addition, as AAV is inserted into a chromosome of a target cell, a therapeutic protein is stably expressed for a long time. For example, it is useful for transduction of a nucleic acid and a peptide, which are previously produced in vitro, into a target nucleic acid of cells in vivo and in vitro. However, AAV is small in size and has a packaging capacity of 4.5 kb or less.

In one example, a nucleotide sequence encoding a guide nucleic acid, an editor protein and/or a donor molecule may be delivered or introduced into a subject by a recombinant lentivirus.

In another example, a nucleotide sequence encoding a guide nucleic acid, an editor protein and/or a donor molecule may be delivered or introduced by a recombinant adenovirus.

In one example, a nucleotide sequence encoding a guide nucleic acid, an editor protein and/or a donor molecule may be delivered or introduced by recombinant AAV.

The vector may include a modification such as a phosphorothioate linkage of nucleic acids, a locked nucleic acid (LNA), 2'-O-methyl 3'phosphorothioate (MS) or 2'-O-methyl 3'thioPACE (MSP).

The nucleotide sequence encoding a guide nucleic acid, an editor protein and/or a donor molecule may be delivered or introduced by a non-viral vector.

A non-viral vector may include nucleotide sequence(s) encoding a guide nucleic acid, an editor protein and/or a donor molecule.

For example, a non-viral vector may be a plasmid, and additionally include a reporter gene, and a nuclear targeting sequence. Other than these, other additives may be included.

(2) Non-Vector

The guide nucleic acid, editor protein and/or donor molecule may be delivered or introduced into a subject by using a non-vector.

Nucleotide sequence(s) encoding the guide nucleic acid, an editor protein and/or a donor molecule may be delivered or introduced into a subject by using a non-vector.

The non-vector may be naked DNA, a DNA complex, mRNA or a mixture thereof.

The non-vector may be delivered or introduced into a subject by electroporation, lipofection, microinjection, gene gun, virosomes, liposomes, immunoliposomes, lipid-mediated transfection or a combination thereof.

In one example, the non-vector may be transferred into a subject by a positive liposome method. This method is used to form stable liposomes since DPOE consists of a positive amphiphile and a neutral helper lipid. Here, since a liposome-DNA complex is positively charged, it may bind to a negatively-charged cell surface and be introduced into cells through endocytosis.

In another example, DNA may be coated with gold particles, and injected into cells.

Additionally, a nucleic acid to be delivered to EnGeneIC delivery vehicles (EDVs) may be packaged and then delivered or introduced. Specifically, EDV is delivered into the target tissue by using a bispecific antibody thereof the one arm of the antibody has specificity for the target tissue and the other arm has a specificity for the EDV. The antibody carries the EDV to the surface of the target cell, and then the EDV may enter the cell by endocytosis.

The guide nucleic acid-editor protein complex may be formed to be delivered or introduced into a subject in the form of the mixture of a nucleic acid and a protein.

The guide nucleic acid and the editor protein may be delivered or introduced into a subject in the form of a nucleic acid-protein mixture.

Alternatively, the guide nucleic acid and the editor protein may be delivered or introduced into a subject in the form of a guide nucleic acid-editor protein complex.

The guide nucleic acid may be DNA, RNA or a mixture thereof. In addition, the editor protein may be in the form of a polynucleotide or protein.

In one exemplary embodiment, an RNA-type guide nucleic acid and a protein-type editor protein may be delivered or introduced into a subject in the form of a guide nucleic acid-editor protein complex, that is, a ribonucleoprotein (RNP).

(3) Delivery Method

In Vivo Delivery Method

The guide nucleic acid and the editor protein may be directly administered into a subject in the form of a vector or non-vector, which contains a nucleic acid encoding the guide nucleic acid and the editor protein, or a guide nucleic acid-editor protein complex (ribonucleoprotein (RNP)).

In addition, the donor molecule may be directly administered into a subject in the form of a vector or non-vector, which contains nucleotide sequence(s) encoding both or each of the guide nucleic acid and/or the editor protein.

The injection may be performed by delivery or introduction into a subject through systemic administration or local application. However, the present invention is not limited thereto.

The systemic administration may be, for example, intravenous, intraperitoneal, intramuscular or subcutaneous injection. Intravenous systemic administration is preferably used.

When the guide nucleic acid, editor protein and/or donor molecule are contained in two or more different vectors, they may be administered via different routes (intramuscular injection, tail vein injection, other intravenous injections and/or intraperitoneal injection).

In addition, when the guide nucleic acid, editor protein and/or donor molecule are contained in two or more different vectors, they may be delivered simultaneously or in a random sequential order.

Ex Vivo or In Vitro Delivery Method

The guide nucleic acid, editor protein and/or donor molecule may be delivered into cells explanted from an individual subject or universal hematopoietic stem cells, and then the cells may be re-transplanted into a subject.

The delivery method may be used for delivery into a subject by i) contacting a guide nucleic acid, editor protein and/or donor molecule with cells, and ii) directly administering the contacted cells into a subject.

Specifically, in the intracellular contacting step, a guide nucleic acid and an editor protein may be introduced into cells in the form of a vector or non-vector containing a nucleotide sequence encoding the guide nucleic acid or/and the editor protein, or a guide nucleic acid-editor protein complex (ribonucleoprotein (RNP)). Alternatively, the donor molecule may be introduced into cells in the form of a vector or non-vector, which contains a nucleotide sequence encoding both or each of a guide nucleic acid and/or an editor protein.

For example, when the guide nucleic acid and the editor protein are introduced into cells in the form of a vector, the contacting step (i) may be performed by one or more methods selected from electroporation, liposomes, nanoparticles and a protein translocation domain (PTD)-fused protein method.

In another example, when the guide nucleic acid and the editor protein are introduced into cells in the form of a vector, the contacting step (i) may be performed by one or more selected from the group consisting of a non-viral vector, which is a plasmid, and a viral vector.

The step ii) is for directly administering the contacted cells obtained in step i) into a subject, and the cells may be delivered or introduced into a subject by systemic administration or local application. However, the present invention is not limited thereto.

The systemic administration may be, for example, intravenous, intraperitoneal, intramuscular or subcutaneous injection. Preferably, intravenous systemic administration is used.

The disclosure disclosed herein includes a subject modified by introducing or delivering a guide nucleic acid, editor protein and/or donor into the subject.

The modified subject may be obtained by inserting a transgene into a hepatocyte genome.

One specific example of the modified subject is an artificially manipulated hepatocyte.

The modified hepatocyte may be a hepatocyte including an artificially manipulated high-expression secretory gene.

The artificially manipulated high-expression secretory gene may be a gene into which a transgene is inserted into a high-expression secretory gene.

The artificially manipulated gene may have a transgene introduced into the coding region of a high-expression secretory gene.

In one example, the transgene may be in an exon region of a high-expression secretory gene.

For example, there may be exon1, exon2, exon3 and exon4 in a coding sequence of the APOC3 gene among the high-expression secretory genes.

The transgene may be located in exon1 of the APOC3 gene.

The transgene may be located in exon2 of the APOC gene.

The transgene may be exon3 of the APOC gene.

The transgene may be located in exon4 of the APOC gene.

In another example, there may be exon1, exon2, exon3, exon4 and exon5 in the coding sequence of the HP gene among the high-expression secretory genes.

Here, the transgene may be located in exon1 of the HP gene.

Here, the transgene may be located in exon2 of the HP gene.

Here, the transgene may be located in exon3 of the HP gene.

Here, the transgene may be located in exon4 of the HP gene.

Here, the transgene may be located in exon5 of the HP gene.

In addition, the artificially manipulated gene may be in form in which a transgene is inserted into a non-coding sequence of a high-expression secretory gene.

The transgene may be introduced into a region located in a promoter, an enhancer, an intron, 3'UTR, a poly A tail or a mixture thereof.

In one example, the transgene may be inserted into an intron region of a high-expression secretory gene.

For example, there may be three introns such as intron1, intron2 and intron3 located in the coding sequence of the APOC3 gene among high-expression secretory genes.

Here, the transgene may be located in intron1 of the APOC3 gene.

Here, the transgene may be located in intron2 of the APOC3 gene.

Here, the transgene may be located in intron3 of the APOC3 gene.

In another example, inron1, intron2, intron3 and intron4 may be located in the coding sequence of the HP gene among high-expression secretory genes.

Here, the transgene may be located in intron1 of the HP gene.

Here, the transgene may be located in intron2 of the HP gene.

Here, the transgene may be located in intron3 of the HP gene.

Here, the transgene may be located in intron4 of the HP gene.

The transgene may be inserted into an exon, an intron or both thereof.

In one example, the transgene may be located in both of exon and intron regions of the APOC3 gene.

The transgene may be located in both of exon1 and intron1 regions of the APOC3 gene.

The transgene may be located in both of intron1 and exon2 regions of the APOC3 gene.

The transgene may be located in both of exon2 and intron2 regions of the APOC3 gene.

The transgene may be located in both of intron2 and exon3 regions of the APOC3 gene.

The transgene may be located in both of exon3 and intron3 regions of the APOC3 gene.

The transgene may be located in both of intron3 and exon4 regions of the APOC3 gene.

In another example, the transgene may be located in both of exon and intron regions of the HP gene.

The transgene may be located in both of exon1 and intron1 regions of the HP gene.

The transgene may be located in both of intron1 and exon2 regions of the HP gene.

The transgene may be located in both of exon2 and intron2 regions of the HP gene.

The transgene may be located in both of intron2 and exon3 regions of the HP gene.

The transgene may be located in both of exon3 and intron3 regions of the HP gene.

The transgene may be located in both of intron3 and exon4 regions of the HP gene.

The transgene may be located in both of exon4 and intron4 regions of the HP gene.

The transgene may be located in both of intron4 and exon5 regions of the HP gene.

In addition, the transgene may be inserted into a region containing a mutant part (e.g., a part different from a wild-type gene) of a high-expression secretory gene.

In addition, the transgene may be inserted into the sequence of 10 to 35 consecutive nucleotides adjacent to the 5' end and/or the 3' end of a PAM sequence in the nucleotide sequence of a high-expression secretory gene.

Here, the PAM sequence may be, for example, one or more of the following sequences (described in the 5' to 3' direction).

NGG (N is A, T, C or G);

NNNNRYAC (N is each independently A, T, C or G, R is A or G, and Y is C or T);

NNAGAAW (N is each independently A, T, C or G, and W is A or T);

NNNNGATT (N is each independently A, T, C or G);

NNGRR(T) (N is each independently A, T, C or G, R is A or G, and Y is C or T); and TTN (N is A, T, C or G).

Here, the transgene may be in a sequence of 10 to 35 nucleotides, 15 to 35 nucleotides, 20 to 35 nucleotides, 25 to 35 nucleotides or 30 to 35 nucleotides.

Alternatively, the transgene may be in a sequence of 10 to 15 nucleotides, 15 to 20 nucleotides, 20 to 25 nucleotides, 25 to 30 nucleotides, or 30 to 35 nucleotides.

In one exemplary embodiment, when a PAM sequence recognizing an editor protein is 5'-NGG-3', 5'-NAG-3' and/or 5'-NGA-3' (N=A, T, G or C; or A, U, G or C), a transgene may be located in 10 to 25 consecutive nucleotides adjacent to the 5' terminus and/or 3' terminus of the 5'-NGG-3', 5'-NAG-3' and/or 5'-NGA-3' (N=A, T, G or C; or A, U, G or C) sequence in the nucleotide sequence of the HP gene.

In another exemplary embodiment, when a PAM sequence recognizing an editor protein is 5'-NGGNG-3' and/or 5'-NNAGAAW-3' (W=A or T, N=A, T, G or C; or A, U, G or C), a transgene may be located in 10 to 25 consecutive nucleotides adjacent to the 5' terminus and/or 3' terminus of the 5'-NGGNG-3' and/or 5'-NNAGAAW-3' (W=A or T, N=A, T, G or C; or A, U, G or C) sequence in the nucleotide sequence of the HP gene.

In still another exemplary embodiment, when a PAM sequence recognizing an editor protein is 5'-NNNNGATT-3' and/or 5'-NNNGCTT-3' (N=A, T, G or C; or A, U, G or C), a transgene may be located in 10 to 25 consecutive nucleotides adjacent to the 5' terminus and/or 3' terminus of the 5'-NNNNGATT-3' and/or 5'-NNNGCTT-3' (N=A, T, G or C; or A, U, G or C) sequence in the nucleotide sequence of the HP gene.

In one exemplary embodiment, when a PAM sequence recognizing an editor protein is 5'-NNNVRYAC-3' (V=G, C or A; R=A or G, Y=C or T, N=A, T, G or C; or A, U, G or C), a transgene may be located in 10 to 25 consecutive nucleotides adjacent to the 5' terminus and/or 3' terminus of the 5'-NNNVRYAC-3' (V=G, C or A; R=A or G, Y=C or T, N=A, T, G or C; or A, U, G or C) sequence in the nucleotide sequence of the HP gene.

In another exemplary embodiment, when a PAM sequence recognizing an editor protein is 5'-NAAR-3'(R=A or G, N=A, T, G or C; or A, U, G or C), a transgene may be located in 10 to 25 consecutive nucleotides adjacent to the 5' terminus and/or 3' terminus of the 5'-NAAR-3'(R=A or G, N=A, T, G or C; or A, U, G or C) sequence in the nucleotide sequence of the HP gene.

In still another exemplary embodiment, when a PAM sequence recognizing an editor protein is 5'-NNGRR-3', 5'-NNGRRT-3' and/or 5'-NNGRRV-3' (R=A or G, V=G, C or A, N=A, T, G or C; or A, U, G or C), a transgene may be located in 10 to 25 consecutive nucleotides adjacent to the 5' terminus and/or 3' terminus of the 5'-NNGRR-3', 5'-NNGRRT-3' and/or 5'-NNGRRV-3' (R=A or G, V=G, C or A, N=A, T, G or C; or A, U, G or C) sequence in the nucleotide sequence of the HP gene.

In one exemplary embodiment, when a PAM sequence recognizing an editor protein is 5'-TTN-3' (N=A, T, G or C;

or A, U, G or C), a transgene may be located in 10 to 25 consecutive nucleotides adjacent to the 5' terminus and/or 3' terminus of the 5'-TTN-3' (N=A, T, G or C; or A, U, G or C) sequence in the nucleotide sequence of the HP gene.

In another example, the transgene may be in the sequence of 10 to 25 consecutive nucleotides adjacent to the 5' terminus and/or the 3' terminus of the PAM sequence in the nucleotide sequence of the APOC3 gene.

In one exemplary embodiment, when a PAM sequence recognizing an editor protein is 5'-NGG-3', 5'-NAG-3' and/or 5'-NGA-3' (N=A, T, G or C; or A, U, G or C), a transgene may be located in 10 to 25 consecutive nucleotides adjacent to the 5' terminus and/or 3' terminus of the 5'-NGG-3', 5'-NAG-3' and/or 5'-NGA-3' (N=A, T, G or C; or A, U, G or C) sequence in the nucleotide sequence of the APOC3 gene.

In another exemplary embodiment, when a PAM sequence recognizing an editor protein is 5'-NGGNG-3' and/or 5'-NNAGAAW-3' (W=A or T, N=A, T, G or C; or A, U, G or C), a transgene may be located in 10 to 25 consecutive nucleotides adjacent to the 5' terminus and/or 3' terminus of the 5'-NGGNG-3' and/or 5'-NNAGAAW-3' (W=A or T, N=A, T, G or C; or A, U, G or C) sequence in the nucleotide sequence of the APOC3 gene.

In still another exemplary embodiment, when a PAM sequence recognizing an editor protein is 5'-NNNNGATT-3' and/or 5'-NNNGCTT-3' (N=A, T, G or C; or A, U, G or C), a transgene may be located in 10 to 25 consecutive nucleotides adjacent to the 5' terminus and/or 3' terminus of the 5'-NNNNGATT-3' and/or 5'-NNNGCTT-3' (N=A, T, G or C; or A, U, G or C) sequence in the nucleotide sequence of the APOC3 gene.

In one exemplary embodiment, when a PAM sequence recognizing an editor protein is 5'-NNNVRYAC-3' (V=G, C or A; R=A or G, Y=C or T, N=A, T, G or C; or A, U, G or C), a transgene may be located in 10 to 25 consecutive nucleotides adjacent to the 5' terminus and/or 3' terminus of the 5'-NNNVRYAC-3' (V=G, C or A; R=A or G, Y=C or T, N=A, T, G or C; or A, U, G or C) sequence in the nucleotide sequence of the APOC3 gene.

In another exemplary embodiment, when a PAM sequence recognizing an editor protein is 5'-NAAR-3' (R=A or G, N=A, T, G or C; or A, U, G or C), a transgene may be located in 10 to 25 consecutive nucleotides adjacent to the 5' terminus and/or 3' terminus of the 5'-NAAR-3' (R=A or G, N=A, T, G or C; or A, U, G or C) sequence in the nucleotide sequence of the APOC3 gene.

In still another exemplary embodiment, when a PAM sequence recognizing an editor protein is 5'-NNGRR-3', 5'-NNGRRT-3' and/or 5'-NNGRRV-3' (R=A or G, V=G, C or A, N=A, T, G or C; or A, U, G or C), the target sequence may have a transgene in 10 to 25 consecutive nucleotides adjacent to the 5' terminus and/or 3' terminus of the 5'-NNGRR-3', 5'-NNGRRT-3' and/or 5'-NNGRRV-3' (R=A or G, V=G, C or A, N=A, T, G or C; or A, U, G or C) sequence in the nucleotide sequence of the APOC3 gene.

In one exemplary embodiment, when a PAM sequence recognizing an editor protein is 5'-TTN-3' (N=A, T, G or C; or A, U, G or C), the target sequence may have a transgene in 10 to 25 consecutive nucleotides adjacent to the 5' terminus and/or 3' terminus of the 5'-TTN-3' (N=A, T, G or C; or A, U, G or C) sequence in the nucleotide sequence of the APOC3 gene.

The modified hepatocyte may be a hepatocyte containing a protein expressed by an artificially manipulated high-expression secretory gene (hereinafter, referred to as an "artificial expression protein").

In the artificial expression protein, a high-expression secretory gene and/or a transgene is(are) expressed.

In one example, the hepatocyte may contain a protein produced by expressing a transgene.

In another example, the hepatocyte may contain both of a protein produced by expressing a transgene and a protein produced by expressing an artificially manipulated high-expression secretory gene.

In addition, the expression level of a high-expression secretory gene may be regulated by artificial manipulation.

In one example, the expression level of the high-expression secretory gene may be higher than that before the high-expression secretory gene is artificially manipulated.

In another example, the expression level of the high-expression secretory gene may be lower than that before the high-expression secretory gene is artificially manipulated.

In addition, the expressed protein of interest may be a wild-type protein of a gene present in a hepatocyte.

In one example, the protein expressed in a hepatocyte at a predetermined level or less may exhibit an expression level increased by the expression of the protein of interest.

In another example, when the gene present in a hepatocyte is mutated and has an abnormal function, a wild-type gene may be expressed, whereby it may have a normal function. In this case, there may be both of the mutated protein and the wild-type protein in hepatocytes. Alternatively, the mutated protein in hepatocytes may not be expressed, but the wild-type protein may be expressed.

Alternatively, the expressed protein of interest may be a new protein that is not expressed in hepatocytes.

In one example, the expressed protein of interest may be a therapeutic protein. Here, the therapeutic protein is a protein that is not naturally expressed in hepatocytes, and may be used to treat, alleviate or prevent a disease including a genetic disorder.

The expressed protein of interest may be a mutated protein (produced by partially modifying a wild-type protein).

In one example, the expressed protein of interest may be a protein that is expressed by partially modifying nucleotides of some wild-type genes.

For example, some functions of the mutated protein may be enhanced, compared to a wild-type protein.

The expressed protein of interest may be a fusion-type protein.

In one example, the protein of interest may be a fusion protein that is expressed by combining an endogenous gene in a subject with a foreign gene.

In another example, the protein of interest may be a fusion protein that is expressed by bonding foreign genes together.

For example, the protein of interest may be a fusion protein expressed by combining different endogenous genes.

Accordingly, the disclosure disclosed herein includes a hepatocyte modified by an artificially manipulated high-expression secretory gene.

In addition, the disclosure disclosed herein includes liver tissue modified by the modified hepatocyte.

In addition, the disclosure disclosed herein includes the liver modified by the modified liver tissue.

Here, the liver may be partially or entirely modified.

[Method of Expressing Protein of Interest]

One exemplary embodiment of the disclosure disclosed herein relates to a method of expressing a protein of interest in the liver.

The method is performed in vivo, ex vivo, or in vitro.

In some embodiments, the method includes i) introducing a programmable nuclease and a transgene into an organ, tissue or cell.

In one exemplary embodiment, the method may include, as step i), introducing (a) a guide nucleic acid which forms a complementary bond with or has the same sequence(s) as the nucleotide sequence(s) of one or more genes selected from the group of high-expression secretory genes;

(b) an editor protein or a nucleic acid encoding the same; and (c) a donor containing a transgene into a subject.

The one or more genes may be selected from high-expression secretory genes such as FTL, FTH1, ACTB, HP, APOC3, SOD2, ORM1, and F9. Preferably, the gene may be the APOC3 or HP gene.

The guide nucleic acid (a) may include a guide nucleic acid that may have the same sequence as or form a complementary bond with target sequences of SEQ ID Nos: 1 to 348, The editor protein (b) may include one or more editor proteins selected from the group consisting of a *Streptococcus pyogenes*-derived Cas9 protein, *Campylobacter jejuni*-derived Cas9 protein, *Streptococcus* thermophiles-derived Cas9 protein, *Streptococcus aureus*-derived Cas9 protein, *Neisseria meningitidis*-derived Cas9 protein, and a Cpf1 protein.

The transgene (c) may be a gene encoding a protein of interest. For example, the transgene may be a therapeutic gene.

The description of the therapeutic gene is as described above.

The description of the composition for manipulating a gene is as described above.

The introduction step may be performed in vivo.

Here, the (a), (b) and (c) may be delivered by a vector or a non-vector.

The descriptions of the vector, the non-vector and the delivery method are the same as described above.

The method of expressing a protein of interest in the liver may further include confirming transgene expression in the modified organ, tissue or cells by step i).

Here, in step ii),

The organ or tissue modified in step i) may be an organ or tissue in which a transgene is inserted into an organ or tissue genome in a natural state.

The organ or tissue modified in step i) may include a transgene.

Here, a transgene contained in the modified organ or tissue may be expressed in the modified organ or tissue.

The expression of a transgene in the modified organ or tissue may be confirmed by the mRNA or protein expression of a transgene.

As a method of confirming the mRNA expression of a transgene, PCR may be used.

As a method of confirming the protein expression of a transgene, western blotting, ELISA or IP may be used.

In another example, the method may be performed ex vivo or in vitro. Here, to express the protein of interest, a method of preparing an artificially manipulated hepatocyte may be used.

In one exemplary embodiment, the method may be a method of preparing manipulated animal cells which express a protein of interest, which includes bringing into contact (a) animal cells; and (b) a composition for manipulating a gene to artificially insert a transgene into one or more genes selected from high-expression secretory genes such as ALB, FTL, FTH1, ACTB, HP, APOC3, SOD2, ORM1 and F9.

Here, the animal cells (a) may be human-derived somatic or stem cells.

Specifically, human-derived somatic cells may be hepatocytes.

The composition for manipulating a gene (b) is as follows.

The contacting step may include introducing the composition for manipulating a gene (b) into the animal cells (a).

The animal cells used in this method may be animal cells derived from mammals including primates such as a human and a monkey, and rodents such as a mouse and a rat.

[Uses]

An example of the disclosure disclosed herein includes a therapeutic use.

For example, the therapeutic use may include the administration of a composition for inserting a transgene into a hepatocyte genome of a subject or a transgene-inserted hepatocyte.

The subject to be treated may be a mammal, for example, a primate such as a human or a monkey, and a rodent such as a mouse or a rat.

1) Pharmaceutical Composition

One exemplary embodiment of the present specification includes a composition used to treat a disease by highly expressing a therapeutic gene and a method of preparing the same.

For example, the composition may be a composition containing a nuclease artificially manipulated to artificially insert a transgene into a hepatocyte genome and a therapeutic gene. The composition may be referred to as a therapeutic composition or pharmaceutical composition.

In an exemplary embodiment, the composition may include a programmable nuclease.

The programmable nuclease may be one of a clustered regularly interspaced short palindromic repeats (CRISPR)-CRISPR associated protein (Cas) system, a zinc finger nuclease (ZFN), and a transcription activator-like effector nucleases (TALEN).

In an exemplary embodiment, the composition may include a therapeutic gene.

The therapeutic gene may be a gene encoding a deficient protein or enzyme in the body.

For example, the therapeutic gene may be F9. Here, the composition may be a composition for treating hemophilia.

The composition may further include a pharmaceutically acceptable excipient and/or other compounds known in the art, in addition to the programmable nuclease and the therapeutic gene. For example, the composition may include water, salts, dextrose, glycerol, ethanol, and a combination thereof.

Additionally, as a small amount of an additive, a wetting agent, an emulsifier, a pH buffer, a stabilizer, or another reagent that enhance the efficacy of a pharmaceutical composition may be contained.

2) Treatment Method

One exemplary embodiment described in the specification is a method of treating a specific disease, which includes administering an effective amount of the above-described composition to a patient in need of the composition.

For example, a method of treating a disease which can be treated by an antibody is included.

For example, a method of treating a disease caused by mutation of a gene is included.

For example, a method of treating an inherited metabolic disorder is included.

For example, a method of treating a disease caused by deficiency or the absence of a specific protein is included.

For example, the disease may be a disease that can be treated by permanently expressing a therapeutic gene by injecting the therapeutic composition into a patient's body.

The treatment method may be performed by a method of delivering the therapeutic composition into a patient through systemic administration.

The treatment method may be performed by injecting the therapeutic composition into a specific body part of a patient. Here, a specific body part may be an organ containing cells that can highly express a therapeutic gene to be secreted out of the cells.

For example, the cells may be hepatocytes.

For example, the cells may be stem cells.

The treatment method may be a treatment method that affects gene expression of animal cells by directly manipulating the gene using a programmable nuclease. Such a treatment method may be performed by directly injecting a composition for manipulating a gene, which includes a programmable nuclease for manipulating a gene in a living body and a therapeutic gene, into a body.

The programmable nuclease may be a guide nucleic acid and/or editor protein.

The therapeutic gene may be F9.

The composition for manipulating a gene is as described above.

A subject to which the composition is administered may be any one of mammals including primates such as a human, a monkey, etc. and rodents such as a mouse, a rat, etc.

The composition administration may be performed by any convenient method such as injection, transfusion, implantation or transplantation. The composition may be administered subcutaneously, intradermally, intratumorally, intranodally, intramedullary, intramuscularly, intravenously, intralymphatically, or intraperitoneally.

The composition is preferably administered through intravenous systemic administration.

In another example, the administration may be administration to any one or more organs selected from the kidney; a digestive system including the stomach, the pancreas, the duodenum, the ileum and/or the colon; the heart; the lungs; the brain, particularly, neurons and/or generally the CNS; eyes containing retinal tissue; ears containing the inner ear; the skin; muscle; bone; and/or the liver of the therapeutic subject.

The organ is preferably the liver.

In one exemplary embodiment,

The dose (pharmaceutically effective amount to obtain a desired effect) of the composition may be approximately 0.01 to 10 mL of a saline solution containing approximately $1 \times 10^8$ to $1 \times 10^{18}$ functional AAV per mL during the delivery into a human body using AAVs. In one exemplary embodiment of the specification, the AAV content is generally in a concentration range of approximately $1 \times 10^5$ to $1 \times 10^{50}$ genomic AAVs, approximately $1 \times 10^8$ to $1 \times 10^{20}$ genomic AAVs, approximately $1 \times 10^{10}$ to $1 \times 10^{16}$ genomic AAVs, or approximately $1 \times 10^{11}$ to $1 \times 10^{16}$ genomic AAVs. Such a concentration of the AAV may be delivered in approximately 0.001 to 100 mL, approximately 0.01 to 50 mL, or approximately 0.05 to 10 mL of a carrier solution. However, the dose of the composition may be suitably prescribed in consideration of the age, health and body weight of an administration subject, the types of treatments received at the same time, the frequency of treatment, and the characteristic of a desired effect, but the present invention is not limited thereto.

In one exemplary embodiment, the treatment method may be a method of treating hemophilia.

The treatment method may be performed in vivo.

The treatment method includes administering a composition containing a composition for manipulating a gene to express a transgene artificially inserted into a hepatocyte genome as an active ingredient to a treatment subject, wherein the composition for manipulating a gene includes any one of programmable nucleases of a clustered regularly interspaced short palindromic repeats (CRISPR)-CRISPR associated protein (Cas) system, a zinc finger nuclease (ZFN), and a transcription activator-like effector nuclease (TALEN), the artificially inserted transgene is located in one or more gene sequences of the HP gene and APOC3 gene, and the transgene is F9.

The hemophilia may be permanently treated by gene editing treatment using a programmable nuclease.

By inserting a transgene into a hepatocyte genome using the method and composition described in the specification and highly expressing the gene, the expression of a deficient protein may be increased, a final genetic product may be produced by a normal operation of a biochemical metabolic pathway, and a body function may be improved.

EXAMPLES

Hereinafter, the specification will be described in further detail with reference to examples. These examples are merely provided to exemplify the specification, and it should not be construed that the scope of the specification is limited by the examples.

Example 1: RNA Sequencing

Human primary cells were cultured in a 24-well plate containing William's medium for 2 days, and then RNA was isolated using an RNeasy Mini Kit (Qiagen).

A sample with an RNA Integrity Number (RIN) of 7 or more was selected using an Agilent 2100 BioAnalyzer and subjected to mRNA enrichment using 1 μg of RNA and magnetic beads with oligo dT, followed by constructing a cDNA library through short fragmentation and reverse transcription.

Subsequently, a sequencing adaptor was attached using a TrueSeq RNA sample prep kit (Illumina, CA), a cDNA library size (350-450 bp) and a quality were checked using electrophoresis and an Agilent High Sensitivity DNA kit (Agilent Technology, CA), and then sequencing was performed using Illumina HiSeq2500 (Illumina, CA).

Afterward, reads filtering a low quality read corresponding to 10% or more skipped bases (marked as "N") and a quality score of less than 20 were mapped to a human reference genome using the Tophat program, and the FPKM value of each transcript was calculated using the Cufflinks v2.1.1 program.

The transcription activities of Haptoglobin and APOC3 encoding secreted proteins and F9, IDUA, IDS, GLA and GBA corresponding to therapeutic genes per disease were confirmed from the FPKM result.

As shown in FIG. 1, Haptoglobin and APOC3 genes exhibit approximately 170-fold or higher transcriptional activity than other therapeutic genes.

Example 2: Design of sgRNA

CRISPR/Cas9 target sites of human HP1 and APOC3 genes were identified using CRISPR RGEN Tools (Institute for Basic Science, Korea). The target site for each gene may vary according to the type of CRISPR enzyme, the target sequences of the HP and APOC3 genes for CjCas9 are summarized in Tables 2 and 3, and the target sequences of the HP and APOC3 genes for SpCas9 were summarized in Tables 4 and 5.

TABLE 2

| Location | # | SgRNAs | DNA target sequence | Mismatch 0 | 1 | 2 | Indels (%) | SEQ ID NO: |
|---|---|---|---|---|---|---|---|---|
| intron1 | 1 | hHP1-i1-Cj9 | TCCAGGAAAGAGAAACCTCCC | 1 | 0 | 0 | 15.4 (%) | 409 |
|  | 2 | hHP1-i1-Cj10 | CATTCAGGAAAGTACATTGGC | 1 | 0 | 0 | 41.00 (%) | 410 |

TABLE 3

| Location | # | sgRNAs | DNA target sequence | Mismatch 0 | 1 | 2 | Indels (%) | SEQ ID NO: |
|---|---|---|---|---|---|---|---|---|
| Intron-1 | 1 | hHp1-int1-Sp1 | GGTTACATTTTTGACTTTAT | 1 | 0 | 1 | 3.8 | 41 |
|  | 2 | hHp1-int1-Sp2 | CTGGGATACACACTAATACC | 1 | 0 | 1 | 23.5 | 42 |
|  | 3 | hHp1-int1-Sp3 | GCAAGTAGTGCCCGAATGGT | 1 | 0 | 1 | 44.6 | 43 |
|  | 4 | hHp1-int1-Sp4 | TTGTTAGTGAGATGGTGAAC | 1 | 0 | 1 | 52.2 | 44 |
|  | 5 | hHp1-int1-Sp5 | GAACTGGCAGACGGCACCTG | 1 | 0 | 1 | 52.1 | 45 |
|  | 6 | hHp1-int1-Sp6 | AACTGGCAGACGGCACCTGT | 1 | 0 | 0 | 76 | 46 |
|  | 7 | hHp1-int1-Sp7 | CTCAGACACCGCAAAGATAG | 1 | 0 | 0 | 86.4 | 47 |
|  | 8 | hHp1-int1-Sp8 | CACTATCTTTGCGGTGTCTG | 1 | 0 | 0 | 1.3 | 48 |
|  | 9 | hHp1-inf1-Sp9 | ACTATCTTTGCGGTGTCTGA | 1 | 0 | 0 | 69.9 | 49 |
|  | 10 | hHp1-int1-Sp10 | ATCTTTGCGGTGTCTGAGGG | 1 | 0 | 1 | 39.9 | 50 |
|  | 11 | hHp1-int1-Sp11 | AGAAAGGCACATAGGTGGAG | 1 | 0 | 1 | 81.7 | 51 |

TABLE 4

| location | # | SgRNAs | DNA target sequence | Mismatch 0 | 1 | 2 | Indels (%) | SEQ ID NO: |
|---|---|---|---|---|---|---|---|---|
| Intron1 | 1 | hAPOC3-Cj1 | CCAGCCCAGCCAGCAAGCCTGG | 1 | 0 | 1 | 1.41 | 154 |
|  | 2 | hAPOC3-Cj2 | CTTCAGGTTATGAT-GAGGGGTG | 1 | 0 | 0 | 3.02 | 155 |
|  | 3 | hAPOC3-Cj3 | GGGAGGGGTGTCACTTGCC-CAA | 1 | 0 | 2 | 0.02 | 156 |
|  | 4 | hAPOC3-Cj4 | ACCCCCTGTGTAGCTTTGGGCA | 1 | 0 | 0 | 3.58 | 157 |
|  | 5 | hAPOC3-Cj5 | AAGCCTGAAGAAT-GAGGGGGA | 1 | 0 | 0 | 2.83 | 158 |
|  | 6 | hAPOC3-Cj6 | TGGAGAGGGCCAGAAAT-CACCC | 1 | 0 | 0 | 16.74 | 159 |
|  | 7 | hAPOC3-Cj7 | GAGAGGGCCAGAAATCACC-CAA | 1 | 0 | 1 | 19.41 | 160 |
|  | 8 | hAPOC3-Cj8 | GAAACCCACCAGACTGAA-CAT | 1 | 0 | 0 | 2.44 | 161 |
|  | 9 | hAPOC3-Cj9 | AAGGAGTAGGGGCCGGCTCCCT | 1 | 0 | 0 | 0.21 | 162 |

TABLE 4-continued

| location | # | SgRNAs | DNA target sequence | Mismatch 0 | 1 | 2 | Indels (%) | SEQ ID NO: |
|---|---|---|---|---|---|---|---|---|
| | 10 | hAPOC3-Cj10 | TGGGGACCTGGGGTGCCCCTCA | 1 | 0 | 0 | 0.01 | 163 |
| | 11 | hAPOC3-Cj11 | TCCTGCAAGGAAGTGTCCTGTG | 1 | 0 | 0 | 0.15 | 164 |
| Exon2 | 12 | hAPOC3-Cj12 | GGAACAGAGGTGC-CATGCAGCC | 1 | 0 | 0 | 9.55 | 165 |
| | 13 | hAPOC3-Cj13 | CAACAAGGAGTACCCGGGGCTG | 1 | 0 | 0 | 1.2 | 166 |
| | 14 | hAPOC3-Cj14 | GAGCGCCAG-GAGGGCAACAACA | 1 | 0 | 0 | 4.48 | 167 |

TABLE 5

| location | # | sgRNAs | DNA target sequence | Mismatch 0 | 1 | 2 | Indels (%) | SEQ ID NO: |
|---|---|---|---|---|---|---|---|---|
| Exon1 | 1 | hAPOC3-Sp1 | TCTGCTCAGTTCATCCCTAG | 1 | 0 | 0 | 96.4 | 168 |
| Intron1 | 2 | hAPOC3-Sp2 | CTGCTCCAGGTAATGCCCTC | 1 | 0 | 0 | 81.9 | 169 |
| | 3 | hAPOC3-Sp3 | AGAAGCACTTGCTAGAGCTA | 1 | 0 | 0 | 90.9 | 170 |
| | 4 | hAPOC3-Sp4 | GGGGCACCCGTCCAGCTCCG | 1 | 0 | 0 | 72.7 | 171 |
| | 5 | hAPOC3-Sp5 | CTTCAGGTTATGATGAGGGG | 1 | 0 | 0 | 55.4 | 172 |
| | 6 | hAPOC3-Sp6 | GTTCTTCAGGTTATGATGAG | 1 | 0 | 0 | 88.1 | 173 |
| | 7 | hAPOC3-Sp7 | CCCGGGCCTCCATGTTCTTC | 1 | 0 | 0 | 80.4 | 174 |
| | 8 | hAPOC3-Sp8 | AGGTTCCCCCCTCATTCTTC | 1 | 0 | 0 | 91.1 | 175 |
| | 9 | hAPOC3-Sp9 | CCTAAGCCTGAAGAATGAGG | 1 | 0 | 0 | 96.2 | 176 |
| | 10 | hAPOC3-Sp10 | AGCCCTAAGCCTGAAGAATG | 1 | 0 | 0 | 87.7 | 177 |
| | 11 | hAPOC3-Sp11 | GGGTAGGACTGGGCTGTCTA | 1 | 0 | 0 | 90.6 | 178 |
| | 12 | hAPOC3-Sp12 | AGCCCAGTCCTACCCCAGAC | 1 | 0 | 0 | 50.7 | 179 |
| | 13 | hAPOC3-Sp13 | GGTGATTTCTGGCCCTCTCC | 1 | 0 | 0 | 73.4 | 180 |
| | 14 | hAPOC3-Sp14 | CGGAGATCAGTCCAGACCGC | 1 | 0 | 0 | 66.2 | 181 |
| | 15 | hAPOC3-Sp15 | GCGAGGGATCGAGGCCCAAA | 1 | 0 | 0 | 94.8 | 182 |

Example 3: Verification of Activity of QRNA and Off-Target Analysis 3.1 T7E1 Assay 250 ng of a vector for expressing sgRNA and 750 ng of a vector for expressing Cas9, into which the respective gRNA sequences were cloned, were transfected into HEK293 cell lines with Lipofectamine 2000 or by electroporation. In addition, 1 μg of in vitro transcribed sgRNA and 4 μg of Cas9 were mixed in the form of an RNP complex, and transfected into Jurkat cell lines by electroporation.

After approximately 2 to 3 days, genomic DNA was extracted and subjected to PCR to amplify an on-target site, followed by confirming activity through T7E1 assay, or performing additional PCR which attached adaptors specific for a sequencing primer for Next-Generation Sequencing and TruSeq HT double index primers. The activity of gRNA was checked with a band cleaved by T7E1.

Figure 3:
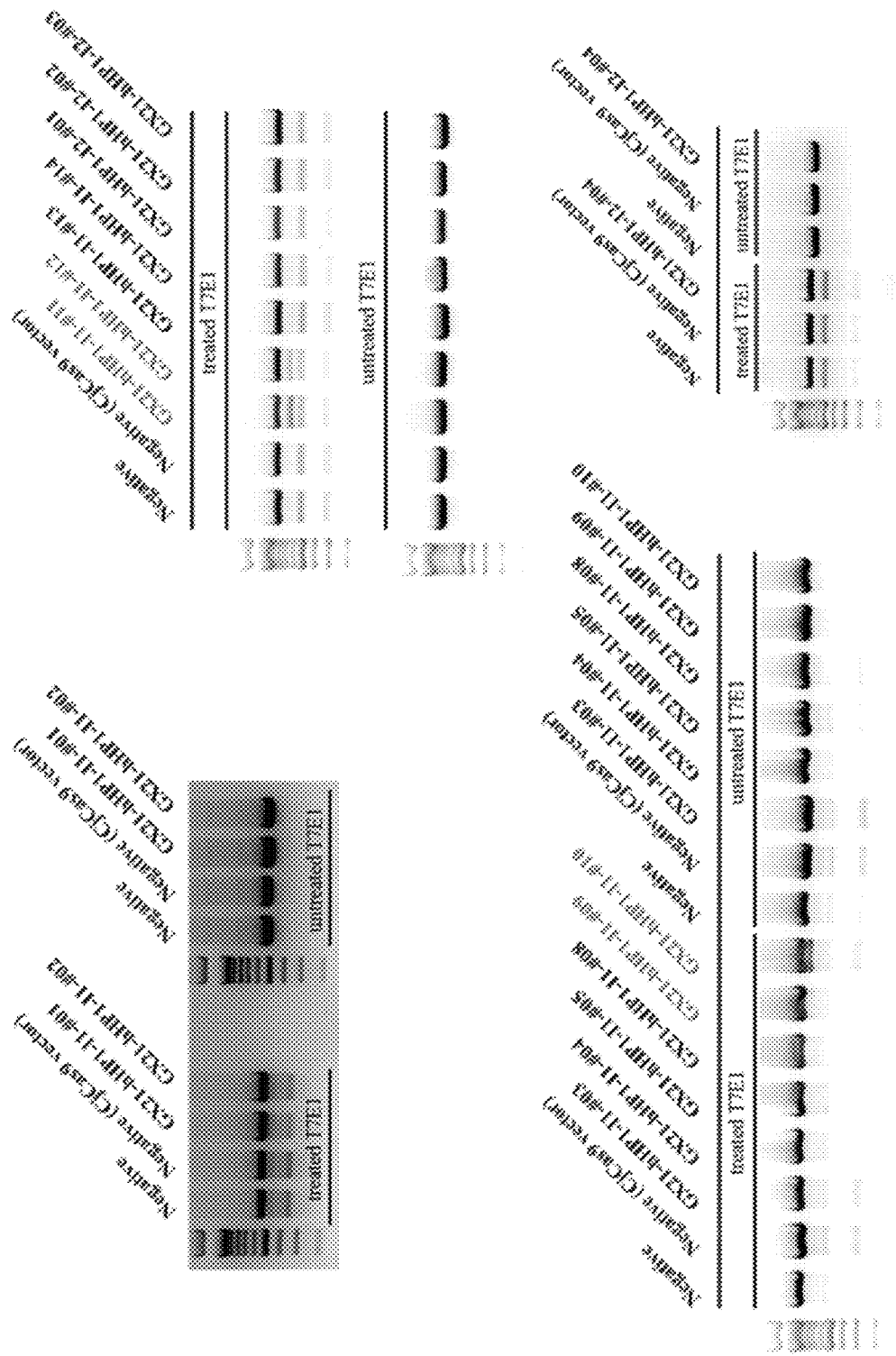
FIG. 3 shows the result of T7E1 assay for confirming the activity of gRNA targeting haptoglobin (HP).

As shown in FIG. 3, the gRNA activity was investigated for the target sequences #1 to 11, shown in Table 2, of the HP gene with Cjcas9, T7E1 activity was shown in target sequences #8, 9, 10 and 11.

3.2 Confirmation of Indel Ratio (%) of Target Sequence

Afterward, reads obtained by paired sequencing were analyzed to evaluate the activity of gRNAs by detecting insertion or deletion (Indels) at the on-target site on a genome, and the result is shown in Tables 2, 3, 4 and 5.

As shown in Tables 2 and 4, it was confirmed that all Indels occur in the corresponding target sequence of the HP gene, and an Indel ratio (%) was up to 86.4%, confirming high gene editing efficiency.

Also, in Tables 3 and 5, it was confirmed that all Indels occur in the corresponding target sequence of the APOC3 gene, and an Indel ratio (%) was up to 96.2%, confirming high gene editing efficiency.

DNA target sites of those with high activity according to the type of Cas9 among the gRNAs targeting respective genes were marked with a bold letter.

3.3 Off-Target Analysis

For off-target analysis of the selected gRNA, first, by an in-silico method using Cas-Offinder of CRISPR RGEN Tools, off-target lists with 3-base mismatches were selected, a mutation of a specific site in a genome corresponding to each off-target was verified in the human cell line HEK293 by targeted-deep sequencing.

Second, total human genomic DNA treated with gRNA and a Cas9 protein overnight at 37° C. was subjected to whole genome sequencing, and then potential lists were secured by Digenome-seq. Afterward, a mutation of a specific site in the genome of each off-target candidate was verified from the human cell line HEK293 by targeted-deep sequencing.

Figure 4:
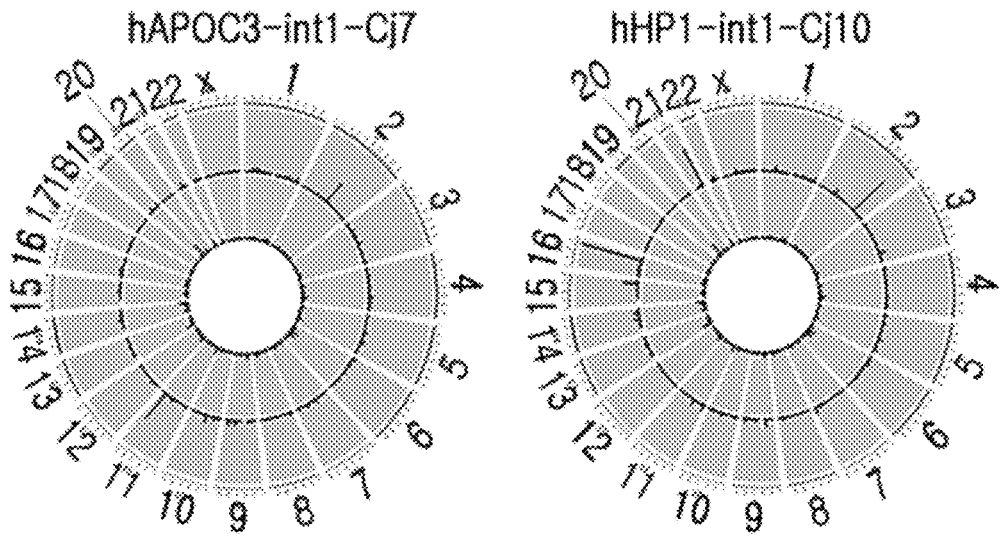
FIG. 4 is a set of graphs confirming an off-target site using Digenome-seq. The off-target sites for hAPOC3-int1-Cj7 are represented as SEQ ID NOs: 349-355. The off-target sites for hHP1-int1-Cj10 are represented as SEQ ID NOs: 356-366.
Figure 5:
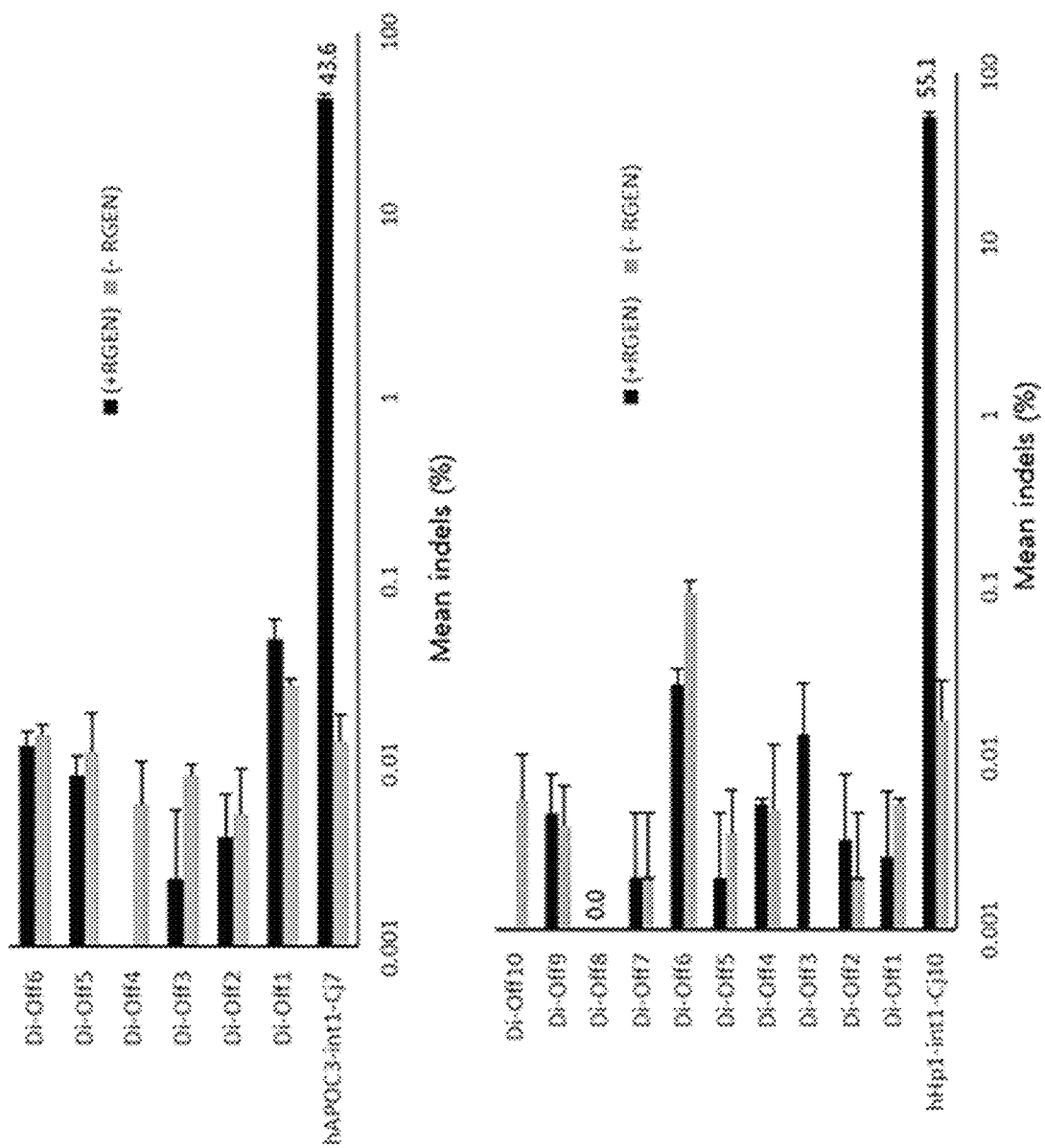
FIG. 5 is a set of graphs verifying off-target activity through targeted deep sequencing using NGS in a human cell line, that is, HEK293 cells.

As shown in FIGS. 4 and 5, as a result of deep sequencing which detects ten off-targets for HP1-Cj and six off-targets for APOC3-Cj, there was no significant off-target, and it was confirmed that indel mutations occurred with high efficiency.

Example 4: Construction of Vectors and Donors

For SpCas9 application, a vector (pAAV-EFS-SpCas9) including EFS, which is a promoter for mammalian expression, human codon-optimized SpCas9 with NLS and HA tag at the C- or N-terminus and BGHA and a vector (pAAV-hF9-donor-U6-sgRNA) including a U6 promoter, a sgRNA sequence and a human codon-optimized F9 donor between inverted tandem repeats (ITRs) of AAV2 were individually synthesized and constructed.

For CjCas9 application, a vector (pAAV-CMV-CjCas9-U6-sgRNA) including CMV, which is a promoter for mammalian expression, human codon-optimized CjCas9 with NLS and HA tag at the C- or N-terminus and BGHA, a U6 promoter and an sgRNA sequence, and a vector (pAAV-hF9-donor) including a human codon-optimized F9 donor were individually synthesized and constructed between AAV2 ITRs. That is, for CjCas9, in consideration of AAV packaging capacity, U6 and sgRNA may be delivered with a Cas9-expressed sequence.

Figure 6:
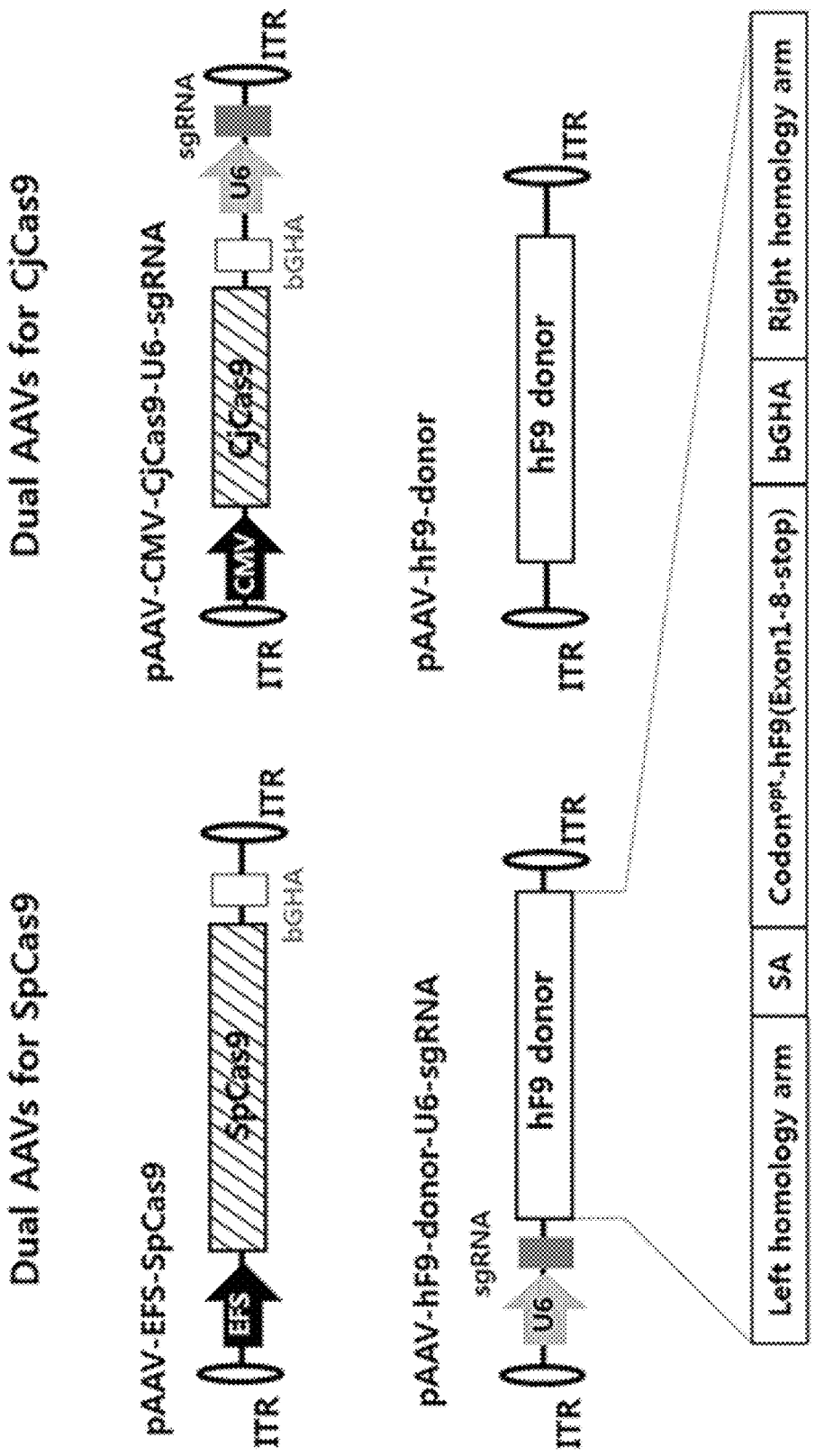
FIG. 6 is a diagram showing the packaging of CRISPR-SpCas9 or CRISPR-CjCas9 and the F9 gene in dual AAV.
Figure 7:
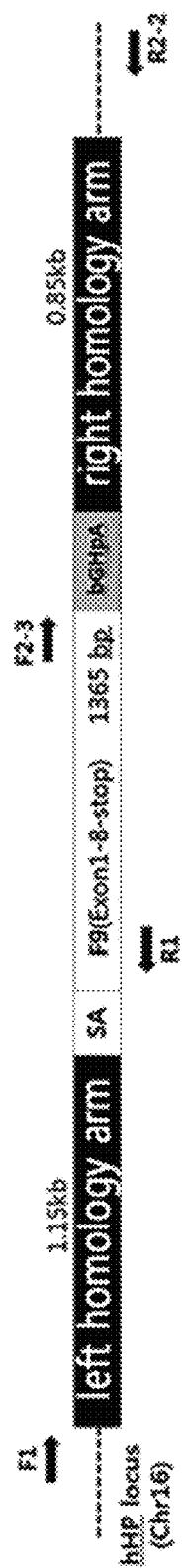
FIG. 7 shows a primer design for confirming HDR-mediated knock-in of the F9 gene to the hHP gene, which is obtained by Sanger sequencing confirming whether knock-in of the F9 therapeutic gene occurs in the genomic DNA of a HEK293 cell line into which pAAV-CMV-CjCas9-U6-sgRNA and pAAV-hF9-donor are transfected.

The donor introduced into each vector consists of splicing acceptor (SA)-human codon-optimized F9-bGHA between homology arms, each of which is 800 to 1200-bp long, present at both sides of a double-stranded break generated by Cas9, in a human HP1 or APOC3 genome (FIG. 6).

Example 5: Confirmation of HDR for Human Cell Line 500 ng of pAAV-CMV-CjCas9-U6-sgRNA targeting a human HP1 genome and 500 ng of pAAV-hF9-donor were transfected into HEK293 cell lines with Lipofectamine 2000.

After 3 days, genomic DNA was extracted, PCR bands were obtained with respective primers from the outer region of homology arms of a HP1 target site and the region knocked-in by HDR, and cloned into TA vectors.

Subsequently, a plasmid was extracted from the produced colony, and subjected to Sanger sequencing to confirm the sequences of knocked-in junctions at both sides.

Figure 8:
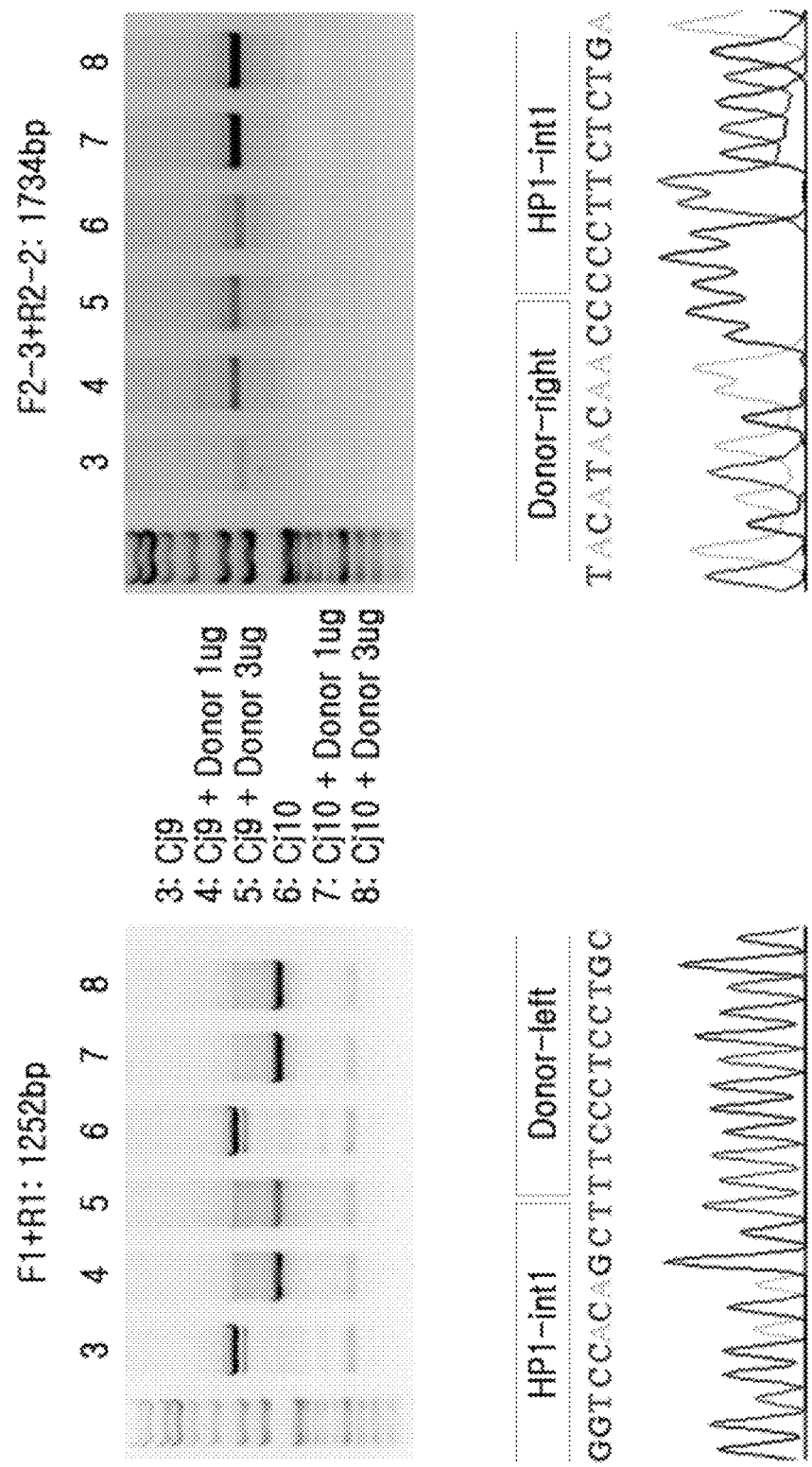
FIG. 8 is a set of graphs showing the F9 insertion between the left arm of homology arms and the hHP gene (left graph), and the F9 insertion between the right arm of homology arms and the hHP gene (right graph).

FIG. 8 shows the result of confirming knock-in at junctions of a left arm and a right arm, and knock-in, which occurs without modification of the F9 sequence, exactly in a region with a double-stranded break was confirmed at both arms. The gRNA sequences were Cj9: 5'-TCCAG-GAAAGAGAAACCTCCC-3' (SEQ ID NO: 409), and Cj10: 5'-CATTCAGGAAAGTACATTGGC-3' (SEQ ID NO: 410).

Example 6: AAV Construction

To produce AAV, a vector for a pseudo type AAV capsid, constructed pAAV-EFS-SpCas9, pAAV-hF9-donor-U6-sgRNA, pAAV-CMV-CjCas9-U6-sgRNA or pAAV-hF9-donor and a pHelper vector were simultaneously transfected into HEK293 cells at a molar ratio of 1:1:1.

After 72 hours, virus particles obtained by cell fusion were isolated and purified with iodixanol (Sigma-Aldrich) using a step-gradient ultracentrifuge, and the quantitative analysis of AAVs was performed through titration using qPCR.

Example 7: Confirmation of High Expression of Indels and KI (Knocked in) Genes from Hepatocytes $6 \times 10^5$ hepatocytes were maintained in a 24-well plate, and then infected with $5 \times 10^{11}$ ug of AAV6-EFS-SpCas9 and $5 \times 10^{11}$ ug of AAV6-hF9-donor-APOC3-Sp.

As the sequence of APOC3-Sp target, 5'-CCTAAGCCT-GAAGAATGAGG-3' (SEQ ID NO: 176) was used. On the day after infection (2D), the medium was changed, at 5D, 8D, and finally at 10D, culture supernatant samples were prepared, and at the final 10D, genomic DNA was extracted from hepatocytes.

Using a primer set (Forward: 5'-ACGGAAAATAT-CAAGAAGTA-3' (SEQ ID NO: 411), Reverse: 5'-CAGCAAGCCCTGTCCTGCTGG-3' (SEQ ID NO: 412)), an amplicon for the on-target of APOC3-Sp was obtained, additional PCR that attaches primer-specific adaptors and TruSeq HT Dual Index primers was performed.

Then, reads obtained through paired sequencing were analyzed to evaluate CRISPR activity by detection of Indels at an on-target genome position.

High expression of knock-in human F9 was detected by ELISA for the F9 protein secreted from a hepatocyte culture supernatant using a factor IX Human ELISA kit (Abcam).

Figure 9A:
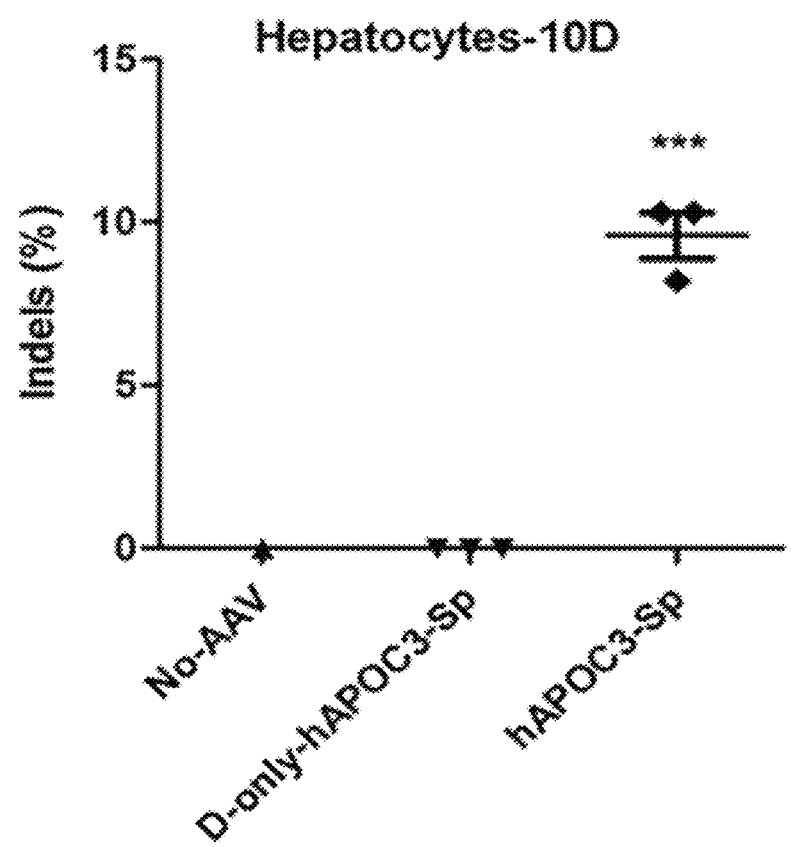
FIGS. 9A and 9B are a set of graphs showing on-target activity using genomic DNA (FIG. 9A), and a secretion level of hF9, obtained by knock-in using a supernatant sample (FIG. 9B), when dual AAV of AV6-EFS-SpCas9 ($5 \times 10^{\wedge}11$ μg) and AAV6-hF9-donor-APOC3-Sp ($5 \times 10^{\wedge}11$ μg) is introduced into human primary hepatocytes.

As shown in FIG. 9A, compared to a non-AAV-treated control group and a donor-only group (D-only-hAPOC3-Sp), a dual AAV-treated group (hAPOC3-Sp) showed an average of 9.6% indels.

Figure 9B:
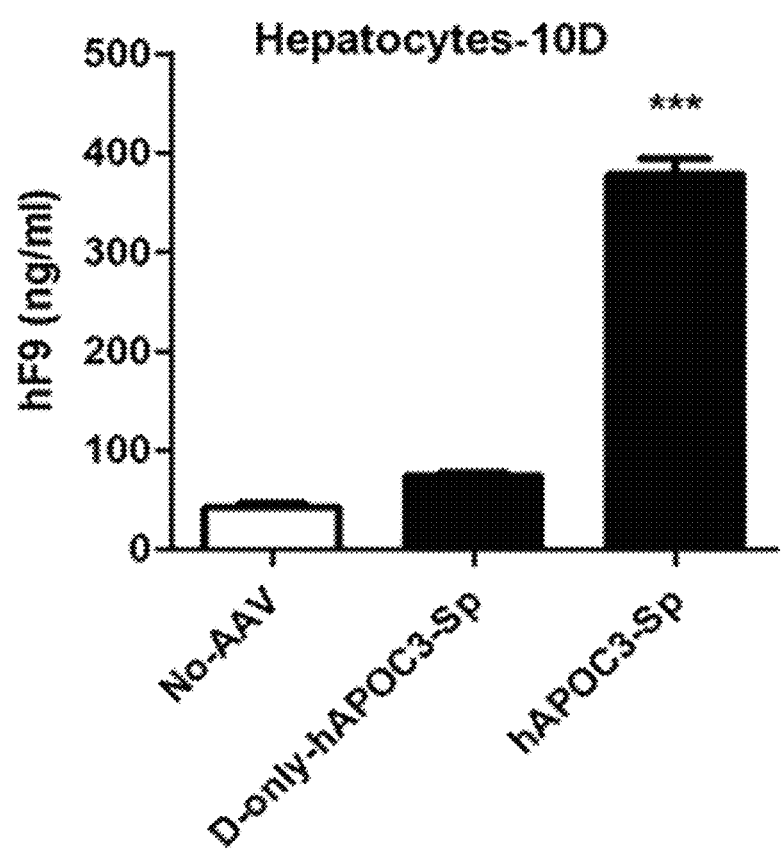

In addition, as shown in FIG. 9B, the secretion level of hF9 averaged 42.5 ng/ml in a control group, 74.1 ng/ml in a donor-only group, and 378.2 ng/ml in a dual AAV-treated group.

For statistical analysis, a Student's t-test was used. For significance, represents $p<0.05$,  represents $p<0.01$, and * represents $p<0.001$.

Sequence Listing Free Text

SEQ ID NO: 1 to SEQ ID NO: 15 represent the target sequence listings for the HP gene.

SEQ ID NO: 154 to SEQ ID NO: 348 represent the target sequence listings for the APOC3 gene.

This application contains references to amino acid sequences and/or nucleic acid sequences which have been submitted herewith as the sequence listing text file entitled "00008usnp_SequenceListing.txt," file size 64 kilobytes (KB), created on 20 Jan. 2023. The aforementioned sequence listing is hereby incorporated by reference in its entirety pursuant to 37 C.F.R. § 1.52(e).

What is claimed is:

1. A Liver bio-factory platform (LBP) system for expressing a transgene comprising,
    an engineered hepatocyte including the transgene artificially inserted in a region encoding a highly expressed and secretory gene on a genome of hepatocyte,
    wherein the highly expressed and secretory gene is haptoglobin (HP) gene present in the genome of hepatocytes,
    wherein the transgene is expressed higher compared to before insertion, or the transgene is newly expressed in hepatocyte, and
    wherein a protein produced by expressing the transgene is present in the hepatocyte or secreted out of the hepatocyte.

2. The LBP system of claim 1, wherein the transgene is expressed by an endogenous promoter in the genome of hepatocytes.

3. The LBP system of claim 1, wherein the transgene is F9 gene, GFP gene, F8 gene, or GBA gene.

4. The LBP of claim 1, wherein the transgene is inserted in a region encoding an intron of HP gene.

5. The LBP system of claim 1, wherein the transgene is inserted in a region encoding an intron 1 of HP gene.

6. The LBP system of claim 1, wherein the transgene is inserted in the region encoding an intron 2 of HP gene.

7. The LBP system of claim 1, wherein the transgene is inserted into a site which is present within one or more sequences selected from SEQ ID NOs: 1-153 and its complementary sequence of wild type HP gene.

8. The LBP system of claim 7, wherein the site is present within one or more sequences selected from SEQ ID NOs: 1-36, 41-153, and its complementary sequence of wild type HP gene of hepatocyte.

9. The LBP system of claim 7, wherein the site is present within one or more sequences selected from SEQ ID NOs: 1-11, 41-51 and its complementary sequence of wild type HP gene of hepatocyte.

10. The LBP system of claim 7, wherein the site is present within one or more sequences selected from SEQ ID NOs: 37-40 and its complementary sequence of wild type HP gene of hepatocyte.

11. The LBP system of claim 1, wherein HP gene of the engineered hepatocyte does not comprise one or more sequences same as a consecutive sequence selected from SEQ ID NOs: 1-153.

12. The LBP system of claim 1, wherein HP gene of the engineered hepatocyte does not comprise one or more sequences same as a consecutive sequence selected from SEQ ID NOs: 1-36 and 41-153.

13. The LBP system of claim 1, wherein HP gene of the engineered hepatocyte does not comprise one or more sequences same as a consecutive sequence selected from SEQ ID NOs: 1-11 and 41-51.

14. The LBP system of claim 1, wherein HP gene of the engineered hepatocyte does not comprise one or more sequences same as a consecutive sequence selected from SEQ ID NOs: 37-40.

15. The LBP system of claim 1, wherein a protein produced by expressing the transgene is present in the engineered hepatocyte or secreted out of the engineered hepatocyte.

* * * * *

SEQUENCE LISTING

<160> NUMBER OF SEQ ID NOS: 413

<210> SEQ ID NO 1
<211> LENGTH: 22
<212> TYPE: DNA
<213> ORGANISM: Homo sapiens

<400> SEQUENCE: 1
aaagaggaaa atatctgcta at                                              22

<210> SEQ ID NO 2
<211> LENGTH: 22
<212> TYPE: DNA
<213> ORGANISM: Homo sapiens

<400> SEQUENCE: 2
aaggcactta gatcttataa aa                                              22

<210> SEQ ID NO 3
<211> LENGTH: 22
<212> TYPE: DNA
<213> ORGANISM: Homo sapiens

<400> SEQUENCE: 3
ttctattaaa atagtttcta gg                                              22

<210> SEQ ID NO 4
<211> LENGTH: 22
<212> TYPE: DNA
<213> ORGANISM: Homo sapiens

<400> SEQUENCE: 4
ctcactaaca aatgccaacc at                                              22

<210> SEQ ID NO 5
<211> LENGTH: 22
<212> TYPE: DNA
<213> ORGANISM: Homo sapiens

<400> SEQUENCE: 5
ttagtgagat ggtgaactgg ca                                              22

<210> SEQ ID NO 6
<211> LENGTH: 22
<212> TYPE: DNA
<213> ORGANISM: Homo sapiens

<400> SEQUENCE: 6
aggtgaatta ttataaaata ct                                              22

<210> SEQ ID NO 7
<211> LENGTH: 22
<212> TYPE: DNA
<213> ORGANISM: Homo sapiens

<400> SEQUENCE: 7
ggaaaatatc aagaagtaga gg                                              22

<210> SEQ ID NO 8
<211> LENGTH: 22
<212> TYPE: DNA
<213> ORGANISM: Homo sapiens

<400> SEQUENCE: 8
ctccaggaaa gagaaacctc cc                                              22

<210> SEQ ID NO 9
<211> LENGTH: 22
<212> TYPE: DNA
<213> ORGANISM: Homo sapiens

<400> SEQUENCE: 9
gcattcagga aagtacattg gc                                              22

<210> SEQ ID NO 10
<211> LENGTH: 22
<212> TYPE: DNA
<213> ORGANISM: Homo sapiens

<400> SEQUENCE: 10
gaaattgccc ccacacctgc cc                                              22

<210> SEQ ID NO 11
<211> LENGTH: 22
<212> TYPE: DNA
<213> ORGANISM: Homo sapiens

<400> SEQUENCE: 11
aagaaattgc ccccacacct gc                                              22

<210> SEQ ID NO 12
<211> LENGTH: 22
<212> TYPE: DNA
<213> ORGANISM: Homo sapiens

<400> SEQUENCE: 12
tcaaaaatgt aacctgaagg aa                                              22

<210> SEQ ID NO 13
<211> LENGTH: 22
<212> TYPE: DNA
<213> ORGANISM: Homo sapiens

<400> SEQUENCE: 13
tagcagatat tttcctcttt aa                                              22

<210> SEQ ID NO 14
<211> LENGTH: 22
<212> TYPE: DNA
<213> ORGANISM: Homo sapiens

<400> SEQUENCE: 14
atgtgttact attagtcttc ct                                              22

<210> SEQ ID NO 15
<211> LENGTH: 22
<212> TYPE: DNA
<213> ORGANISM: Homo sapiens

<400> SEQUENCE: 15
atgtacaata aggaagacta at                                              22

<210> SEQ ID NO 16
<211> LENGTH: 22
<212> TYPE: DNA
<213> ORGANISM: Homo sapiens

```
<400> SEQUENCE: 16
acacaattaa ttgactagta cc                                              22

<210> SEQ ID NO 17
<211> LENGTH: 22
<212> TYPE: DNA
<213> ORGANISM: Homo sapiens

<400> SEQUENCE: 17
acaattaatt gactagtacc tg                                              22

<210> SEQ ID NO 18
<211> LENGTH: 22
<212> TYPE: DNA
<213> ORGANISM: Homo sapiens

<400> SEQUENCE: 18
aattaattga ctagtacctg gg                                              22

<210> SEQ ID NO 19
<211> LENGTH: 22
<212> TYPE: DNA
<213> ORGANISM: Homo sapiens

<400> SEQUENCE: 19
atcccaggta ttagtgtgta tc                                              22

<210> SEQ ID NO 20
<211> LENGTH: 22
<212> TYPE: DNA
<213> ORGANISM: Homo sapiens

<400> SEQUENCE: 20
ttgactagta cctgggatac ac                                              22

<210> SEQ ID NO 21
<211> LENGTH: 22
<212> TYPE: DNA
<213> ORGANISM: Homo sapiens

<400> SEQUENCE: 21
acctgggata cacactaata cc                                              22

<210> SEQ ID NO 22
<211> LENGTH: 22
<212> TYPE: DNA
<213> ORGANISM: Homo sapiens

<400> SEQUENCE: 22
taatacctgg gatacatcta at                                              22

<210> SEQ ID NO 23
<211> LENGTH: 22
<212> TYPE: DNA
<213> ORGANISM: Homo sapiens

<400> SEQUENCE: 23
atttcctaaa ggtgaattat ta                                              22

<210> SEQ ID NO 24
<211> LENGTH: 22
<212> TYPE: DNA
```

```
<213> ORGANISM: Homo sapiens

<400> SEQUENCE: 24
aaggttcctt aaatatataa tt                                            22

<210> SEQ ID NO 25
<211> LENGTH: 22
<212> TYPE: DNA
<213> ORGANISM: Homo sapiens

<400> SEQUENCE: 25
tggagggctc ctgtattatt gc                                            22

<210> SEQ ID NO 26
<211> LENGTH: 22
<212> TYPE: DNA
<213> ORGANISM: Homo sapiens

<400> SEQUENCE: 26
ctcagtttct ggctgcattc ag                                            22

<210> SEQ ID NO 27
<211> LENGTH: 22
<212> TYPE: DNA
<213> ORGANISM: Homo sapiens

<400> SEQUENCE: 27
catacacact ttagcagctt ct                                            22

<210> SEQ ID NO 28
<211> LENGTH: 22
<212> TYPE: DNA
<213> ORGANISM: Homo sapiens

<400> SEQUENCE: 28
ccaagaaatt gcccccacac ct                                            22

<210> SEQ ID NO 29
<211> LENGTH: 22
<212> TYPE: DNA
<213> ORGANISM: Homo sapiens

<400> SEQUENCE: 29
agtgctagga ccaagaaatt gc                                            22

<210> SEQ ID NO 30
<211> LENGTH: 22
<212> TYPE: DNA
<213> ORGANISM: Homo sapiens

<400> SEQUENCE: 30
ggtgtggggg caatttcttg gt                                            22

<210> SEQ ID NO 31
<211> LENGTH: 22
<212> TYPE: DNA
<213> ORGANISM: Homo sapiens

<400> SEQUENCE: 31
atccacacac acatgcatgt ac                                            22

<210> SEQ ID NO 32
<211> LENGTH: 22
```

<212> TYPE: DNA
<213> ORGANISM: Homo sapiens

<400> SEQUENCE: 32
gcatccacac acacatgcat gt                                              22

<210> SEQ ID NO 33
<211> LENGTH: 22
<212> TYPE: DNA
<213> ORGANISM: Homo sapiens

<400> SEQUENCE: 33
atgcatccac acacacatgc at                                              22

<210> SEQ ID NO 34
<211> LENGTH: 22
<212> TYPE: DNA
<213> ORGANISM: Homo sapiens

<400> SEQUENCE: 34
gcatgcatcc acacacacat gc                                              22

<210> SEQ ID NO 35
<211> LENGTH: 22
<212> TYPE: DNA
<213> ORGANISM: Homo sapiens

<400> SEQUENCE: 35
atgcatgcat ccacacacac at                                              22

<210> SEQ ID NO 36
<211> LENGTH: 22
<212> TYPE: DNA
<213> ORGANISM: Homo sapiens

<400> SEQUENCE: 36
tggaaagcta gtctccctgc tt                                              22

<210> SEQ ID NO 37
<211> LENGTH: 21
<212> TYPE: DNA
<213> ORGANISM: Homo sapiens

<400> SEQUENCE: 37
agacccgaga gggtcagagt g                                               21

<210> SEQ ID NO 38
<211> LENGTH: 21
<212> TYPE: DNA
<213> ORGANISM: Homo sapiens

<400> SEQUENCE: 38
atcccactct gaccctctcg g                                               21

<210> SEQ ID NO 39
<211> LENGTH: 21
<212> TYPE: DNA
<213> ORGANISM: Homo sapiens

<400> SEQUENCE: 39
tctcgggtct gcactctctc t                                               21

<210> SEQ ID NO 40

```
<211> LENGTH: 21
<212> TYPE: DNA
<213> ORGANISM: Homo sapiens

<400> SEQUENCE: 40
agggcactgg ctgaatccac t                                              21

<210> SEQ ID NO 41
<211> LENGTH: 20
<212> TYPE: DNA
<213> ORGANISM: Homo sapiens

<400> SEQUENCE: 41
ggttacattt ttgactttat                                                20

<210> SEQ ID NO 42
<211> LENGTH: 20
<212> TYPE: DNA
<213> ORGANISM: Homo sapiens

<400> SEQUENCE: 42
ctgggataca cactaatacc                                                20

<210> SEQ ID NO 43
<211> LENGTH: 20
<212> TYPE: DNA
<213> ORGANISM: Homo sapiens

<400> SEQUENCE: 43
gcaagtagtg cccgaatggt                                                20

<210> SEQ ID NO 44
<211> LENGTH: 20
<212> TYPE: DNA
<213> ORGANISM: Homo sapiens

<400> SEQUENCE: 44
ttgttagtga gatggtgaac                                                20

<210> SEQ ID NO 45
<211> LENGTH: 20
<212> TYPE: DNA
<213> ORGANISM: Homo sapiens

<400> SEQUENCE: 45
gaactggcag acggcacctg                                                20

<210> SEQ ID NO 46
<211> LENGTH: 20
<212> TYPE: DNA
<213> ORGANISM: Homo sapiens

<400> SEQUENCE: 46
aactggcaga cggcacctgt                                                20

<210> SEQ ID NO 47
<211> LENGTH: 20
<212> TYPE: DNA
<213> ORGANISM: Homo sapiens

<400> SEQUENCE: 47
ctcagacacc gcaaagatag                                                20
```

```
<210> SEQ ID NO 48
<211> LENGTH: 20
<212> TYPE: DNA
<213> ORGANISM: Homo sapiens

<400> SEQUENCE: 48
cactatcttt gcggtgtctg                                               20

<210> SEQ ID NO 49
<211> LENGTH: 20
<212> TYPE: DNA
<213> ORGANISM: Homo sapiens

<400> SEQUENCE: 49
actatctttg cggtgtctga                                               20

<210> SEQ ID NO 50
<211> LENGTH: 20
<212> TYPE: DNA
<213> ORGANISM: Homo sapiens

<400> SEQUENCE: 50
atctttgcgg tgtctgaggg                                               20

<210> SEQ ID NO 51
<211> LENGTH: 20
<212> TYPE: DNA
<213> ORGANISM: Homo sapiens

<400> SEQUENCE: 51
agaaaggcac ataggtggag                                               20

<210> SEQ ID NO 52
<211> LENGTH: 20
<212> TYPE: DNA
<213> ORGANISM: Homo sapiens

<400> SEQUENCE: 52
gcagaaatag aacaaagaaa                                               20

<210> SEQ ID NO 53
<211> LENGTH: 20
<212> TYPE: DNA
<213> ORGANISM: Homo sapiens

<400> SEQUENCE: 53
agaacaaaga aacgggcaaa                                               20

<210> SEQ ID NO 54
<211> LENGTH: 20
<212> TYPE: DNA
<213> ORGANISM: Homo sapiens

<400> SEQUENCE: 54
gaacaaagaa acgggcaaat                                               20

<210> SEQ ID NO 55
<211> LENGTH: 20
<212> TYPE: DNA
<213> ORGANISM: Homo sapiens

<400> SEQUENCE: 55
caggagtgtc tttttccttc                                               20
```

-continued

```
<210> SEQ ID NO 56
<211> LENGTH: 20
<212> TYPE: DNA
<213> ORGANISM: Homo sapiens

<400> SEQUENCE: 56
aagtcaaaaa tgtaacctga                                               20

<210> SEQ ID NO 57
<211> LENGTH: 20
<212> TYPE: DNA
<213> ORGANISM: Homo sapiens

<400> SEQUENCE: 57
gttacatttt tgactttata                                               20

<210> SEQ ID NO 58
<211> LENGTH: 20
<212> TYPE: DNA
<213> ORGANISM: Homo sapiens

<400> SEQUENCE: 58
gatgccagga agcctaccac                                               20

<210> SEQ ID NO 59
<211> LENGTH: 20
<212> TYPE: DNA
<213> ORGANISM: Homo sapiens

<400> SEQUENCE: 59
ggatgccagg aagcctacca                                               20

<210> SEQ ID NO 60
<211> LENGTH: 20
<212> TYPE: DNA
<213> ORGANISM: Homo sapiens

<400> SEQUENCE: 60
ataaatatac tcaggatgcc                                               20

<210> SEQ ID NO 61
<211> LENGTH: 20
<212> TYPE: DNA
<213> ORGANISM: Homo sapiens

<400> SEQUENCE: 61
atctgctaat aaatatactc                                               20

<210> SEQ ID NO 62
<211> LENGTH: 20
<212> TYPE: DNA
<213> ORGANISM: Homo sapiens

<400> SEQUENCE: 62
cttattgtac atttttaaag                                               20

<210> SEQ ID NO 63
<211> LENGTH: 20
<212> TYPE: DNA
<213> ORGANISM: Homo sapiens

<400> SEQUENCE: 63
ctctttaaaa atgtacaata                                               20
```

<210> SEQ ID NO 64
<211> LENGTH: 20
<212> TYPE: DNA
<213> ORGANISM: Homo sapiens

<400> SEQUENCE: 64
acaattaatt gactagtacc                                               20

<210> SEQ ID NO 65
<211> LENGTH: 20
<212> TYPE: DNA
<213> ORGANISM: Homo sapiens

<400> SEQUENCE: 65
caattaattg actagtacct                                               20

<210> SEQ ID NO 66
<211> LENGTH: 20
<212> TYPE: DNA
<213> ORGANISM: Homo sapiens

<400> SEQUENCE: 66
caggtattag tgtgtatccc                                               20

<210> SEQ ID NO 67
<211> LENGTH: 20
<212> TYPE: DNA
<213> ORGANISM: Homo sapiens

<400> SEQUENCE: 67
tgggatacac actaatacct                                               20

<210> SEQ ID NO 68
<211> LENGTH: 20
<212> TYPE: DNA
<213> ORGANISM: Homo sapiens

<400> SEQUENCE: 68
gccttaatta gatgtatccc                                               20

<210> SEQ ID NO 69
<211> LENGTH: 20
<212> TYPE: DNA
<213> ORGANISM: Homo sapiens

<400> SEQUENCE: 69
acctgggata catctaatta                                               20

<210> SEQ ID NO 70
<211> LENGTH: 20
<212> TYPE: DNA
<213> ORGANISM: Homo sapiens

<400> SEQUENCE: 70
agtttctagg ccagacacgg                                               20

<210> SEQ ID NO 71
<211> LENGTH: 20
<212> TYPE: DNA
<213> ORGANISM: Homo sapiens

<400> SEQUENCE: 71
aatagtttct aggccagaca                                        20

<210> SEQ ID NO 72
<211> LENGTH: 20
<212> TYPE: DNA
<213> ORGANISM: Homo sapiens

<400> SEQUENCE: 72
agaagcaagt agtgcccgaa                                        20

<210> SEQ ID NO 73
<211> LENGTH: 20
<212> TYPE: DNA
<213> ORGANISM: Homo sapiens

<400> SEQUENCE: 73
ctaacaaatg ccaaccattc                                        20

<210> SEQ ID NO 74
<211> LENGTH: 20
<212> TYPE: DNA
<213> ORGANISM: Homo sapiens

<400> SEQUENCE: 74
actaacaaat gccaaccatt                                        20

<210> SEQ ID NO 75
<211> LENGTH: 20
<212> TYPE: DNA
<213> ORGANISM: Homo sapiens

<400> SEQUENCE: 75
gttggcattt gttagtgaga                                        20

<210> SEQ ID NO 76
<211> LENGTH: 20
<212> TYPE: DNA
<213> ORGANISM: Homo sapiens

<400> SEQUENCE: 76
tgagatggtg aactggcaga                                        20

<210> SEQ ID NO 77
<211> LENGTH: 20
<212> TYPE: DNA
<213> ORGANISM: Homo sapiens

<400> SEQUENCE: 77
ggccatgggc attgacccac                                        20

<210> SEQ ID NO 78
<211> LENGTH: 20
<212> TYPE: DNA
<213> ORGANISM: Homo sapiens

<400> SEQUENCE: 78
cacctgtggg tcaatgccca                                        20

<210> SEQ ID NO 79
<211> LENGTH: 20
<212> TYPE: DNA
<213> ORGANISM: Homo sapiens

<400> SEQUENCE: 79

-continued aaaagcagga cggtggccat						20

<210> SEQ ID NO 80
<211> LENGTH: 20
<212> TYPE: DNA
<213> ORGANISM: Homo sapiens

<400> SEQUENCE: 80
caaaagcagg acggtggcca						20

<210> SEQ ID NO 81
<211> LENGTH: 20
<212> TYPE: DNA
<213> ORGANISM: Homo sapiens

<400> SEQUENCE: 81
ggtgtccaaa agcaggacgg						20

<210> SEQ ID NO 82
<211> LENGTH: 20
<212> TYPE: DNA
<213> ORGANISM: Homo sapiens

<400> SEQUENCE: 82
actggtgtcc aaaagcagga						20

<210> SEQ ID NO 83
<211> LENGTH: 20
<212> TYPE: DNA
<213> ORGANISM: Homo sapiens

<400> SEQUENCE: 83
catggccacc gtcctgcttt						20

<210> SEQ ID NO 84
<211> LENGTH: 20
<212> TYPE: DNA
<213> ORGANISM: Homo sapiens

<400> SEQUENCE: 84
gagaactggt gtccaaaagc						20

<210> SEQ ID NO 85
<211> LENGTH: 20
<212> TYPE: DNA
<213> ORGANISM: Homo sapiens

<400> SEQUENCE: 85
ttggacacca gttctcttcc						20

<210> SEQ ID NO 86
<211> LENGTH: 20
<212> TYPE: DNA
<213> ORGANISM: Homo sapiens

<400> SEQUENCE: 86
tgaaacccca aaatgccaga						20

<210> SEQ ID NO 87
<211> LENGTH: 20
<212> TYPE: DNA
<213> ORGANISM: Homo sapiens

```
<400> SEQUENCE: 87
aataattcac ctttaggaaa                                               20

<210> SEQ ID NO 88
<211> LENGTH: 20
<212> TYPE: DNA
<213> ORGANISM: Homo sapiens

<400> SEQUENCE: 88
tttcagatac catttcctaa                                               20

<210> SEQ ID NO 89
<211> LENGTH: 20
<212> TYPE: DNA
<213> ORGANISM: Homo sapiens

<400> SEQUENCE: 89
ttttataata attcacctttt                                              20

<210> SEQ ID NO 90
<211> LENGTH: 20
<212> TYPE: DNA
<213> ORGANISM: Homo sapiens

<400> SEQUENCE: 90
atatataatt ttaaacacgt                                               20

<210> SEQ ID NO 91
<211> LENGTH: 20
<212> TYPE: DNA
<213> ORGANISM: Homo sapiens

<400> SEQUENCE: 91
aatatataat tttaaacacg                                               20

<210> SEQ ID NO 92
<211> LENGTH: 20
<212> TYPE: DNA
<213> ORGANISM: Homo sapiens

<400> SEQUENCE: 92
tgtttaaaat tatatattta                                               20

<210> SEQ ID NO 93
<211> LENGTH: 20
<212> TYPE: DNA
<213> ORGANISM: Homo sapiens

<400> SEQUENCE: 93 ttgatattttt ccgtaataaa                                              20

<210> SEQ ID NO 94
<211> LENGTH: 20
<212> TYPE: DNA
<213> ORGANISM: Homo sapiens

<400> SEQUENCE: 94
atttaaggaa cctttttatta                                              20

<210> SEQ ID NO 95
<211> LENGTH: 20
<212> TYPE: DNA
<213> ORGANISM: Homo sapiens
```

```
<400> SEQUENCE: 95
cggaaaatat caagaagtag                                       20

<210> SEQ ID NO 96
<211> LENGTH: 20
<212> TYPE: DNA
<213> ORGANISM: Homo sapiens

<400> SEQUENCE: 96
aactcagaga tgggaacttt                                       20

<210> SEQ ID NO 97
<211> LENGTH: 20
<212> TYPE: DNA
<213> ORGANISM: Homo sapiens

<400> SEQUENCE: 97
taactcagag atgggaactt                                       20

<210> SEQ ID NO 98
<211> LENGTH: 20
<212> TYPE: DNA
<213> ORGANISM: Homo sapiens

<400> SEQUENCE: 98
aatgtagata actcagagat                                       20

<210> SEQ ID NO 99
<211> LENGTH: 20
<212> TYPE: DNA
<213> ORGANISM: Homo sapiens

<400> SEQUENCE: 99
aaatgtagat aactcagaga                                       20

<210> SEQ ID NO 100
<211> LENGTH: 20
<212> TYPE: DNA
<213> ORGANISM: Homo sapiens

<400> SEQUENCE: 100
ttttattacc actatctttg                                       20

<210> SEQ ID NO 101
<211> LENGTH: 20
<212> TYPE: DNA
<213> ORGANISM: Homo sapiens

<400> SEQUENCE: 101
caataataca ggagccctcc                                       20

<210> SEQ ID NO 102
<211> LENGTH: 20
<212> TYPE: DNA
<213> ORGANISM: Homo sapiens

<400> SEQUENCE: 102
aagtacattg gcaataatac                                       20

<210> SEQ ID NO 103
<211> LENGTH: 20
<212> TYPE: DNA
```

```
<213> ORGANISM: Homo sapiens

<400> SEQUENCE: 103
ctgcattcag gaaagtacat                                               20

<210> SEQ ID NO 104
<211> LENGTH: 20
<212> TYPE: DNA
<213> ORGANISM: Homo sapiens

<400> SEQUENCE: 104
ctcagtttct ggctgcattc                                               20

<210> SEQ ID NO 105
<211> LENGTH: 20
<212> TYPE: DNA
<213> ORGANISM: Homo sapiens

<400> SEQUENCE: 105 ggagggtgg gctcagtttc                                                20

<210> SEQ ID NO 106
<211> LENGTH: 20
<212> TYPE: DNA
<213> ORGANISM: Homo sapiens

<400> SEQUENCE: 106
aggcacatag gtggaggggt                                               20

<210> SEQ ID NO 107
<211> LENGTH: 20
<212> TYPE: DNA
<213> ORGANISM: Homo sapiens

<400> SEQUENCE: 107
aaggcacata ggtggagggg                                               20

<210> SEQ ID NO 108
<211> LENGTH: 20
<212> TYPE: DNA
<213> ORGANISM: Homo sapiens

<400> SEQUENCE: 108
tagaaaggca cataggtgga                                               20

<210> SEQ ID NO 109
<211> LENGTH: 20
<212> TYPE: DNA
<213> ORGANISM: Homo sapiens

<400> SEQUENCE: 109
atagaaaggc acataggtgg                                               20

<210> SEQ ID NO 110
<211> LENGTH: 20
<212> TYPE: DNA
<213> ORGANISM: Homo sapiens

<400> SEQUENCE: 110
gggatagaaa ggcacatagg                                               20

<210> SEQ ID NO 111
<211> LENGTH: 20
```

```
<212> TYPE: DNA
<213> ORGANISM: Homo sapiens

<400> SEQUENCE: 111
agagggatag aaaggcacat                                              20

<210> SEQ ID NO 112
<211> LENGTH: 20
<212> TYPE: DNA
<213> ORGANISM: Homo sapiens

<400> SEQUENCE: 112
gcttctgcag aattcccagc                                              20

<210> SEQ ID NO 113
<211> LENGTH: 20
<212> TYPE: DNA
<213> ORGANISM: Homo sapiens

<400> SEQUENCE: 113
ccagcaagcc ctgtcctgct                                              20

<210> SEQ ID NO 114
<211> LENGTH: 20
<212> TYPE: DNA
<213> ORGANISM: Homo sapiens

<400> SEQUENCE: 114
tccagcaagc cctgtcctgc                                              20

<210> SEQ ID NO 115
<211> LENGTH: 20
<212> TYPE: DNA
<213> ORGANISM: Homo sapiens

<400> SEQUENCE: 115
tgcagaattc ccagcaggac                                              20

<210> SEQ ID NO 116
<211> LENGTH: 20
<212> TYPE: DNA
<213> ORGANISM: Homo sapiens

<400> SEQUENCE: 116
gcagaattcc cagcaggaca                                              20

<210> SEQ ID NO 117
<211> LENGTH: 20
<212> TYPE: DNA
<213> ORGANISM: Homo sapiens

<400> SEQUENCE: 117
cccagcagga cagggcttgc                                              20

<210> SEQ ID NO 118
<211> LENGTH: 20
<212> TYPE: DNA
<213> ORGANISM: Homo sapiens

<400> SEQUENCE: 118
gacagggctt gctggaagct                                              20

<210> SEQ ID NO 119
```

```
<211> LENGTH: 20
<212> TYPE: DNA
<213> ORGANISM: Homo sapiens

<400> SEQUENCE: 119
agaagctgct aaagtgtgta                                               20

<210> SEQ ID NO 120
<211> LENGTH: 20
<212> TYPE: DNA
<213> ORGANISM: Homo sapiens

<400> SEQUENCE: 120
gaagctgcta aagtgtgtat                                               20

<210> SEQ ID NO 121
<211> LENGTH: 20
<212> TYPE: DNA
<213> ORGANISM: Homo sapiens

<400> SEQUENCE: 121
ctgctaaagt gtgtatgggc                                               20

<210> SEQ ID NO 122
<211> LENGTH: 20
<212> TYPE: DNA
<213> ORGANISM: Homo sapiens

<400> SEQUENCE: 122
aaagtgtgta tgggcaggtg                                               20

<210> SEQ ID NO 123
<211> LENGTH: 20
<212> TYPE: DNA
<213> ORGANISM: Homo sapiens

<400> SEQUENCE: 123
aagtgtgtat gggcaggtgt                                               20

<210> SEQ ID NO 124
<211> LENGTH: 20
<212> TYPE: DNA
<213> ORGANISM: Homo sapiens

<400> SEQUENCE: 124
agtgtgtatg ggcaggtgtg                                               20

<210> SEQ ID NO 125
<211> LENGTH: 20
<212> TYPE: DNA
<213> ORGANISM: Homo sapiens

<400> SEQUENCE: 125
gtgtgtatgg gcaggtgtgg                                               20

<210> SEQ ID NO 126
<211> LENGTH: 20
<212> TYPE: DNA
<213> ORGANISM: Homo sapiens

<400> SEQUENCE: 126
caggtgtggg ggcaatttct                                               20
```

```
<210> SEQ ID NO 127
<211> LENGTH: 20
<212> TYPE: DNA
<213> ORGANISM: Homo sapiens

<400> SEQUENCE: 127
agtcgatata tggaagtgct                                                   20

<210> SEQ ID NO 128
<211> LENGTH: 20
<212> TYPE: DNA
<213> ORGANISM: Homo sapiens

<400> SEQUENCE: 128
cagaaaagaa agtcgatata                                                   20

<210> SEQ ID NO 129
<211> LENGTH: 20
<212> TYPE: DNA
<213> ORGANISM: Homo sapiens

<400> SEQUENCE: 129
catatatcga ctttcttttc                                                   20

<210> SEQ ID NO 130
<211> LENGTH: 20
<212> TYPE: DNA
<213> ORGANISM: Homo sapiens

<400> SEQUENCE: 130
tttcttttct ggctgctaag                                                   20

<210> SEQ ID NO 131
<211> LENGTH: 20
<212> TYPE: DNA
<213> ORGANISM: Homo sapiens

<400> SEQUENCE: 131
ttcttttctg gctgctaagt                                                   20

<210> SEQ ID NO 132
<211> LENGTH: 20
<212> TYPE: DNA
<213> ORGANISM: Homo sapiens

<400> SEQUENCE: 132
ttttctggct gctaagtggg                                                   20

<210> SEQ ID NO 133
<211> LENGTH: 20
<212> TYPE: DNA
<213> ORGANISM: Homo sapiens

<400> SEQUENCE: 133
actgcagaga gaagacaagg                                                   20

<210> SEQ ID NO 134
<211> LENGTH: 20
<212> TYPE: DNA
<213> ORGANISM: Homo sapiens

<400> SEQUENCE: 134
ggcactgcag agagaagaca                                                   20
```

```
<210> SEQ ID NO 135
<211> LENGTH: 20
<212> TYPE: DNA
<213> ORGANISM: Homo sapiens

<400> SEQUENCE: 135
tgaaggaaaa agacactcct                                              20

<210> SEQ ID NO 136
<211> LENGTH: 20
<212> TYPE: DNA
<213> ORGANISM: Homo sapiens

<400> SEQUENCE: 136
aggttacatt tttgacttta                                              20

<210> SEQ ID NO 137
<211> LENGTH: 20
<212> TYPE: DNA
<213> ORGANISM: Homo sapiens

<400> SEQUENCE: 137
gtggtaggct tcctggcatc                                              20

<210> SEQ ID NO 138
<211> LENGTH: 20
<212> TYPE: DNA
<213> ORGANISM: Homo sapiens

<400> SEQUENCE: 138
tatctgctaa taaatatact                                              20

<210> SEQ ID NO 139
<211> LENGTH: 20
<212> TYPE: DNA
<213> ORGANISM: Homo sapiens

<400> SEQUENCE: 139
gaagactaat agtaacacat                                              20

<210> SEQ ID NO 140
<211> LENGTH: 20
<212> TYPE: DNA
<213> ORGANISM: Homo sapiens

<400> SEQUENCE: 140
acaattaatt gactagtacc                                              20

<210> SEQ ID NO 141
<211> LENGTH: 20
<212> TYPE: DNA
<213> ORGANISM: Homo sapiens

<400> SEQUENCE: 141
ctgggataca cactaatacc                                              20

<210> SEQ ID NO 142
<211> LENGTH: 20
<212> TYPE: DNA
<213> ORGANISM: Homo sapiens

<400> SEQUENCE: 142
ttaatagaag caagtagtgc                                              20
```

<210> SEQ ID NO 143
<211> LENGTH: 20
<212> TYPE: DNA
<213> ORGANISM: Homo sapiens

<400> SEQUENCE: 143
tgaactggca gacggcacct                                              20

<210> SEQ ID NO 144
<211> LENGTH: 20
<212> TYPE: DNA
<213> ORGANISM: Homo sapiens

<400> SEQUENCE: 144
tcagatacca tttcctaaag                                              20

<210> SEQ ID NO 145
<211> LENGTH: 20
<212> TYPE: DNA
<213> ORGANISM: Homo sapiens

<400> SEQUENCE: 145
aaatatataa ttttaaacac                                              20

<210> SEQ ID NO 146
<211> LENGTH: 20
<212> TYPE: DNA
<213> ORGANISM: Homo sapiens

<400> SEQUENCE: 146
cggaaaatat caagaagtag                                              20

<210> SEQ ID NO 147
<211> LENGTH: 20
<212> TYPE: DNA
<213> ORGANISM: Homo sapiens

<400> SEQUENCE: 147
taagcccaaa gttcccatct                                              20

<210> SEQ ID NO 148
<211> LENGTH: 20
<212> TYPE: DNA
<213> ORGANISM: Homo sapiens

<400> SEQUENCE: 148
attattgcca atgtactttc                                              20

<210> SEQ ID NO 149
<211> LENGTH: 20
<212> TYPE: DNA
<213> ORGANISM: Homo sapiens

<400> SEQUENCE: 149
atagaaaggc acataggtgg                                              20

<210> SEQ ID NO 150
<211> LENGTH: 20
<212> TYPE: DNA
<213> ORGANISM: Homo sapiens

<400> SEQUENCE: 150
ccagcaagcc ctgtcctgct                                              20

<210> SEQ ID NO 151
<211> LENGTH: 20
<212> TYPE: DNA
<213> ORGANISM: Homo sapiens

<400> SEQUENCE: 151 tttctggct gctaagtggg                                               20

<210> SEQ ID NO 152
<211> LENGTH: 20
<212> TYPE: DNA
<213> ORGANISM: Homo sapiens

<400> SEQUENCE: 152
gtgtgtacat gcatgtgtgt                                              20

<210> SEQ ID NO 153
<211> LENGTH: 20
<212> TYPE: DNA
<213> ORGANISM: Homo sapiens

<400> SEQUENCE: 153
actgcagaga gaagacaagg                                              20

<210> SEQ ID NO 154
<211> LENGTH: 22
<212> TYPE: DNA
<213> ORGANISM: Homo sapiens

<400> SEQUENCE: 154
ccagcccagc cagcaagcct gg                                           22

<210> SEQ ID NO 155
<211> LENGTH: 22
<212> TYPE: DNA
<213> ORGANISM: Homo sapiens

<400> SEQUENCE: 155
cttcaggtta tgatgagggg tg                                           22

<210> SEQ ID NO 156
<211> LENGTH: 22
<212> TYPE: DNA
<213> ORGANISM: Homo sapiens

<400> SEQUENCE: 156
gggaggggtg tcacttgccc aa                                           22

<210> SEQ ID NO 157
<211> LENGTH: 22
<212> TYPE: DNA
<213> ORGANISM: Homo sapiens

<400> SEQUENCE: 157
accccctgtg tagctttggg ca                                           22

<210> SEQ ID NO 158
<211> LENGTH: 22
<212> TYPE: DNA
<213> ORGANISM: Homo sapiens

<400> SEQUENCE: 158

-continued aagcctgaag aatgaggggg ga    22

<210> SEQ ID NO 159
<211> LENGTH: 22
<212> TYPE: DNA
<213> ORGANISM: Homo sapiens

<400> SEQUENCE: 159
tggagagggc cagaaatcac cc    22

<210> SEQ ID NO 160
<211> LENGTH: 22
<212> TYPE: DNA
<213> ORGANISM: Homo sapiens

<400> SEQUENCE: 160
gagagggcca gaaatcaccc aa    22

<210> SEQ ID NO 161
<211> LENGTH: 22
<212> TYPE: DNA
<213> ORGANISM: Homo sapiens

<400> SEQUENCE: 161 gaaacccac cagactgaac at    22

<210> SEQ ID NO 162
<211> LENGTH: 22
<212> TYPE: DNA
<213> ORGANISM: Homo sapiens

<400> SEQUENCE: 162
aaggagtagg ggccggctcc ct    22

<210> SEQ ID NO 163
<211> LENGTH: 22
<212> TYPE: DNA
<213> ORGANISM: Homo sapiens

<400> SEQUENCE: 163
tggggacctg gggtgcccct ca    22

<210> SEQ ID NO 164
<211> LENGTH: 22
<212> TYPE: DNA
<213> ORGANISM: Homo sapiens

<400> SEQUENCE: 164
tcctgcaagg aagtgtcctg tg    22

<210> SEQ ID NO 165
<211> LENGTH: 22
<212> TYPE: DNA
<213> ORGANISM: Homo sapiens

<400> SEQUENCE: 165
ggaacagagg tgccatgcag cc    22

<210> SEQ ID NO 166
<211> LENGTH: 22
<212> TYPE: DNA
<213> ORGANISM: Homo sapiens

```
-continued

<400> SEQUENCE: 166
caacaaggag tacccggggc tg                                          22

<210> SEQ ID NO 167
<211> LENGTH: 22
<212> TYPE: DNA
<213> ORGANISM: Homo sapiens

<400> SEQUENCE: 167
gagcgccagg agggcaacaa ca                                          22

<210> SEQ ID NO 168
<211> LENGTH: 20
<212> TYPE: DNA
<213> ORGANISM: Homo sapiens

<400> SEQUENCE: 168
tctgctcagt tcatccctag                                             20

<210> SEQ ID NO 169
<211> LENGTH: 20
<212> TYPE: DNA
<213> ORGANISM: Homo sapiens

<400> SEQUENCE: 169
ctgctccagg taatgccctc                                             20

<210> SEQ ID NO 170
<211> LENGTH: 20
<212> TYPE: DNA
<213> ORGANISM: Homo sapiens

<400> SEQUENCE: 170
agaagcactt gctagagcta                                             20

<210> SEQ ID NO 171
<211> LENGTH: 20
<212> TYPE: DNA
<213> ORGANISM: Homo sapiens

<400> SEQUENCE: 171
ggggcacccg tccagctccg                                             20

<210> SEQ ID NO 172
<211> LENGTH: 20
<212> TYPE: DNA
<213> ORGANISM: Homo sapiens

<400> SEQUENCE: 172
cttcaggtta tgatgagggg                                             20

<210> SEQ ID NO 173
<211> LENGTH: 20
<212> TYPE: DNA
<213> ORGANISM: Homo sapiens

<400> SEQUENCE: 173
gttcttcagg ttatgatgag                                             20

<210> SEQ ID NO 174
<211> LENGTH: 20
<212> TYPE: DNA
<213> ORGANISM: Homo sapiens
```

```
<400> SEQUENCE: 174
cccgggcctc catgttcttc                                              20

<210> SEQ ID NO 175
<211> LENGTH: 20
<212> TYPE: DNA
<213> ORGANISM: Homo sapiens

<400> SEQUENCE: 175
aggttccccc ctcattcttc                                              20

<210> SEQ ID NO 176
<211> LENGTH: 20
<212> TYPE: DNA
<213> ORGANISM: Homo sapiens

<400> SEQUENCE: 176
cctaagcctg aagaatgagg                                              20

<210> SEQ ID NO 177
<211> LENGTH: 20
<212> TYPE: DNA
<213> ORGANISM: Homo sapiens

<400> SEQUENCE: 177
agccctaagc ctgaagaatg                                              20

<210> SEQ ID NO 178
<211> LENGTH: 20
<212> TYPE: DNA
<213> ORGANISM: Homo sapiens

<400> SEQUENCE: 178
gggtaggact gggctgtcta                                              20

<210> SEQ ID NO 179
<211> LENGTH: 20
<212> TYPE: DNA
<213> ORGANISM: Homo sapiens

<400> SEQUENCE: 179
agcccagtcc taccccagac                                              20

<210> SEQ ID NO 180
<211> LENGTH: 20
<212> TYPE: DNA
<213> ORGANISM: Homo sapiens

<400> SEQUENCE: 180
ggtgatttct ggccctctcc                                              20

<210> SEQ ID NO 181
<211> LENGTH: 20
<212> TYPE: DNA
<213> ORGANISM: Homo sapiens

<400> SEQUENCE: 181
cggagatcag tccagaccgc                                              20

<210> SEQ ID NO 182
<211> LENGTH: 20
<212> TYPE: DNA
```

<213> ORGANISM: Homo sapiens

<400> SEQUENCE: 182
gcgagggatc gaggcccaaa                                               20

<210> SEQ ID NO 183
<211> LENGTH: 20
<212> TYPE: DNA
<213> ORGANISM: Homo sapiens

<400> SEQUENCE: 183
tcctctttcc cctccccaga                                               20

<210> SEQ ID NO 184
<211> LENGTH: 20
<212> TYPE: DNA
<213> ORGANISM: Homo sapiens

<400> SEQUENCE: 184
ccaggtaatg ccctctgggg                                               20

<210> SEQ ID NO 185
<211> LENGTH: 20
<212> TYPE: DNA
<213> ORGANISM: Homo sapiens

<400> SEQUENCE: 185
ctcctctttc ccctccccag                                               20

<210> SEQ ID NO 186
<211> LENGTH: 20
<212> TYPE: DNA
<213> ORGANISM: Homo sapiens

<400> SEQUENCE: 186
caggtaatgc cctctgggga                                               20

<210> SEQ ID NO 187
<211> LENGTH: 20
<212> TYPE: DNA
<213> ORGANISM: Homo sapiens

<400> SEQUENCE: 187
aggtaatgcc ctctggggag                                               20

<210> SEQ ID NO 188
<211> LENGTH: 20
<212> TYPE: DNA
<213> ORGANISM: Homo sapiens

<400> SEQUENCE: 188
gccctctggg gaggggaaag                                               20

<210> SEQ ID NO 189
<211> LENGTH: 20
<212> TYPE: DNA
<213> ORGANISM: Homo sapiens

<400> SEQUENCE: 189
ctctggggag gggaaagagg                                               20

<210> SEQ ID NO 190
<211> LENGTH: 20

```
<212> TYPE: DNA
<213> ORGANISM: Homo sapiens

<400> SEQUENCE: 190 tctgggagg ggaaagagga                                              20

<210> SEQ ID NO 191
<211> LENGTH: 20
<212> TYPE: DNA
<213> ORGANISM: Homo sapiens

<400> SEQUENCE: 191
gggaggggaa agaggagggg                                             20

<210> SEQ ID NO 192
<211> LENGTH: 20
<212> TYPE: DNA
<213> ORGANISM: Homo sapiens

<400> SEQUENCE: 192
aggggaaaga ggaggggagg                                             20

<210> SEQ ID NO 193
<211> LENGTH: 20
<212> TYPE: DNA
<213> ORGANISM: Homo sapiens

<400> SEQUENCE: 193
aggaggggag gaggatgaag                                             20

<210> SEQ ID NO 194
<211> LENGTH: 20
<212> TYPE: DNA
<213> ORGANISM: Homo sapiens

<400> SEQUENCE: 194
ggaggggagg aggatgaaga                                             20

<210> SEQ ID NO 195
<211> LENGTH: 20
<212> TYPE: DNA
<213> ORGANISM: Homo sapiens

<400> SEQUENCE: 195
gaggggagga ggatgaagag                                             20

<210> SEQ ID NO 196
<211> LENGTH: 20
<212> TYPE: DNA
<213> ORGANISM: Homo sapiens

<400> SEQUENCE: 196
ggaggatgaa gaggggcaag                                             20

<210> SEQ ID NO 197
<211> LENGTH: 20
<212> TYPE: DNA
<213> ORGANISM: Homo sapiens

<400> SEQUENCE: 197
cttgctggct gggctgggca                                             20

<210> SEQ ID NO 198
```

-continued

```
<211> LENGTH: 20
<212> TYPE: DNA
<213> ORGANISM: Homo sapiens

<400> SEQUENCE: 198
gcttgctggc tgggctgggc                                         20

<210> SEQ ID NO 199
<211> LENGTH: 20
<212> TYPE: DNA
<213> ORGANISM: Homo sapiens

<400> SEQUENCE: 199
ccaggcttgc tggctgggct                                         20

<210> SEQ ID NO 200
<211> LENGTH: 20
<212> TYPE: DNA
<213> ORGANISM: Homo sapiens

<400> SEQUENCE: 200
tccaggcttg ctggctgggc                                         20

<210> SEQ ID NO 201
<211> LENGTH: 20
<212> TYPE: DNA
<213> ORGANISM: Homo sapiens

<400> SEQUENCE: 201
cttctccagg cttgctggct                                         20

<210> SEQ ID NO 202
<211> LENGTH: 20
<212> TYPE: DNA
<213> ORGANISM: Homo sapiens

<400> SEQUENCE: 202
gcttctccag gcttgctggc                                         20

<210> SEQ ID NO 203
<211> LENGTH: 20
<212> TYPE: DNA
<213> ORGANISM: Homo sapiens

<400> SEQUENCE: 203
aagtgcttct ccaggcttgc                                         20

<210> SEQ ID NO 204
<211> LENGTH: 20
<212> TYPE: DNA
<213> ORGANISM: Homo sapiens

<400> SEQUENCE: 204
cccagcccag ccagcaagcc                                         20

<210> SEQ ID NO 205
<211> LENGTH: 20
<212> TYPE: DNA
<213> ORGANISM: Homo sapiens

<400> SEQUENCE: 205
gctctagcaa gtgcttctcc                                         20
```

-continued

```
<210> SEQ ID NO 206
<211> LENGTH: 20
<212> TYPE: DNA
<213> ORGANISM: Homo sapiens

<400> SEQUENCE: 206 cctcccaga gggcattacc                                                  20

<210> SEQ ID NO 207
<211> LENGTH: 20
<212> TYPE: DNA
<213> ORGANISM: Homo sapiens

<400> SEQUENCE: 207
tgctagagct aaggaagcct                                                 20

<210> SEQ ID NO 208
<211> LENGTH: 20
<212> TYPE: DNA
<213> ORGANISM: Homo sapiens

<400> SEQUENCE: 208
agctaaggaa gcctcggagc                                                 20

<210> SEQ ID NO 209
<211> LENGTH: 20
<212> TYPE: DNA
<213> ORGANISM: Homo sapiens

<400> SEQUENCE: 209
tgctccaggt aatgccctct                                                 20

<210> SEQ ID NO 210
<211> LENGTH: 20
<212> TYPE: DNA
<213> ORGANISM: Homo sapiens

<400> SEQUENCE: 210
aaggaagcct cggagctgga                                                 20

<210> SEQ ID NO 211
<211> LENGTH: 20
<212> TYPE: DNA
<213> ORGANISM: Homo sapiens

<400> SEQUENCE: 211
aggaagcctc ggagctggac                                                 20

<210> SEQ ID NO 212
<211> LENGTH: 20
<212> TYPE: DNA
<213> ORGANISM: Homo sapiens

<400> SEQUENCE: 212
aggttatgat gagggtggg                                                  20

<210> SEQ ID NO 213
<211> LENGTH: 20
<212> TYPE: DNA
<213> ORGANISM: Homo sapiens

<400> SEQUENCE: 213
caggttatga tgagggtgg                                                  20
```

```
<210> SEQ ID NO 214
<211> LENGTH: 20
<212> TYPE: DNA
<213> ORGANISM: Homo sapiens

<400> SEQUENCE: 214
tcaggttatg atgagggtg                                          20

<210> SEQ ID NO 215
<211> LENGTH: 20
<212> TYPE: DNA
<213> ORGANISM: Homo sapiens

<400> SEQUENCE: 215
ttcaggttat gatgaggggt                                         20

<210> SEQ ID NO 216
<211> LENGTH: 20
<212> TYPE: DNA
<213> ORGANISM: Homo sapiens

<400> SEQUENCE: 216
gctccaggta atgccctctg                                         20

<210> SEQ ID NO 217
<211> LENGTH: 20
<212> TYPE: DNA
<213> ORGANISM: Homo sapiens

<400> SEQUENCE: 217
tgttcttcag gttatgatga                                         20

<210> SEQ ID NO 218
<211> LENGTH: 20
<212> TYPE: DNA
<213> ORGANISM: Homo sapiens

<400> SEQUENCE: 218
atgttcttca ggttatgatg                                         20

<210> SEQ ID NO 219
<211> LENGTH: 20
<212> TYPE: DNA
<213> ORGANISM: Homo sapiens

<400> SEQUENCE: 219
tcatcataac ctgaagaaca                                         20

<210> SEQ ID NO 220
<211> LENGTH: 20
<212> TYPE: DNA
<213> ORGANISM: Homo sapiens

<400> SEQUENCE: 220
tcataacctg aagaacatgg                                         20

<210> SEQ ID NO 221
<211> LENGTH: 20
<212> TYPE: DNA
<213> ORGANISM: Homo sapiens

<400> SEQUENCE: 221
acctgaagaa catggaggcc                                         20
```

<210> SEQ ID NO 222
<211> LENGTH: 20
<212> TYPE: DNA
<213> ORGANISM: Homo sapiens

<400> SEQUENCE: 222
cctgaagaac atggaggccc                                               20

<210> SEQ ID NO 223
<211> LENGTH: 20
<212> TYPE: DNA
<213> ORGANISM: Homo sapiens

<400> SEQUENCE: 223
gaagaacatg gaggcccggg                                               20

<210> SEQ ID NO 224
<211> LENGTH: 20
<212> TYPE: DNA
<213> ORGANISM: Homo sapiens

<400> SEQUENCE: 224
aagaacatgg aggcccggga                                               20

<210> SEQ ID NO 225
<211> LENGTH: 20
<212> TYPE: DNA
<213> ORGANISM: Homo sapiens

<400> SEQUENCE: 225
agaacatgga ggcccgggag                                               20

<210> SEQ ID NO 226
<211> LENGTH: 20
<212> TYPE: DNA
<213> ORGANISM: Homo sapiens

<400> SEQUENCE: 226
gggcaagtga caccccctccc                                              20

<210> SEQ ID NO 227
<211> LENGTH: 20
<212> TYPE: DNA
<213> ORGANISM: Homo sapiens

<400> SEQUENCE: 227
tgggcaagtg acaccccctcc                                              20

<210> SEQ ID NO 228
<211> LENGTH: 20
<212> TYPE: DNA
<213> ORGANISM: Homo sapiens

<400> SEQUENCE: 228 cccacccccct gtgtagcttt                                              20

<210> SEQ ID NO 229
<211> LENGTH: 20
<212> TYPE: DNA
<213> ORGANISM: Homo sapiens

<400> SEQUENCE: 229
ccccaccccc tgtgtagctt                                               20

<210> SEQ ID NO 230
<211> LENGTH: 20
<212> TYPE: DNA
<213> ORGANISM: Homo sapiens

<400> SEQUENCE: 230
tcacttgccc aaagctacac                                               20

<210> SEQ ID NO 231
<211> LENGTH: 20
<212> TYPE: DNA
<213> ORGANISM: Homo sapiens

<400> SEQUENCE: 231
cacttgccca aagctacaca                                               20

<210> SEQ ID NO 232
<211> LENGTH: 20
<212> TYPE: DNA
<213> ORGANISM: Homo sapiens

<400> SEQUENCE: 232
acttgcccaa agctacacag                                               20

<210> SEQ ID NO 233
<211> LENGTH: 20
<212> TYPE: DNA
<213> ORGANISM: Homo sapiens

<400> SEQUENCE: 233
cttgcccaaa gctacacagg                                               20

<210> SEQ ID NO 234
<211> LENGTH: 20
<212> TYPE: DNA
<213> ORGANISM: Homo sapiens

<400> SEQUENCE: 234
gcccaaagct acacaggggg                                               20

<210> SEQ ID NO 235
<211> LENGTH: 20
<212> TYPE: DNA
<213> ORGANISM: Homo sapiens

<400> SEQUENCE: 235
cccaaagcta cacaggtggt                                               20

<210> SEQ ID NO 236
<211> LENGTH: 20
<212> TYPE: DNA
<213> ORGANISM: Homo sapiens

<400> SEQUENCE: 236
ccaaagctac acagggggtg                                               20

<210> SEQ ID NO 237
<211> LENGTH: 20
<212> TYPE: DNA
<213> ORGANISM: Homo sapiens

<400> SEQUENCE: 237
agctacacag ggggtggggc          20

<210> SEQ ID NO 238
<211> LENGTH: 20
<212> TYPE: DNA
<213> ORGANISM: Homo sapiens

<400> SEQUENCE: 238 acaggggtg gggctggaag           20

<210> SEQ ID NO 239
<211> LENGTH: 20
<212> TYPE: DNA
<213> ORGANISM: Homo sapiens

<400> SEQUENCE: 239
ctggaagtgg ctccaagtgc          20

<210> SEQ ID NO 240
<211> LENGTH: 20
<212> TYPE: DNA
<213> ORGANISM: Homo sapiens

<400> SEQUENCE: 240 atgaggggg aacctgcact           20

<210> SEQ ID NO 241
<211> LENGTH: 20
<212> TYPE: DNA
<213> ORGANISM: Homo sapiens

<400> SEQUENCE: 241
ctaagcctga agaatgaggg          20

<210> SEQ ID NO 242
<211> LENGTH: 20
<212> TYPE: DNA
<213> ORGANISM: Homo sapiens

<400> SEQUENCE: 242
ccctaagcct gaagaatgag          20

<210> SEQ ID NO 243
<211> LENGTH: 20
<212> TYPE: DNA
<213> ORGANISM: Homo sapiens

<400> SEQUENCE: 243
gccctaagcc tgaagaatga          20

<210> SEQ ID NO 244
<211> LENGTH: 20
<212> TYPE: DNA
<213> ORGANISM: Homo sapiens

<400> SEQUENCE: 244 cccctcatt cttcaggctt           20

<210> SEQ ID NO 245
<211> LENGTH: 20
<212> TYPE: DNA
<213> ORGANISM: Homo sapiens

<400> SEQUENCE: 245 ccccctcattc ttcaggctta                                              20

<210> SEQ ID NO 246
<211> LENGTH: 20
<212> TYPE: DNA
<213> ORGANISM: Homo sapiens

<400> SEQUENCE: 246
tcattcttca ggcttagggc                                               20

<210> SEQ ID NO 247
<211> LENGTH: 20
<212> TYPE: DNA
<213> ORGANISM: Homo sapiens

<400> SEQUENCE: 247
ttcttcaggc ttagggctgg                                               20

<210> SEQ ID NO 248
<211> LENGTH: 20
<212> TYPE: DNA
<213> ORGANISM: Homo sapiens

<400> SEQUENCE: 248
tccctgtctg gggtaggact                                               20

<210> SEQ ID NO 249
<211> LENGTH: 20
<212> TYPE: DNA
<213> ORGANISM: Homo sapiens

<400> SEQUENCE: 249
ttccctgtct ggggtaggac                                               20

<210> SEQ ID NO 250
<211> LENGTH: 20
<212> TYPE: DNA
<213> ORGANISM: Homo sapiens

<400> SEQUENCE: 250
tcagtttccc tgtctggggt                                               20

<210> SEQ ID NO 251
<211> LENGTH: 20
<212> TYPE: DNA
<213> ORGANISM: Homo sapiens

<400> SEQUENCE: 251
gcccagtcct accccagaca                                               20

<210> SEQ ID NO 252
<211> LENGTH: 20
<212> TYPE: DNA
<213> ORGANISM: Homo sapiens

<400> SEQUENCE: 252
aggcctcagt ttccctgtct                                               20

<210> SEQ ID NO 253
<211> LENGTH: 20
<212> TYPE: DNA
<213> ORGANISM: Homo sapiens

```
<400> SEQUENCE: 253
caggcctcag tttccctgtc                                               20

<210> SEQ ID NO 254
<211> LENGTH: 20
<212> TYPE: DNA
<213> ORGANISM: Homo sapiens

<400> SEQUENCE: 254
taccccagac agggaaactg                                               20

<210> SEQ ID NO 255
<211> LENGTH: 20
<212> TYPE: DNA
<213> ORGANISM: Homo sapiens

<400> SEQUENCE: 255
gtgtgtcttt gggtgatttc                                               20

<210> SEQ ID NO 256
<211> LENGTH: 20
<212> TYPE: DNA
<213> ORGANISM: Homo sapiens

<400> SEQUENCE: 256
ccaacatgct gtgtgtcttt                                               20

<210> SEQ ID NO 257
<211> LENGTH: 20
<212> TYPE: DNA
<213> ORGANISM: Homo sapiens

<400> SEQUENCE: 257
gccaacatgc tgtgtgtctt                                               20

<210> SEQ ID NO 258
<211> LENGTH: 20
<212> TYPE: DNA
<213> ORGANISM: Homo sapiens

<400> SEQUENCE: 258
cccaaagaca cacagcatgt                                               20

<210> SEQ ID NO 259
<211> LENGTH: 20
<212> TYPE: DNA
<213> ORGANISM: Homo sapiens

<400> SEQUENCE: 259
aagacacaca gcatgttggc                                               20

<210> SEQ ID NO 260
<211> LENGTH: 20
<212> TYPE: DNA
<213> ORGANISM: Homo sapiens

<400> SEQUENCE: 260
acacagcatg ttggctggac                                               20

<210> SEQ ID NO 261
<211> LENGTH: 20
<212> TYPE: DNA
```

<213> ORGANISM: Homo sapiens

<400> SEQUENCE: 261
agcatgttgg ctggactgga                                           20

<210> SEQ ID NO 262
<211> LENGTH: 20
<212> TYPE: DNA
<213> ORGANISM: Homo sapiens

<400> SEQUENCE: 262
acatcaaggc acctgcggtc                                           20

<210> SEQ ID NO 263
<211> LENGTH: 20
<212> TYPE: DNA
<213> ORGANISM: Homo sapiens

<400> SEQUENCE: 263
actgaacatc aaggcacctg                                           20

<210> SEQ ID NO 264
<211> LENGTH: 20
<212> TYPE: DNA
<213> ORGANISM: Homo sapiens

<400> SEQUENCE: 264
acccaccaga ctgaacatca                                           20

<210> SEQ ID NO 265
<211> LENGTH: 20
<212> TYPE: DNA
<213> ORGANISM: Homo sapiens

<400> SEQUENCE: 265
aggtgccttg atgttcagtc                                           20

<210> SEQ ID NO 266
<211> LENGTH: 20
<212> TYPE: DNA
<213> ORGANISM: Homo sapiens

<400> SEQUENCE: 266
tgccttgatg ttcagtctgg                                           20

<210> SEQ ID NO 267
<211> LENGTH: 20
<212> TYPE: DNA
<213> ORGANISM: Homo sapiens

<400> SEQUENCE: 267
gccttgatgt tcagtctggt                                           20

<210> SEQ ID NO 268
<211> LENGTH: 20
<212> TYPE: DNA
<213> ORGANISM: Homo sapiens

<400> SEQUENCE: 268
ccaaagggag gtgggtggga                                           20

<210> SEQ ID NO 269
<211> LENGTH: 20

```
<212> TYPE: DNA
<213> ORGANISM: Homo sapiens

<400> SEQUENCE: 269
aggcccaaag ggaggtgggt                                            20

<210> SEQ ID NO 270
<211> LENGTH: 20
<212> TYPE: DNA
<213> ORGANISM: Homo sapiens

<400> SEQUENCE: 270
gaggcccaaa gggaggtggg                                            20

<210> SEQ ID NO 271
<211> LENGTH: 20
<212> TYPE: DNA
<213> ORGANISM: Homo sapiens

<400> SEQUENCE: 271
atcgaggccc aaagggaggt                                            20

<210> SEQ ID NO 272
<211> LENGTH: 20
<212> TYPE: DNA
<213> ORGANISM: Homo sapiens

<400> SEQUENCE: 272
gatcgaggcc caaagggagg                                            20

<210> SEQ ID NO 273
<211> LENGTH: 20
<212> TYPE: DNA
<213> ORGANISM: Homo sapiens

<400> SEQUENCE: 273
ccatcccacc cacctccctt                                            20

<210> SEQ ID NO 274
<211> LENGTH: 20
<212> TYPE: DNA
<213> ORGANISM: Homo sapiens

<400> SEQUENCE: 274
catcccaccc acctcccttt                                            20

<210> SEQ ID NO 275
<211> LENGTH: 20
<212> TYPE: DNA
<213> ORGANISM: Homo sapiens

<400> SEQUENCE: 275
agggatcgag gcccaaaggg                                            20

<210> SEQ ID NO 276
<211> LENGTH: 20
<212> TYPE: DNA
<213> ORGANISM: Homo sapiens

<400> SEQUENCE: 276
ggcgagggat cgaggcccaa                                            20

<210> SEQ ID NO 277
```

```
<211> LENGTH: 20
<212> TYPE: DNA
<213> ORGANISM: Homo sapiens

<400> SEQUENCE: 277
tggtgagggg cgagggatcg                                                 20

<210> SEQ ID NO 278
<211> LENGTH: 20
<212> TYPE: DNA
<213> ORGANISM: Homo sapiens

<400> SEQUENCE: 278
gggggactgg tgagggcga                                                  20

<210> SEQ ID NO 279
<211> LENGTH: 20
<212> TYPE: DNA
<213> ORGANISM: Homo sapiens

<400> SEQUENCE: 279 aggggactg gtgagggcg                                                   20

<210> SEQ ID NO 280
<211> LENGTH: 20
<212> TYPE: DNA
<213> ORGANISM: Homo sapiens

<400> SEQUENCE: 280
tcagaagggg gactggtgag                                                 20

<210> SEQ ID NO 281
<211> LENGTH: 20
<212> TYPE: DNA
<213> ORGANISM: Homo sapiens

<400> SEQUENCE: 281
ctcagaaggg ggactggtga                                                 20

<210> SEQ ID NO 282
<211> LENGTH: 20
<212> TYPE: DNA
<213> ORGANISM: Homo sapiens

<400> SEQUENCE: 282
tctcagaagg gggactggtg                                                 20

<210> SEQ ID NO 283
<211> LENGTH: 20
<212> TYPE: DNA
<213> ORGANISM: Homo sapiens

<400> SEQUENCE: 283
cgggctctca gaagggggac                                                 20

<210> SEQ ID NO 284
<211> LENGTH: 20
<212> TYPE: DNA
<213> ORGANISM: Homo sapiens

<400> SEQUENCE: 284
taatacgggc tctcagaagg                                                 20
```

```
<210> SEQ ID NO 285
<211> LENGTH: 20
<212> TYPE: DNA
<213> ORGANISM: Homo sapiens

<400> SEQUENCE: 285
ctaatacggg ctctcagaag                                              20

<210> SEQ ID NO 286
<211> LENGTH: 20
<212> TYPE: DNA
<213> ORGANISM: Homo sapiens

<400> SEQUENCE: 286
gctaatacgg gctctcagaa                                              20

<210> SEQ ID NO 287
<211> LENGTH: 20
<212> TYPE: DNA
<213> ORGANISM: Homo sapiens

<400> SEQUENCE: 287
tgctaatacg ggctctcaga                                              20

<210> SEQ ID NO 288
<211> LENGTH: 20
<212> TYPE: DNA
<213> ORGANISM: Homo sapiens

<400> SEQUENCE: 288
ggccggctcc ctgctaatac                                              20

<210> SEQ ID NO 289
<211> LENGTH: 20
<212> TYPE: DNA
<213> ORGANISM: Homo sapiens

<400> SEQUENCE: 289
gggccggctc cctgctaata                                              20

<210> SEQ ID NO 290
<211> LENGTH: 20
<212> TYPE: DNA
<213> ORGANISM: Homo sapiens

<400> SEQUENCE: 290
ttctgagagc ccgtattagc                                              20

<210> SEQ ID NO 291
<211> LENGTH: 20
<212> TYPE: DNA
<213> ORGANISM: Homo sapiens

<400> SEQUENCE: 291
tctgagagcc cgtattagca                                              20

<210> SEQ ID NO 292
<211> LENGTH: 20
<212> TYPE: DNA
<213> ORGANISM: Homo sapiens

<400> SEQUENCE: 292
agcccgtatt agcagggagc                                              20
```

```
<210> SEQ ID NO 293
<211> LENGTH: 20
<212> TYPE: DNA
<213> ORGANISM: Homo sapiens

<400> SEQUENCE: 293
ctgccagaag gagtaggggc                                               20

<210> SEQ ID NO 294
<211> LENGTH: 20
<212> TYPE: DNA
<213> ORGANISM: Homo sapiens

<400> SEQUENCE: 294
gggtctgcca gaaggagtag                                               20

<210> SEQ ID NO 295
<211> LENGTH: 20
<212> TYPE: DNA
<213> ORGANISM: Homo sapiens

<400> SEQUENCE: 295
tgggtctgcc agaaggagta                                               20

<210> SEQ ID NO 296
<211> LENGTH: 20
<212> TYPE: DNA
<213> ORGANISM: Homo sapiens

<400> SEQUENCE: 296
ctgggtctgc cagaaggagt                                               20

<210> SEQ ID NO 297
<211> LENGTH: 20
<212> TYPE: DNA
<213> ORGANISM: Homo sapiens

<400> SEQUENCE: 297
gagccggccc ctactccttc                                               20

<210> SEQ ID NO 298
<211> LENGTH: 20
<212> TYPE: DNA
<213> ORGANISM: Homo sapiens

<400> SEQUENCE: 298
ccttagctgg gtctgccaga                                               20

<210> SEQ ID NO 299
<211> LENGTH: 20
<212> TYPE: DNA
<213> ORGANISM: Homo sapiens

<400> SEQUENCE: 299
ccttctggca gacccagcta                                               20

<210> SEQ ID NO 300
<211> LENGTH: 20
<212> TYPE: DNA
<213> ORGANISM: Homo sapiens

<400> SEQUENCE: 300
cctaaggtag aaccttagct                                               20
```

```
<210> SEQ ID NO 301
<211> LENGTH: 20
<212> TYPE: DNA
<213> ORGANISM: Homo sapiens

<400> SEQUENCE: 301
ccctaaggta gaaccttagc                                               20

<210> SEQ ID NO 302
<211> LENGTH: 20
<212> TYPE: DNA
<213> ORGANISM: Homo sapiens

<400> SEQUENCE: 302
cccagctaag gttctacctt                                               20

<210> SEQ ID NO 303
<211> LENGTH: 20
<212> TYPE: DNA
<213> ORGANISM: Homo sapiens

<400> SEQUENCE: 303
ccagctaagg ttctacctta                                               20

<210> SEQ ID NO 304
<211> LENGTH: 20
<212> TYPE: DNA
<213> ORGANISM: Homo sapiens

<400> SEQUENCE: 304
cagctaaggt tctaccttag                                               20

<210> SEQ ID NO 305
<211> LENGTH: 20
<212> TYPE: DNA
<213> ORGANISM: Homo sapiens

<400> SEQUENCE: 305
gggaggtggc gtggcccta                                                20

<210> SEQ ID NO 306
<211> LENGTH: 20
<212> TYPE: DNA
<213> ORGANISM: Homo sapiens

<400> SEQUENCE: 306
ccctccctgg ggaggtggcg                                               20

<210> SEQ ID NO 307
<211> LENGTH: 20
<212> TYPE: DNA
<213> ORGANISM: Homo sapiens

<400> SEQUENCE: 307
tggacccctc cctggggagg                                               20

<210> SEQ ID NO 308
<211> LENGTH: 20
<212> TYPE: DNA
<213> ORGANISM: Homo sapiens

<400> SEQUENCE: 308
``` agggggccacg ccacctcccc                                              20

<210> SEQ ID NO 309
<211> LENGTH: 20
<212> TYPE: DNA
<213> ORGANISM: Homo sapiens

<400> SEQUENCE: 309
ggggccacgc cacctcccca                                               20

<210> SEQ ID NO 310
<211> LENGTH: 20
<212> TYPE: DNA
<213> ORGANISM: Homo sapiens

<400> SEQUENCE: 310
ctctggaccc ctccctgggg                                               20

<210> SEQ ID NO 311
<211> LENGTH: 20
<212> TYPE: DNA
<213> ORGANISM: Homo sapiens

<400> SEQUENCE: 311
gccacgccac ctccccaggg                                               20

<210> SEQ ID NO 312
<211> LENGTH: 20
<212> TYPE: DNA
<213> ORGANISM: Homo sapiens

<400> SEQUENCE: 312
ccacgccacc tccccaggga                                               20

<210> SEQ ID NO 313
<211> LENGTH: 20
<212> TYPE: DNA
<213> ORGANISM: Homo sapiens

<400> SEQUENCE: 313
tgcctctgga ccccctccctg                                              20

<210> SEQ ID NO 314
<211> LENGTH: 20
<212> TYPE: DNA
<213> ORGANISM: Homo sapiens

<400> SEQUENCE: 314
cacgccacct ccccagggag                                               20

<210> SEQ ID NO 315
<211> LENGTH: 20
<212> TYPE: DNA
<213> ORGANISM: Homo sapiens

<400> SEQUENCE: 315
atgcctctgg accctccct                                                20

<210> SEQ ID NO 316
<211> LENGTH: 20
<212> TYPE: DNA
<213> ORGANISM: Homo sapiens

<400> SEQUENCE: 316

```
catgcctctg gacccctccc                                              20

<210> SEQ ID NO 317
<211> LENGTH: 20
<212> TYPE: DNA
<213> ORGANISM: Homo sapiens

<400> SEQUENCE: 317
ctccccaggg aggggtccag                                              20

<210> SEQ ID NO 318
<211> LENGTH: 20
<212> TYPE: DNA
<213> ORGANISM: Homo sapiens

<400> SEQUENCE: 318
cagggagggg tccagaggca                                              20

<210> SEQ ID NO 319
<211> LENGTH: 20
<212> TYPE: DNA
<213> ORGANISM: Homo sapiens

<400> SEQUENCE: 319
accccaggtc cccatgcctc                                              20

<210> SEQ ID NO 320
<211> LENGTH: 20
<212> TYPE: DNA
<213> ORGANISM: Homo sapiens

<400> SEQUENCE: 320
agggaggggt ccagaggcat                                              20

<210> SEQ ID NO 321
<211> LENGTH: 20
<212> TYPE: DNA
<213> ORGANISM: Homo sapiens

<400> SEQUENCE: 321
gggaggggtc cagaggcatg                                              20

<210> SEQ ID NO 322
<211> LENGTH: 20
<212> TYPE: DNA
<213> ORGANISM: Homo sapiens

<400> SEQUENCE: 322
ggtccagagg catggggacc                                              20

<210> SEQ ID NO 323
<211> LENGTH: 20
<212> TYPE: DNA
<213> ORGANISM: Homo sapiens

<400> SEQUENCE: 323
gtccagaggc atggggacct                                              20

<210> SEQ ID NO 324
<211> LENGTH: 20
<212> TYPE: DNA
<213> ORGANISM: Homo sapiens
```

```
<400> SEQUENCE: 324
tccagaggca tggggacctg                                              20

<210> SEQ ID NO 325
<211> LENGTH: 20
<212> TYPE: DNA
<213> ORGANISM: Homo sapiens

<400> SEQUENCE: 325
tgtcctgtga ggggcacccc                                              20

<210> SEQ ID NO 326
<211> LENGTH: 20
<212> TYPE: DNA
<213> ORGANISM: Homo sapiens

<400> SEQUENCE: 326
ggacctgggg tgcccctcac                                              20

<210> SEQ ID NO 327
<211> LENGTH: 20
<212> TYPE: DNA
<213> ORGANISM: Homo sapiens

<400> SEQUENCE: 327
gcaaggaagt gtcctgtgag                                              20

<210> SEQ ID NO 328
<211> LENGTH: 20
<212> TYPE: DNA
<213> ORGANISM: Homo sapiens

<400> SEQUENCE: 328
tgcaaggaag tgtcctgtga                                              20

<210> SEQ ID NO 329
<211> LENGTH: 20
<212> TYPE: DNA
<213> ORGANISM: Homo sapiens

<400> SEQUENCE: 329
ctgcaaggaa gtgtcctgtg                                              20

<210> SEQ ID NO 330
<211> LENGTH: 20
<212> TYPE: DNA
<213> ORGANISM: Homo sapiens

<400> SEQUENCE: 330
ctcacaggac acttccttgc                                              20

<210> SEQ ID NO 331
<211> LENGTH: 20
<212> TYPE: DNA
<213> ORGANISM: Homo sapiens

<400> SEQUENCE: 331
atggcacctc tgttcctgca                                              20

<210> SEQ ID NO 332
<211> LENGTH: 20
<212> TYPE: DNA
<213> ORGANISM: Homo sapiens
```

```
<400> SEQUENCE: 332
acacttcctt gcaggaacag                                               20

<210> SEQ ID NO 333
<211> LENGTH: 20
<212> TYPE: DNA
<213> ORGANISM: Homo sapiens

<400> SEQUENCE: 333
gaggggaaag aggaggggag                                               20

<210> SEQ ID NO 334
<211> LENGTH: 20
<212> TYPE: DNA
<213> ORGANISM: Homo sapiens

<400> SEQUENCE: 334
taaggaagcc tcggagctgg                                               20

<210> SEQ ID NO 335
<211> LENGTH: 20
<212> TYPE: DNA
<213> ORGANISM: Homo sapiens

<400> SEQUENCE: 335
atgttcttca ggttatgatg                                               20

<210> SEQ ID NO 336
<211> LENGTH: 20
<212> TYPE: DNA
<213> ORGANISM: Homo sapiens

<400> SEQUENCE: 336
gaagaacatg gaggcccggg                                               20

<210> SEQ ID NO 337
<211> LENGTH: 20
<212> TYPE: DNA
<213> ORGANISM: Homo sapiens

<400> SEQUENCE: 337
cacttgccca aagctacaca                                               20

<210> SEQ ID NO 338
<211> LENGTH: 20
<212> TYPE: DNA
<213> ORGANISM: Homo sapiens

<400> SEQUENCE: 338
ttcctccagc cctaagcctg                                               20

<210> SEQ ID NO 339
<211> LENGTH: 20
<212> TYPE: DNA
<213> ORGANISM: Homo sapiens

<400> SEQUENCE: 339
caggcctcag tttccctgtc                                               20

<210> SEQ ID NO 340
<211> LENGTH: 20
<212> TYPE: DNA
```

```
<213> ORGANISM: Homo sapiens

<400> SEQUENCE: 340
agccaacatg ctgtgtgtct                                               20

<210> SEQ ID NO 341
<211> LENGTH: 20
<212> TYPE: DNA
<213> ORGANISM: Homo sapiens

<400> SEQUENCE: 341
gtgccttgat gttcagtctg                                               20

<210> SEQ ID NO 342
<211> LENGTH: 20
<212> TYPE: DNA
<213> ORGANISM: Homo sapiens

<400> SEQUENCE: 342
gaggcccaaa gggaggtggg                                               20

<210> SEQ ID NO 343
<211> LENGTH: 20
<212> TYPE: DNA
<213> ORGANISM: Homo sapiens

<400> SEQUENCE: 343
ggatcgaggc ccaaagggag                                               20

<210> SEQ ID NO 344
<211> LENGTH: 20
<212> TYPE: DNA
<213> ORGANISM: Homo sapiens

<400> SEQUENCE: 344 aggggggactg gtgaggggcg                                              20

<210> SEQ ID NO 345
<211> LENGTH: 20
<212> TYPE: DNA
<213> ORGANISM: Homo sapiens

<400> SEQUENCE: 345
ccttagctgg gtctgccaga                                               20

<210> SEQ ID NO 346
<211> LENGTH: 20
<212> TYPE: DNA
<213> ORGANISM: Homo sapiens

<400> SEQUENCE: 346
cccctaaggt agaaccttag                                               20

<210> SEQ ID NO 347
<211> LENGTH: 20
<212> TYPE: DNA
<213> ORGANISM: Homo sapiens

<400> SEQUENCE: 347
gccacgccac ctccccaggg                                               20

<210> SEQ ID NO 348
<211> LENGTH: 20
```

```
<212> TYPE: DNA
<213> ORGANISM: Homo sapiens

<400> SEQUENCE: 348
ggtccagagg catggggacc                                                  20

<210> SEQ ID NO 349
<211> LENGTH: 28
<212> TYPE: DNA
<213> ORGANISM: Homo sapiens

<400> SEQUENCE: 349
gagggccaga aatcacccaa agacacac                                         28

<210> SEQ ID NO 350
<211> LENGTH: 28
<212> TYPE: DNA
<213> ORGANISM: Homo sapiens

<400> SEQUENCE: 350
gagggcagga aatcacccaa ggtcacac                                         28

<210> SEQ ID NO 351
<211> LENGTH: 28
<212> TYPE: DNA
<213> ORGANISM: Homo sapiens

<400> SEQUENCE: 351
gcctaataga aatcacccaa attgacac                                         28

<210> SEQ ID NO 352
<211> LENGTH: 28
<212> TYPE: DNA
<213> ORGANISM: Homo sapiens

<400> SEQUENCE: 352
aatttaaaga aatcacccaa gagcacac                                         28

<210> SEQ ID NO 353
<211> LENGTH: 28
<212> TYPE: DNA
<213> ORGANISM: Homo sapiens

<400> SEQUENCE: 353
gatcagcaga aatcacccaa cctagtac                                         28

<210> SEQ ID NO 354
<211> LENGTH: 28
<212> TYPE: DNA
<213> ORGANISM: Homo sapiens

<400> SEQUENCE: 354
aagaaagaga aatcacccaa tttcacat                                         28

<210> SEQ ID NO 355
<211> LENGTH: 28
<212> TYPE: DNA
<213> ORGANISM: Homo sapiens

<400> SEQUENCE: 355
agggtttaga aatcacccaa atccacat                                         28

<210> SEQ ID NO 356
```

```
<211> LENGTH: 29
<212> TYPE: DNA
<213> ORGANISM: Homo sapiens

<400> SEQUENCE: 356
cattcaggaa agtacattgg caataatac                              29

<210> SEQ ID NO 357
<211> LENGTH: 28
<212> TYPE: DNA
<213> ORGANISM: Homo sapiens

<400> SEQUENCE: 357
atttgcggaa agacattggc tttagtac                               28

<210> SEQ ID NO 358
<211> LENGTH: 28
<212> TYPE: DNA
<213> ORGANISM: Homo sapiens

<400> SEQUENCE: 358
ttggggagaa agacattggc attcacac                               28

<210> SEQ ID NO 359
<211> LENGTH: 28
<212> TYPE: DNA
<213> ORGANISM: Homo sapiens

<400> SEQUENCE: 359
tttgggggaa agtacatggc ataaacac                               28

<210> SEQ ID NO 360
<211> LENGTH: 29
<212> TYPE: DNA
<213> ORGANISM: Homo sapiens

<400> SEQUENCE: 360
aggcaggaaa aatacattgg caaaaacat                              29

<210> SEQ ID NO 361
<211> LENGTH: 28
<212> TYPE: DNA
<213> ORGANISM: Homo sapiens

<400> SEQUENCE: 361
cactccagaa agtacttggc tgccacac                               28

<210> SEQ ID NO 362
<211> LENGTH: 29
<212> TYPE: DNA
<213> ORGANISM: Homo sapiens

<400> SEQUENCE: 362
tgctattgta aatacattgg cctgtacac                              29

<210> SEQ ID NO 363
<211> LENGTH: 29
<212> TYPE: DNA
<213> ORGANISM: Homo sapiens

<400> SEQUENCE: 363
tgttgaagaa tgtacattgt ctcacacac                              29
```

-continued

```
<210> SEQ ID NO 364
<211> LENGTH: 29
<212> TYPE: DNA
<213> ORGANISM: Homo sapiens

<400> SEQUENCE: 364
tgttgaagaa tgtacattgt cgcacacac                                    29

<210> SEQ ID NO 365
<211> LENGTH: 29
<212> TYPE: DNA
<213> ORGANISM: Homo sapiens

<400> SEQUENCE: 365
ctagattaaa tgtacattgg ccaaaacat                                    29

<210> SEQ ID NO 366
<211> LENGTH: 29
<212> TYPE: DNA
<213> ORGANISM: Homo sapiens

<400> SEQUENCE: 366
agagaaagag agtacattgg cgaagatac                                    29

<210> SEQ ID NO 367
<211> LENGTH: 12
<212> TYPE: RNA
<213> ORGANISM: Streptococcus pyogenes

<400> SEQUENCE: 367
guuuuagagc ua                                                      12

<210> SEQ ID NO 368
<211> LENGTH: 13
<212> TYPE: RNA
<213> ORGANISM: Artificial Sequence
<220> FEATURE:
<223> OTHER INFORMATION: First complementary domain
<220> FEATURE:
<221> NAME/KEY: misc_feature
<222> LOCATION: (13)..(13)
<223> OTHER INFORMATION: n may be 5 to 15 bases selected from a, t, u,
      and g.

<400> SEQUENCE: 368
guuuuagagc uan                                                     13

<210> SEQ ID NO 369
<211> LENGTH: 25
<212> TYPE: RNA
<213> ORGANISM: Campylobacter jejuni

<400> SEQUENCE: 369
guuuuagucc cuuuuuaaau uucuu                                        25

<210> SEQ ID NO 370
<211> LENGTH: 25
<212> TYPE: RNA
<213> ORGANISM: Artificial sequence
<220> FEATURE:
<223> OTHER INFORMATION: first complementary domain
<220> FEATURE:
<221> NAME/KEY: misc_feature
<222> LOCATION: (25)..(25)
<223> OTHER INFORMATION: n may be 5 to 15 bases selected from a, t, u,
      and g
```

```
<400> SEQUENCE: 370
guuuuagucc cuuuuuaaau uucuu                                              25

<210> SEQ ID NO 371
<211> LENGTH: 9
<212> TYPE: RNA
<213> ORGANISM: Parcubacteria bacterium

<400> SEQUENCE: 371 uuuguagau                                                                 9

<210> SEQ ID NO 372
<211> LENGTH: 10
<212> TYPE: RNA
<213> ORGANISM: Artificial sequence
<220> FEATURE:
<223> OTHER INFORMATION: First complementary domain
<220> FEATURE:
<221> NAME/KEY: misc_feature
<222> LOCATION: (1)..(1)
<223> OTHER INFORMATION: n may be 1 to 5 bases selected from a, t, u,
      and g

<400> SEQUENCE: 372 nuuuguagau                                                               10

<210> SEQ ID NO 373
<211> LENGTH: 14
<212> TYPE: RNA
<213> ORGANISM: Streptococcus pyogenes

<400> SEQUENCE: 373
uagcaaguua aaau                                                          14

<210> SEQ ID NO 374
<211> LENGTH: 16
<212> TYPE: RNA
<213> ORGANISM: Artificial sequence
<220> FEATURE:
<223> OTHER INFORMATION: Second complementary domain
<220> FEATURE:
<221> NAME/KEY: misc_feature
<222> LOCATION: (1)..(1)
<223> OTHER INFORMATION: n may be 1 to 15 bases selected from a, t, u,
      and g
<220> FEATURE:
<221> NAME/KEY: misc_feature
<222> LOCATION: (16)..(16)
<223> OTHER INFORMATION: n may be 1 to 6 bases selected from a, t, u,
      and g

<400> SEQUENCE: 374
nuagcaaguu aaaaun                                                        16

<210> SEQ ID NO 375
<211> LENGTH: 25
<212> TYPE: RNA
<213> ORGANISM: Campylobacter jejuni

<400> SEQUENCE: 375
aagaaauuua aaagggacu aaaau                                               25

<210> SEQ ID NO 376
<211> LENGTH: 27
<212> TYPE: RNA
<213> ORGANISM: Artificial sequence
<220> FEATURE:
```

<223> OTHER INFORMATION: Second complementary domain
<220> FEATURE:
<221> NAME/KEY: misc_feature
<222> LOCATION: (1)..(1)
<223> OTHER INFORMATION: n is 1 to 15 bases selected from a, t, u, and g
<220> FEATURE:
<221> NAME/KEY: misc_feature
<222> LOCATION: (27)..(27)
<223> OTHER INFORMATION: n is 1 to 6 bases selected from a, t, u, and g

<400> SEQUENCE: 376
naagaaauuu aaaagggac uaaaaun       27

<210> SEQ ID NO 377
<211> LENGTH: 11
<212> TYPE: RNA
<213> ORGANISM: Parcubacteria bacterium

<400> SEQUENCE: 377
aaauuucuac u       11

<210> SEQ ID NO 378
<211> LENGTH: 13
<212> TYPE: RNA
<213> ORGANISM: Artificial sequence
<220> FEATURE:
<223> OTHER INFORMATION: Second complementary domain
<220> FEATURE:
<221> NAME/KEY: misc_feature
<222> LOCATION: (1)..(1)
<223> OTHER INFORMATION: n is 1 to 10 nucleotides selected from a, t, u,
      and g.
<220> FEATURE:
<221> NAME/KEY: misc_feature
<222> LOCATION: (13)..(13)
<223> OTHER INFORMATION: n is 1 to 6nucleotides selected from a, t, u,
      and g.

<400> SEQUENCE: 378
naaauuucua cun       13

<210> SEQ ID NO 379
<211> LENGTH: 12
<212> TYPE: RNA
<213> ORGANISM: Streptococcus pyogenes

<400> SEQUENCE: 379
aaggcuaguc cg       12

<210> SEQ ID NO 380
<211> LENGTH: 13
<212> TYPE: RNA
<213> ORGANISM: Artificial sequence
<220> FEATURE:
<223> OTHER INFORMATION: Proximal domain
<220> FEATURE:
<221> NAME/KEY: misc_feature
<222> LOCATION: (13)..(13)
<223> OTHER INFORMATION: n is 1 to 15 nucleotides selected from a, t, u,
      and g

<400> SEQUENCE: 380
aaggcuaguc cgn       13

<210> SEQ ID NO 381
<211> LENGTH: 11
<212> TYPE: RNA
<213> ORGANISM: Campylobacter jejuni

```
<400> SEQUENCE: 381
aaagaguuug c                                                          11

<210> SEQ ID NO 382
<211> LENGTH: 12
<212> TYPE: RNA
<213> ORGANISM: Artificial sequence
<220> FEATURE:
<223> OTHER INFORMATION: Proximal domain
<220> FEATURE:
<221> NAME/KEY: misc_feature
<222> LOCATION: (12)..(12)
<223> OTHER INFORMATION: n is one ot 40 nucleotides, selected from a, t,
      u, and g

<400> SEQUENCE: 382
aaagaguuug cn                                                         12

<210> SEQ ID NO 383
<211> LENGTH: 34
<212> TYPE: RNA
<213> ORGANISM: Streptococcus pyogenes

<400> SEQUENCE: 383
uuaucaacuu gaaaaagugg caccgagucg gugc                                 34

<210> SEQ ID NO 384
<211> LENGTH: 35
<212> TYPE: RNA
<213> ORGANISM: Artificial sequence
<220> FEATURE:
<223> OTHER INFORMATION: Tail domain
<220> FEATURE:
<221> NAME/KEY: misc_feature
<222> LOCATION: (35)..(35)
<223> OTHER INFORMATION: n is 1 to 15 nucleotides selected from a, t, u,
      and g

<400> SEQUENCE: 384
uuaucaacuu gaaaaagugg caccgagucg gugcn                                35

<210> SEQ ID NO 385
<211> LENGTH: 38
<212> TYPE: RNA
<213> ORGANISM: Campylobacter jejuni

<400> SEQUENCE: 385
gggacucugc gggguuacaa uccccuaaaa ccgcuuuu                             38

<210> SEQ ID NO 386
<211> LENGTH: 39
<212> TYPE: RNA
<213> ORGANISM: Artificial sequence
<220> FEATURE:
<223> OTHER INFORMATION: Tail domain
<220> FEATURE:
<221> NAME/KEY: misc_feature
<222> LOCATION: (39)..(39)
<223> OTHER INFORMATION: n is 1 to 15 nucleotides selected from a, t, u,
      and g

<400> SEQUENCE: 386
gggacucugc gggguuacaa uccccuaaaa ccgcuuuun                            39

<210> SEQ ID NO 387
<211> LENGTH: 22
<212> TYPE: RNA
```

```
<213> ORGANISM: Streptococcus thermophilus

<400> SEQUENCE: 387
guuuuagagc uguguuguuu cg                                          22

<210> SEQ ID NO 388
<211> LENGTH: 24
<212> TYPE: RNA
<213> ORGANISM: Streptococcus thermophilus

<400> SEQUENCE: 388
cgaaacaaca cagcgaguua aaau                                        24

<210> SEQ ID NO 389
<211> LENGTH: 13
<212> TYPE: RNA
<213> ORGANISM: Streptococcus thermophilus

<400> SEQUENCE: 389
aaggcuuagu ccg                                                    13

<210> SEQ ID NO 390
<211> LENGTH: 38
<212> TYPE: RNA
<213> ORGANISM: Streptococcus thermophiles

<400> SEQUENCE: 390
uacucaacuu gaaaaggugg caccgauucg uguuuuu                          38

<210> SEQ ID NO 391
<211> LENGTH: 20
<212> TYPE: DNA
<213> ORGANISM: Artificial sequence
<220> FEATURE:
<223> OTHER INFORMATION: Target sequence

<400> SEQUENCE: 391
atcattggca gactagttcg                                             20

<210> SEQ ID NO 392
<211> LENGTH: 20
<212> TYPE: DNA
<213> ORGANISM: Artificial sequence
<220> FEATURE:
<223> OTHER INFORMATION: Target sequence

<400> SEQUENCE: 392
cgaactagtc tgccaatgat                                             20

<210> SEQ ID NO 393
<211> LENGTH: 7
<212> TYPE: PRT
<213> ORGANISM: Artificial sequence
<220> FEATURE:
<223> OTHER INFORMATION: NLS of SV40 virus large T antigen

<400> SEQUENCE: 393

Pro Lys Lys Lys Arg Lys Val
1               5

<210> SEQ ID NO 394
<211> LENGTH: 16
<212> TYPE: PRT
<213> ORGANISM: Artificial sequence
<220> FEATURE:
```

<223> OTHER INFORMATION: NLS from nucleoplasmin

<400> SEQUENCE: 394

Lys Arg Pro Ala Ala Thr Lys Lys Ala Gly Gln Ala Lys Lys Lys Lys
1               5                   10                  15

<210> SEQ ID NO 395
<211> LENGTH: 9
<212> TYPE: PRT
<213> ORGANISM: Artificial sequence
<220> FEATURE:
<223> OTHER INFORMATION: c-myc NLS

<400> SEQUENCE: 395

Pro Ala Ala Lys Arg Val Lys Leu Asp
1               5

<210> SEQ ID NO 396
<211> LENGTH: 11
<212> TYPE: PRT
<213> ORGANISM: Artificial sequence
<220> FEATURE:
<223> OTHER INFORMATION: c-myc NLS

<400> SEQUENCE: 396

Arg Gln Arg Arg Asn Glu Leu Lys Arg Ser Pro
1               5                   10

<210> SEQ ID NO 397
<211> LENGTH: 38
<212> TYPE: PRT
<213> ORGANISM: Artificial sequence
<220> FEATURE:
<223> OTHER INFORMATION: hRNPA1 M9 NLS

<400> SEQUENCE: 397

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
            35

<210> SEQ ID NO 398
<211> LENGTH: 42
<212> TYPE: PRT
<213> ORGANISM: Artificial sequence
<220> FEATURE:
<223> OTHER INFORMATION: importin-alpha-derived IBB domain

<400> SEQUENCE: 398

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40

<210> SEQ ID NO 399
<211> LENGTH: 8
<212> TYPE: PRT
<213> ORGANISM: Artificial sequence
<220> FEATURE:
<223> OTHER INFORMATION: myoma T protein

```
<400> SEQUENCE: 399

Val Ser Arg Lys Arg Pro Arg Pro
1               5

<210> SEQ ID NO 400
<211> LENGTH: 8
<212> TYPE: PRT
<213> ORGANISM: Artificial sequence
<220> FEATURE:
<223> OTHER INFORMATION: myoma T protein

<400> SEQUENCE: 400

Pro Pro Lys Lys Ala Arg Glu Asp
1               5

<210> SEQ ID NO 401
<211> LENGTH: 8
<212> TYPE: PRT
<213> ORGANISM: Homo sapiens

<400> SEQUENCE: 401

Pro Gln Pro Lys Lys Lys Pro Leu
1               5

<210> SEQ ID NO 402
<211> LENGTH: 12
<212> TYPE: PRT
<213> ORGANISM: Mus musculus

<400> SEQUENCE: 402

Ser Ala Leu Ile Lys Lys Lys Lys Lys Met Ala Pro
1               5                   10

<210> SEQ ID NO 403
<211> LENGTH: 5
<212> TYPE: PRT
<213> ORGANISM: Influenza virus

<400> SEQUENCE: 403

Asp Arg Leu Arg Arg
1               5

<210> SEQ ID NO 404
<211> LENGTH: 7
<212> TYPE: PRT
<213> ORGANISM: Influenza virus

<400> SEQUENCE: 404

Pro Lys Gln Lys Lys Arg Lys
1               5

<210> SEQ ID NO 405
<211> LENGTH: 10
<212> TYPE: PRT
<213> ORGANISM: Hepatitis D virus

<400> SEQUENCE: 405

Arg Lys Leu Lys Lys Lys Ile Lys Lys Leu
1               5                   10

<210> SEQ ID NO 406
<211> LENGTH: 10
<212> TYPE: PRT
<213> ORGANISM: Mus musculus
```

```
<400> SEQUENCE: 406

Arg Glu Lys Lys Lys Phe Leu Lys Arg Arg
1               5                   10

<210> SEQ ID NO 407
<211> LENGTH: 20
<212> TYPE: PRT
<213> ORGANISM: Homo sapiens

<400> SEQUENCE: 407

Lys Arg Lys Gly Asp Glu Val Asp Gly Val Asp Glu Val Ala Lys Lys
1               5                   10                  15

Lys Ser Lys Lys
            20

<210> SEQ ID NO 408
<211> LENGTH: 17
<212> TYPE: PRT
<213> ORGANISM: Homo sapiens

<400> SEQUENCE: 408

Arg Lys Cys Leu Gln Ala Gly Met Asn Leu Glu Ala Arg Lys Thr Lys
1               5                   10                  15

Lys

<210> SEQ ID NO 409
<211> LENGTH: 21
<212> TYPE: DNA
<213> ORGANISM: Campylobacter jejuni

<400> SEQUENCE: 409
tccaggaaag agaaacctcc c                                         21

<210> SEQ ID NO 410
<211> LENGTH: 21
<212> TYPE: DNA
<213> ORGANISM: Campylobacter jejuni

<400> SEQUENCE: 410
cattcaggaa agtacattgg c                                         21

<210> SEQ ID NO 411
<211> LENGTH: 20
<212> TYPE: DNA
<213> ORGANISM: Artificial sequence
<220> FEATURE:
<223> OTHER INFORMATION: Forward primer

<400> SEQUENCE: 411
acggaaaata tcaagaagta                                           20

<210> SEQ ID NO 412
<211> LENGTH: 21
<212> TYPE: DNA
<213> ORGANISM: Artificial sequence
<220> FEATURE:
<223> OTHER INFORMATION: Reverse primer

<400> SEQUENCE: 412
cagcaagccc tgtcctgctg g                                         21
```

```
<210> SEQ ID NO 413
<211> LENGTH: 13
<212> TYPE: RNA
<213> ORGANISM: Campylobacter jejuni

<400> SEQUENCE: 413
guuuuagucc cuu                                                              13
```